US006464974B1

(12) United States Patent
Berlin et al.

(10) Patent No.: US 6,464,974 B1
(45) Date of Patent: Oct. 15, 2002

(54) IMMUNOSUPPRESSANT TARGET PROTEINS

(75) Inventors: Vivian Berlin, Dunstable, MA (US); Maria Isabel Chiu, Boston, MA (US); Guillaume Cottarel, West Roxbury, MA (US); Veronique Damagnez, Cambridge, MA (US)

(73) Assignee: Ariad Pharmaceuticals, Cambridge, MA (US)

( * ) Notice: Subject to any disclaimer, the term of this patent is extended or adjusted under 35 U.S.C. 154(b) by 0 days.

(21) Appl. No.: 09/012,504

(22) Filed: Jan. 23, 1998

Related U.S. Application Data

(63) Continuation of application No. 08/360,144, filed on Dec. 20, 1994, now Pat. No. 6,150,137, which is a continuation-in-part of application No. 08/250,795, filed on May 27, 1994, now abandoned.

(51) Int. Cl.[7] .................. C07K 16/00; C07K 14/40; C12P 21/08; A61K 39/395

(52) U.S. Cl. ................. 424/139.1; 424/146.1; 530/350; 530/387.9; 530/388.26

(58) Field of Search ................ 435/194; 530/387.9, 530/300, 350, 866, 388.26; 424/139.1, 146.1

(56) References Cited

U.S. PATENT DOCUMENTS

| 3,929,992 A | 12/1975 | Sehgal et al. ........... 424/122 |
|---|---|---|
| 5,283,317 A | 2/1994 | Saifer et al. ........... 528/405 |
| 5,322,772 A | 6/1994 | Soldin ................ 435/7.9 |
| 5,354,845 A | 11/1994 | Soldin ................ 530/350 |
| 5,968,761 A | * 10/1999 | Rolfe et al. |

FOREIGN PATENT DOCUMENTS

WO   WO 94/10300   5/1994

OTHER PUBLICATIONS

Parham et al. Human Immunology vol. 3, pp. 277–299, 1981.*
Database a–geneseq35 Accession No. W04235, Nov. 1996.*
Alarcon, C. et al., "Mammalian RAFT1 Kinase Domain provides Rapamycin–sensitive TOR Function in Yeast", *Genes Dev.* 10(3) : 279–288 (1996).
Albers, M. et al., "FKBP–Rapamycin inhibits a Cyclin–dependent Kinase activity and a Cyclin D1–Cdk Association in Early G1 of an Osteosarcoma Cell Line", *J. Biol. Chem.* 268: 22825–22829 (1993).
Barbet, N. et al., "TOR Controls Translation Initiation and Early G1 Progression In Yeast", *Mol. Biol. Cell* 7(1): 25–42 (1996).
Bierer, B. et al., "Probing Immunosuppressant Action with a Nonnatural Immunophilin Ligand", *Science* 250: 556–559 (1990).

Bierer, B. et al., "Two Distinct Signal Transmission Pathways in T Lymphochtes are Inhibited by Complexes Formed between and Immunophilin and either FK506 or Rapamycin", *Proc. Nat. Acad. Sci. USA* 87: 231–9235 (1990).
Brown, et al., "A Mammalian Protein Taregeted by G1–arresting Rapamycin–receptor Complex", *Nature* 369: 756–758 (1994).
Cafferkey, R. et al., "Dominant Missense Mutations in a Novel Yeast Protein Related to Mammalian Phosphatidylinositol 3–Kinase and VPS34 Abrogate Rapamycin Cytotoxicity", *Mol. Cell. Biol.* 13: 6012–6023 (1993).
Cafferkey, R. et al., "Yeast TOR (DRR) Proteins: Amino–acid Sequence Alignment and Identification of Structural Motifs", *Gene* 141: 133–136 (1994).
Cardenas, M. and Heitman, J. "FKBP12–rapamycin Target TOR2 is a Vacuolar Protein with an Associated Phosphatidylinositol–4 Kinase Activity", *EMBO J.* 14(23): 5892–5907 (1995).
Chui, M. et al., "RAPT1, a Mammalian Homolog of Yeast Tor, Interacts with the FKBP12/rapamycin Complex", *Proc. Nat. Acad. Sci. USA* 91: 12574–12578 (1994).
Chung, J. et al., "Rapamycin–FKBP Specifically Blocks Growth–Dependent Activation of and Signaling by the 70 kd S6 Protein Kinases", *Cell* 69: 1227–1236 (1992).
DiLella, A. and Craig, R., "Exon Organization of the Human FKBP–12 Gene: Correlation with Structural and Functional Protein Domains", *Biochem.* 30: 8512–8517 (1991).
Draetta, G., "Cell Cycle Control in Ekaryotes: Molecular Mechanisms of cdc2 Activation", *Trends Biol. Sci.* 15: 378–383 (1990).
Dumont, F. et al., "The Immunosuppresive Macrolides FK–506 and Rapamycin Act as Reciprocal Antagonists in Murine T Cells", *J. Immunol.* 144: 1418–1424 (1990).
Ferrara, A. et al., "Cloning and Sequence Analysis of a Rapamycin–binding Protein–encoding Gene (RBP1) from Candida Albicans", *Gene* 113: 125–127 (1992).
Francavilla, A. et al., "Effects of Rapamycin on Cultured Hepatocyte Proliferation and Gene Expression", *Hepatol.* 15: 871–877 (1992).
Freeman, K. and Livi, G., "Missense Mutations at the FKBP12–rapamycin–binding Site of TOR1", *Gene* 172(1): 143–147 (1996).
Fruman, D. et al., "Immunophilins in Protein Folding and Immunosuppression", *FASEB J.* 8: 391–400 (1994).
Galat, A. "Peptidylproline cis–trans–isomerases: Immunophilins", *Eur. J. Biochem.* 216: 689–707 (1993).

(List continued on next page.)

Primary Examiner—Christina Chan
Assistant Examiner—Margaret E. Jamroz
(74) Attorney, Agent, or Firm—Ropes & Gray; Matthew F. Vincent

(57) ABSTRACT

The present invention relates to the discovery of novel proteins of mammalian origin which are immediate downstream targets for FKBP/rapamycin complexes and provides, e.g., isolated polypeptides, nucleic acids encoding such, antibodies, screening methods, and diagnostic and therepeutic methods.

17 Claims, 4 Drawing Sheets

OTHER PUBLICATIONS

Harding, M. et al., "A Receptor for the Immunosuppressant FK506 is a cis–trans Peptidyl–prolyl Isomerase", *Nature* 341: 758–760 (1989).

Heitman, J. et al., "Targets for Cell Cycle Arrest by the Immunosuppressant Rapamycin in Yeast", *Science* 253: 905–909 (1991).

Helliwell, S. et al., "TOR1 and TOR2 are Structurally and Functionally Similar but not Identical Phosphatiylinositol Kinase Homologues in Yeast", *Mol. Biol. Cell.* 5: 105–118 (1994).

Huang, M. et al., Analysis of a 62 kb DNA Sequence of Chromosome X Reveals 36 Open Reading Frames and a Gene Cluster with a Counterpart on Chromosome XI, *Yeast* 12 (9): 869–875 (1996).

Kato, R. and Ogawa, H., "An Essential Gene, ESR1, is Required for Mitotic Cell Growth, DNA Repair and Meiotic Recombination in Saccharomyces Cerevisiae", *Nucl.eic Acid Res.* 22(15): 3104–3112 (1994).

Kunz, J. et al., "Target of Rapamycin in Yeast, TOR2, Is an Essential Phosphatidylinositol Kinase Homolog Required for $G_1$ Progression", *Cell* 73: 585–596 (1993).

Lorenz, M. and Heitman, J., "TOR Mutations Confer Rapamycin Resistance by Preventing Interaction with FKBP12–Rapamycin", *J. Biol. Chem.* 270(46): 27531–27537 (1995).

Morice, W. et al., "Rapamycin–induced inhibition of p34$^{cdc2}$ Kinase Activation is Associated with $G_1$/S–phase Growth Arrest in T Lymphocytes", *J. Biol. Chem.* (268): 3734–3738 (1993).

Pardee, A., "$G_1$ Events and Regulation of Cell Proliferation", *Science* 246: 603–608 (1989).

Price, D. et al., "Rapamycin–Induced Inhibition of the 70–Kilodalton S6 Protein Kinase", *Science* 257: 973–977 (1992).

Sabatini, D. et al., "The Rapamycin and FKBP12 Target (RAFT) Displays Phosphatidylinositol 4–Kinase Activity", *J. Biol. Chem.* 270(36): 20875–20878 (1995).

Sabatini, D. et al., "RAFT1: A Mammalian Protein that Binds to FKBP12 in a Rapamycin–dependent Fashion and is Homologous to Yeast TORs", *Cell* 78: 35–38 (1994).

Sabers, C. et al., "Isolation of a Protein Target of the FKBP12–rapamycin Complex in Mammalian Cells", *J. Biol. Chem.* 270: 815–822 (1995).

Schmidt, A. et al., "TOR2 is Required for Organization of the Actin Cytoskeleton in Yeast", *Proc. Nat. Acad. Sci. USA* 93(24): 13780–13785 (1996).

Schreiber, S., "Immunophilin–sensitive Protein Phosphatase Action in Cell Signaling Pathways", *Cell* 70: 365–368 (1992).

Schreiber, S. and Crabtree, G., "The Mechanism of Action of Cyclosporin A and FK506", *Immunol. Today 13*: 136–142 (1992).

Sehgal, S. et al., "Rapamycin (AY–22,989), A New Antifungal Antibiotic. II. Fermentation, Isolation and Characterization", *J. Antibiotics* 28: 727–732 (1975).

Sherr, C., "Mammalian $G_1$ Cyclins", *Cell* 73: 1059–1065 (1993).

Siekierka, J. et al., A Cytosolic Binding Protein for the Immunosuppressant FK506 has Peptidylprolyl Isomerase Activity but is Distinct from Cyclophilin:, *Nature* 341: 755–757 (1989).

Sigal, N. and Dumont, F., "Cyclosporin A, FK–506, and Rapamycin: Pharmacologic Probes of Lymphocyte Signal Transduction", *Ann. Rev. Immunol.* 10: 519–560 (1992).

Sigal, N. et al., "Inhibition of Human T–cell Activation by FK 506, Rapamycin, and Cyclosporine A", *Transplantation Proc.* 23 (2 Supp. 2): 1–5 (*1991*).

Silver, L. et al. "TOR1 is a Novel, Varient Form of Mouse Chromosome 17 with a Deletion in a Partial Haplotype", *Nature 301(5899)*: 422–424 (1983).

Soltoff, S. et al., "Nerve Growth Factor Promotes the Activation of Phosphatidylinositol 3–Kinase and its Association with the *trk* Tryosine Kinase", *J. Biol. Chem.* 267: 17472–17477 (1992).

Stan, R. et al., "Interaction between FKBP12–rapamycin and TOR Involves a Conserved Serine Residue", *J. Biol. Chem.* 269(51): 32027–32030 (1994).

Van Duyne, G. et al., "Atomic Structure of FKBP–FK506, an immunophilin–immunosuppressant Complex", *Science* 252: 839–843 (1991).

Van Duyne, G. et al., "Atomic Structures of the Human Immunophilin FKBP–12 Complexes with FK506 and Rapamycin", *J. Mol. Biol.* 229: 105–124 (1993).

Vezina, C. et al., "Rapamycin (AY–22,989), a New Antifungal Antibiotic. I. Taxonomy of the Producing Streptomycete and Isolation of the Active Principle", *J. Antibiotics* 28: 721–726 (1975).

Walsh, C. et al., "Cyclosporin A, the Cyclophilin Class of Peptidylprolyl Isomerases and Blockade of T Cell Signal Transduction", *J. Biol. Chem.* 267: 13115–13118 (1992).

Zheng, X. et al., "TOR Kinase Domains are Required for Two Distinct Functions, Only One of which is Inhibited by Rapamycin", *Cell 82(1)*: 121–130 (1995).

Berlin, V. "Identification of Novel Immunosuppressant", Abstract of NIH Grant R431AI34189 (1993).

International Search Report, Oct. 1995.

\* cited by examiner

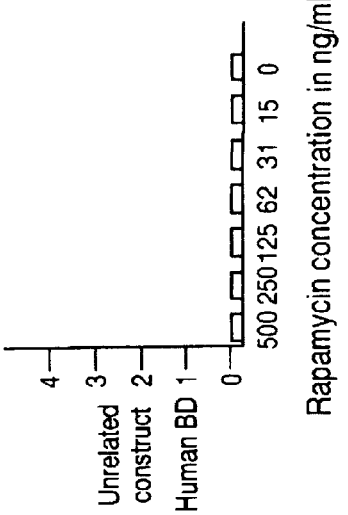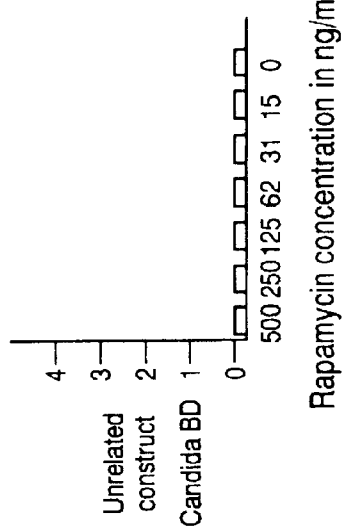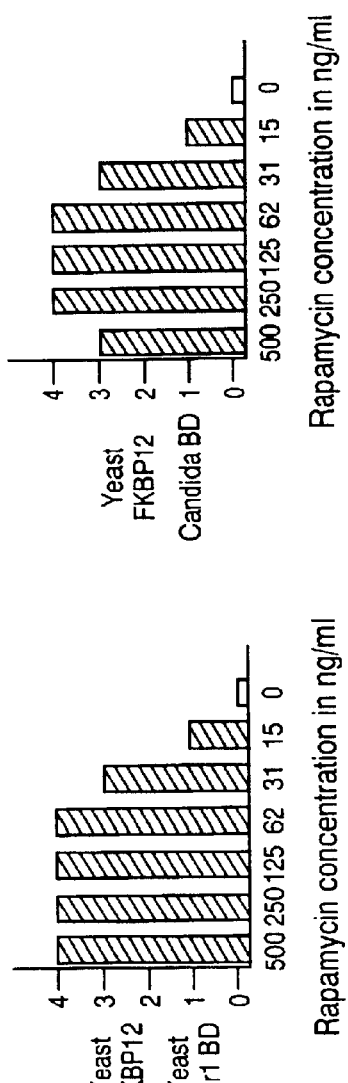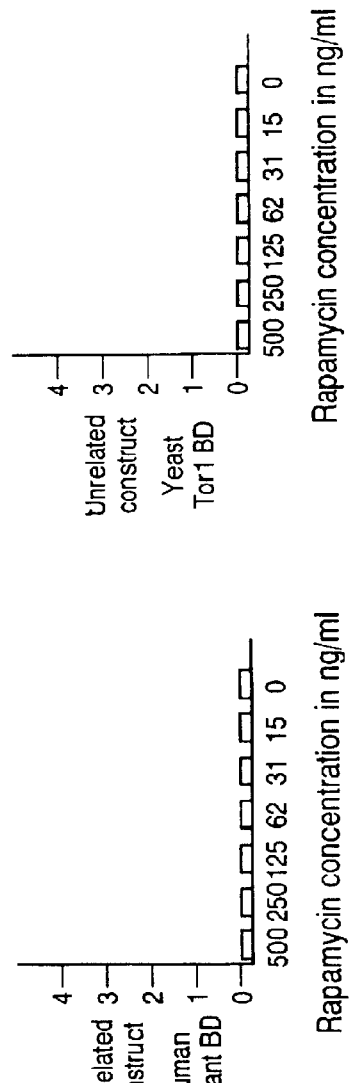

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 486 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: CDS
      (B) LOCATION: 1..486

(xi) SEQUENCE DESCRIPTION: SEQ ID NO:1:

```
CTC ACC CGT CAC AAT GCA GCC AAC AAG ATC TTG AAG AAC ATG TGT GAA        48
Leu Thr Arg His Asn Ala Ala Asn Lys Ile Leu Lys Asn Met Cys Glu
 1               5                  10                  15

CAC AGC AAC ACG CTG GTC CAG CAG GCC ATG ATG GTG AGT GAA GAG CTG        96
His Ser Asn Thr Leu Val Gln Gln Ala Met Met Val Ser Glu Glu Leu
            20                  25                  30

ATT CGG GTA GCC ATC CTC TGG CAT GAG ATG TGG CAT GAA GGC CTG GAA       144
Ile Arg Val Ala Ile Leu Trp His Glu Met Trp His Glu Gly Leu Glu
        35                  40                  45

GAG GCA TCT CGC TTG TAC TTT GGG GAG AGG AAC GTG AAA GGC ATG TTT       192
Glu Ala Ser Arg Leu Tyr Phe Gly Glu Arg Asn Val Lys Gly Met Phe
    50                  55                  60

GAG GTG CTG GAG CCC CTG CAT GCT ATG ATG GAA CGG GGT CCC CGG ACT       240
Glu Val Leu Glu Pro Leu His Ala Met Met Glu Arg Gly Pro Arg Thr
65                  70                  75                  80

CTG AAG GAA ACA TCC TTT AAT CAG GCA TAT GGC CGA GAT TTA ATG GAG       288
Leu Lys Glu Thr Ser Phe Asn Gln Ala Tyr Gly Arg Asp Leu Met Glu
                85                  90                  95

GCA CAA GAA TGG TGT CGA AAG TAC ATG AAG TCG GGG AAC GTC AAG GAC       336
Ala Gln Glu Trp Cys Arg Lys Tyr Met Lys Ser Gly Asn Val Lys Asp
```

|   |   |   |   |   |   |   |   |   |   |   |   |   |   |   |   |
|---|---|---|---|---|---|---|---|---|---|---|---|---|---|---|---|
|   |   |   |   | 100 |   |   |   |   | 105 |   |   |   |   | 110 |   |
| CTC | ACG | CAA | GCC | TGG | GAC | CTC | TAC | TAT | CAC | GTG | TTC | AGA | CGG | ATC | TCA | 384
| Leu | Thr | Gln | Ala | Trp | Asp | Leu | Tyr | Tyr | His | Val | Phe | Arg | Arg | Ile | Ser |
|   |   | 115 |   |   |   | 120 |   |   |   | 125 |   |   |   |   |   |

| AAG | CAG | CTA | CCC | CAG | CTC | ACA | TCC | CTG | GAG | CTG | CAG | TAT | GTG | TCC | CCC | 432
| Lys | Gln | Leu | Pro | Gln | Leu | Thr | Ser | Leu | Glu | Leu | Gln | Tyr | Val | Ser | Pro |
| 130 |   |   |   |   | 135 |   |   |   |   | 140 |   |   |   |   |   |

| AAA | CTT | CTG | ATG | TGC | CGA | GAC | CTT | GAG | TTG | GCT | GTG | CCA | GGA | ACA | TAC | 480
| Lys | Leu | Leu | Met | Cys | Arg | Asp | Leu | Glu | Leu | Ala | Val | Pro | Gly | Thr | Tyr |
| 145 |   |   |   | 150 |   |   |   |   | 155 |   |   |   |   | 160 |   |

| GAC | CCC | | | | | | | | | | | | | | | 486
| Asp | Pro |

(2) INFORMATION FOR SEQ ID NO:2:

(i) SEQUENCE CHARACTERISTICS:
        (A) LENGTH: 162 amino acids
        (B) TYPE: amino acid
        (D) TOPOLOGY: linear (ii) MOLECULE TYPE: protein (xi) SEQUENCE DESCRIPTION: SEQ ID NO:2:

Leu Thr Arg His Asn Ala Ala Asn Lys Ile Leu Lys Asn Met Cys Glu
 1             5                  10               15

His Ser Asn Thr Leu Val Gln Gln Ala Met Met Val Ser Glu Glu Leu
           20                 25               30

Ile Arg Val Ala Ile Leu Trp His Glu Met Trp His Glu Gly Leu Glu
          35                 40               45

Glu Ala Ser Arg Leu Tyr Phe Gly Glu Arg Asn Val Lys Gly Met Phe
 50                  55                  60

Glu Val Leu Glu Pro Leu His Ala Met Met Glu Arg Gly Pro Arg Thr
 65               70                  75              80

Leu Lys Glu Thr Ser Phe Asn Gln Ala Tyr Gly Arg Asp Leu Met Glu
           85                 90               95

Ala Gln Glu Trp Cys Arg Lys Tyr Met Lys Ser Gly Asn Val Lys Asp
          100                105             110

Leu Thr Gln Ala Trp Asp Leu Tyr Tyr His Val Phe Arg Arg Ile Ser
        115                120             125

Lys Gln Leu Pro Gln Leu Thr Ser Leu Glu Leu Gln Tyr Val Ser Pro
 130                 135              140

Lys Leu Leu Met Cys Arg Asp Leu Glu Leu Ala Val Pro Gly Thr Tyr
 145              150               155              160

Asp Pro (2) INFORMATION FOR SEQ ID NO:3:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

GGGTTTGGAA TTCCTAATAA TGTCTGTACA AGTAGAAACC                      40

(2) INFORMATION FOR SEQ ID NO:4:

```
    (i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

GGGTTTCGGG ATCCCGTCAT TCCAGTTTTA CAAC                                34

(2) INFORMATION FOR SEQ ID NO:5:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 14..325

(xi) SEQUENCE DESCRIPTION: SEQ ID NO:5:

GGAATTCCTA ATA ATG TCC GTA CAA GTA GAA ACC ATC TCC CCA GGA GAC       49
           Met Ser Val Gln Val Glu Thr Ile Ser Pro Gly Asp
             1               5                  10

GGG CGC ACC TTC CCC AAG CGC GGC CAG ACC TGC GTG GTG CAC TAC ACC      97
Gly Arg Thr Phe Pro Lys Arg Gly Gln Thr Cys Val Val His Tyr Thr
         15                  20                  25

GGG ATG CTT GAA GAT GGA AAG AAA TTT GAT TCC TCC CGT GAC CGT AAC     145
Gly Met Leu Glu Asp Gly Lys Lys Phe Asp Ser Ser Arg Asp Arg Asn
     30                  35                  40

AAG CCC TTT AAG TTT ATG CTA GGC AAG CAG GAG GTG ATC CGA GGC TGG     193
Lys Pro Phe Lys Phe Met Leu Gly Lys Gln Glu Val Ile Arg Gly Trp
 45                  50                  55                  60

GAA GAA GGG GTT GCC CAG ATG AGT GTG GGT CAG CGT GCC AAA CTG ACT     241
Glu Glu Gly Val Ala Gln Met Ser Val Gly Gln Arg Ala Lys Leu Thr
                 65                  70                  75

ATA TCT CCA GAT TAT GCC TAT GGT GCC ACT GGG CAC CCA GGC ATC ATC     289
Ile Ser Pro Asp Tyr Ala Tyr Gly Ala Thr Gly His Pro Gly Ile Ile
             80                  85                  90

CCA CCA CAT GCC ACT CTC GTC TTC GAT GTG GAG CTT CTAAAACTGG          335
Pro Pro His Ala Thr Leu Val Phe Asp Val Glu Leu
         95                 100

AATGACGGGA TCC                                                      348

(2) INFORMATION FOR SEQ ID NO:6:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO:6:

Met Ser Val Gln Val Glu Thr Ile Ser Pro Gly Asp Gly Arg Thr Phe
  1               5                  10                  15

Pro Lys Arg Gly Gln Thr Cys Val Val His Tyr Thr Gly Met Leu Glu
             20                  25                  30

Asp Gly Lys Lys Phe Asp Ser Ser Arg Asp Arg Asn Lys Pro Phe Lys
         35                  40                  45
```

```
Phe Met Leu Gly Lys Gln Glu Val Ile Arg Gly Trp Glu Glu Gly Val
     50                  55                  60

Ala Gln Met Ser Val Gly Gln Arg Ala Lys Leu Thr Ile Ser Pro Asp
 65                  70                  75                  80

Tyr Ala Tyr Gly Ala Thr Gly His Pro Gly Ile Ile Pro Pro His Ala
                 85                  90                  95

Thr Leu Val Phe Asp Val Glu Leu
            100
```

(2) INFORMATION FOR SEQ ID NO:7:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

```
TCGCCGGAAT TCGGGGGCGG AGGTGGAGGA GTACAAGTAG AAACCATC              48
```

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

```
GGGTTTCGGG ATCCCGTCAT TCCAGTTTTA GAAG                             34
```

(2) INFORMATION FOR SEQ ID NO:9:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

```
CGCGGATCCG CGCATTATTA CTTGTTTTGA TTGATTTTTT G                     41
```

(2) INFORMATION FOR SEQ ID NO:10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

```
CGCGGATCCG CGTAAAAGCA AAGTACTATC AATTGAGCCG                       40
```

(2) INFORMATION FOR SEQ ID NO:11:

(i) SEQUENCE CHARACTERISTICS:
        (A) LENGTH: 5430 base pairs
        (B) TYPE: nucleic acid

```
      (C) STRANDEDNESS: both
      (D) TOPOLOGY: linear (ii) MOLECULE TYPE: cDNA (ix) FEATURE:
      (A) NAME/KEY: CDS
      (B) LOCATION: 1..5427

(xi) SEQUENCE DESCRIPTION: SEQ ID NO:11:

TTG GAG CAC AGT GGG ATT GGA AGA ATC AAA GAG CAG AGT GCC CGC ATG        48
Leu Glu His Ser Gly Ile Gly Arg Ile Lys Glu Gln Ser Ala Arg Met
 1               5                  10                  15

CTG GGG CAC CTG GTC TCC AAT GCC CCC CGA CTC ATC CGC CCC TAC ATG        96
Leu Gly His Leu Val Ser Asn Ala Pro Arg Leu Ile Arg Pro Tyr Met
             20                  25                  30

GAG CCT ATT CTG AAG GCA TTA ATT TTG AAA CTG AAA GAT CCA GAC CCT       144
Glu Pro Ile Leu Lys Ala Leu Ile Leu Lys Leu Lys Asp Pro Asp Pro
         35                  40                  45

GAT CCA AAC CCA GGT GTG ATC AAT AAT GTC CTG GCA ACA ATA GGA GAA       192
Asp Pro Asn Pro Gly Val Ile Asn Asn Val Leu Ala Thr Ile Gly Glu
     50                  55                  60

TTG GCA CAG GTT AGT GGC CTG GAA ATG AGG AAA TGG GTT GAT GAA CTT       240
Leu Ala Gln Val Ser Gly Leu Glu Met Arg Lys Trp Val Asp Glu Leu
 65                  70                  75                  80

TTT ATT ATC ATC ATG GAC ATG CTC CAG GAT TCC TCT TTG TTG GCC AAA       288
Phe Ile Ile Ile Met Asp Met Leu Gln Asp Ser Ser Leu Leu Ala Lys
                 85                  90                  95

AGG CAG GTG GCT CTG TGG ACC CTG GGA CAG TTG GTG GCC AGC ACT GGC       336
Arg Gln Val Ala Leu Trp Thr Leu Gly Gln Leu Val Ala Ser Thr Gly
            100                 105                 110

TAT GTA GTA GAG CCC TAC AGG AAG TAC CCT ACT TTG CTT GAG GTG CTA       384
Tyr Val Val Glu Pro Tyr Arg Lys Tyr Pro Thr Leu Leu Glu Val Leu
        115                 120                 125

CTG AAT TTT CTG AAG ACT GAG CAG AAC CAG GGT ACA CGC AGA GAG GCC       432
Leu Asn Phe Leu Lys Thr Glu Gln Asn Gln Gly Thr Arg Arg Glu Ala
    130                 135                 140

ATC CGT GTG TTA GGG CTT TTA GGG GCT TTG GAT CCT TAC AAG CAC AAA       480
Ile Arg Val Leu Gly Leu Leu Gly Ala Leu Asp Pro Tyr Lys His Lys
145                 150                 155                 160

GTG AAC ATT GGC ATG ATA GAC CAG TCC CGG GAT GCC TCT GCT GTC AGC       528
Val Asn Ile Gly Met Ile Asp Gln Ser Arg Asp Ala Ser Ala Val Ser
                165                 170                 175

CTG TCA GAA TCC AAG TCA AGT CAG GAT TCC TCT GAC TAT AGC ACT AGT       576
Leu Ser Glu Ser Lys Ser Ser Gln Asp Ser Ser Asp Tyr Ser Thr Ser
            180                 185                 190

GAA ATG CTG GTC AAC ATG GGA AAC TTG CCT CTG GAT GAG TTC TAC CCA       624
Glu Met Leu Val Asn Met Gly Asn Leu Pro Leu Asp Glu Phe Tyr Pro
        195                 200                 205

GCT GTG TCC ATG GTG GCC CTG ATG CGG ATC TTC CGA GAC CAG TCA CTC       672
Ala Val Ser Met Val Ala Leu Met Arg Ile Phe Arg Asp Gln Ser Leu
    210                 215                 220

TCT CAT CAT CAC ACC ATG GTT GTC CAG GCC ATC ACC TTC ATC TTC AAG       720
Ser His His His Thr Met Val Val Gln Ala Ile Thr Phe Ile Phe Lys
225                 230                 235                 240

TCC CTG GGA CTC AAA TGT GTG CAG TTC CTG CCC CAG GTC ATG CCC ACG       768
Ser Leu Gly Leu Lys Cys Val Gln Phe Leu Pro Gln Val Met Pro Thr
                245                 250                 255

TTC CTT AAT GTC ATT CGA GTC TGT GAT GGG GCC ATC CGG GAA TTT TTG       816
Phe Leu Asn Val Ile Arg Val Cys Asp Gly Ala Ile Arg Glu Phe Leu
            260                 265                 270
```

```
TTC CAG CAG CTG GGA ATG TTG GTG TCC TTT GTG AAG AGC CAC ATC AGA      864
Phe Gln Gln Leu Gly Met Leu Val Ser Phe Val Lys Ser His Ile Arg
            275                 280                 285

CCT TAT ATG GAT GAA ATA GTC ACC CTC ATG AGA GAA TTC TGG GTC ATG      912
Pro Tyr Met Asp Glu Ile Val Thr Leu Met Arg Glu Phe Trp Val Met
        290                 295                 300

AAC ACC TCA ATT CAG AGC ACG ATC ATT CTT CTC ATT GAG CAA ATT GTG      960
Asn Thr Ser Ile Gln Ser Thr Ile Ile Leu Leu Ile Glu Gln Ile Val
305                 310                 315                 320

GTA GCT CTT GGG GGT GAA TTT AAG CTC TAC CTG CCC CAG CTG ATC CCA     1008
Val Ala Leu Gly Gly Glu Phe Lys Leu Tyr Leu Pro Gln Leu Ile Pro
                325                 330                 335

CAC ATG CTG CGT GTC TTC ATG CAT GAC AAC AGC CCA GGC CGC ATT GTC     1056
His Met Leu Arg Val Phe Met His Asp Asn Ser Pro Gly Arg Ile Val
            340                 345                 350

TCT ATC AAG TTA CTG GCT GCA ATC CAG CTG TTT GGC GCC AAC CTG GAT     1104
Ser Ile Lys Leu Leu Ala Ala Ile Gln Leu Phe Gly Ala Asn Leu Asp
        355                 360                 365

GAC TAC CTG CAT TTA CTG CTG CCT CCT ATT GTT AAG TTG TTT GAT GCC     1152
Asp Tyr Leu His Leu Leu Leu Pro Pro Ile Val Lys Leu Phe Asp Ala
370                 375                 380

CCT GAA GCT CCA CTG CCA TCT CGA AAG GCA GCG CTA GAG ACT GTG GAC     1200
Pro Glu Ala Pro Leu Pro Ser Arg Lys Ala Ala Leu Glu Thr Val Asp
385                 390                 395                 400

CGC CTG ACG GAG TCC CTG GAT TTC ACT GAC TAT GCC TCC CGG ATC ATT     1248
Arg Leu Thr Glu Ser Leu Asp Phe Thr Asp Tyr Ala Ser Arg Ile Ile
                405                 410                 415

CAC CCT ATT GTT CGA ACA CTG GAC CAG AGC CCA GAA CTG CGC TCC ACA     1296
His Pro Ile Val Arg Thr Leu Asp Gln Ser Pro Glu Leu Arg Ser Thr
            420                 425                 430

GCC ATG GAC ACG CTG TCT TCA CTT GTT TTT CAG CTG GGG AAG AAG TAC     1344
Ala Met Asp Thr Leu Ser Ser Leu Val Phe Gln Leu Gly Lys Lys Tyr
        435                 440                 445

CAA ATT TTC ATT CCA ATG GTG AAT AAA GTT CTG GTG CGA CAC CGA ATC     1392
Gln Ile Phe Ile Pro Met Val Asn Lys Val Leu Val Arg His Arg Ile
450                 455                 460

AAT CAT CAG CGC TAT GAT GTG CTC ATC TGC AGA ATT GTC AAG GGA TAC     1440
Asn His Gln Arg Tyr Asp Val Leu Ile Cys Arg Ile Val Lys Gly Tyr
465                 470                 475                 480

ACA CTT GCT GAT GAA GAG GAG GAT CCT TTG ATT TAC CAG CAT CGG ATG     1488
Thr Leu Ala Asp Glu Glu Glu Asp Pro Leu Ile Tyr Gln His Arg Met
                485                 490                 495

CTT AGG AGT GGC CAA GGG GAT GCA TTG GCT AGT GGA CCA GTG GAA ACA     1536
Leu Arg Ser Gly Gln Gly Asp Ala Leu Ala Ser Gly Pro Val Glu Thr
            500                 505                 510

GGA CCC ATG AAG AAA CTG CAC GTC AGC ACC ATC AAC CTC CAA AAG GCC     1584
Gly Pro Met Lys Lys Leu His Val Ser Thr Ile Asn Leu Gln Lys Ala
        515                 520                 525

TGG GGC GCT GCC AGG AGG GTC TCC AAA GAT GAC TGG CTG GAA TGG CTG     1632
Trp Gly Ala Ala Arg Arg Val Ser Lys Asp Asp Trp Leu Glu Trp Leu
530                 535                 540

AGA CGG CTG AGC CTG GAG CTG CTG AAG GAC TCA TCA TCG CCC TCC CTG     1680
Arg Arg Leu Ser Leu Glu Leu Leu Lys Asp Ser Ser Ser Pro Ser Leu
545                 550                 555                 560

CGC TCC TGC TGG GCC CTG GCA CAG GCC TAC AAC CCG ATG GCC AGG GAT     1728
Arg Ser Cys Trp Ala Leu Ala Gln Ala Tyr Asn Pro Met Ala Arg Asp
                565                 570                 575

CTC TTC AAT GCT GCA TTT GTG TCC TGC TGG TCT GAA CTG AAT GAA GAT     1776
Leu Phe Asn Ala Ala Phe Val Ser Cys Trp Ser Glu Leu Asn Glu Asp
            580                 585                 590
```

```
                                                      -continued

CAA CAG GAT GAG CTC ATC AGA AGC ATC GAG TTG GCC CTC ACC TCA CAA    1824
Gln Gln Asp Glu Leu Ile Arg Ser Ile Glu Leu Ala Leu Thr Ser Gln
            595                 600                 605

GAC ATC GCT GAA GTC ACA CAG ACC CTC TTA AAC TTG GCT GAA TTC ATG    1872
Asp Ile Ala Glu Val Thr Gln Thr Leu Leu Asn Leu Ala Glu Phe Met
        610                 615                 620

GAA CAC AGT GAC AAG GGC CCC CTG CCA CTG AGA GAT GAC AAT GGC ATT    1920
Glu His Ser Asp Lys Gly Pro Leu Pro Leu Arg Asp Asp Asn Gly Ile
625                 630                 635                 640

GTT CTG CTG GGT GAG AGA GCT GCC AAG TGC CGA GCA TAT GCC AAA GCA    1968
Val Leu Leu Gly Glu Arg Ala Ala Lys Cys Arg Ala Tyr Ala Lys Ala
                645                 650                 655

CTA CAC TAC AAA GAA CTG GAG TTC CAG AAA GGC CCC ACC CCT GCC ATT    2016
Leu His Tyr Lys Glu Leu Glu Phe Gln Lys Gly Pro Thr Pro Ala Ile
            660                 665                 670

CTA GAA TCT CTC ATC AGC ATT AAT AAT AAG CTA CAG CAG CCG GAG GCA    2064
Leu Glu Ser Leu Ile Ser Ile Asn Asn Lys Leu Gln Gln Pro Glu Ala
        675                 680                 685

GCG GCC GGA GTG TTA GAA TAT GCC ATG AAA CAC TTT GGA GAG CTG GAG    2112
Ala Ala Gly Val Leu Glu Tyr Ala Met Lys His Phe Gly Glu Leu Glu
    690                 695                 700

ATC CAG GCT ACC TGG TAT GAG AAA CTG CAC GAG TGG GAG GAT GCC CTT    2160
Ile Gln Ala Thr Trp Tyr Glu Lys Leu His Glu Trp Glu Asp Ala Leu
705                 710                 715                 720

GTG GCC TAT GAC AAG AAA ATG GAC ACC AAC AAG GAC GAC CCA GAG CTG    2208
Val Ala Tyr Asp Lys Lys Met Asp Thr Asn Lys Asp Asp Pro Glu Leu
                725                 730                 735

ATG CTG GGC CGC ATG CGC TGC CTC GAG GCC TTG GGG GAA TGG GGT CAA    2256
Met Leu Gly Arg Met Arg Cys Leu Glu Ala Leu Gly Glu Trp Gly Gln
            740                 745                 750

CTC CAC CAG CAG TGC TGT GAA AAG TGG ACC CTG GTT AAT GAT GAG ACC    2304
Leu His Gln Gln Cys Cys Glu Lys Trp Thr Leu Val Asn Asp Glu Thr
        755                 760                 765

CAA GCC AAG ATG GCC CGG ATG GCT GCT GCA GCT GCA TGG GGT TTA GGT    2352
Gln Ala Lys Met Ala Arg Met Ala Ala Ala Ala Ala Trp Gly Leu Gly
    770                 775                 780

CAG TGG GAC AGC ATG GAA GAA TAC ACC TGT ATG ATC CCT CGG GAC ACC    2400
Gln Trp Asp Ser Met Glu Glu Tyr Thr Cys Met Ile Pro Arg Asp Thr
785                 790                 795                 800

CAT GAT GGG GCA TTT TAT AGA GCT GTG CTG GCA CTG CAT CAG GAC CTC    2448
His Asp Gly Ala Phe Tyr Arg Ala Val Leu Ala Leu His Gln Asp Leu
                805                 810                 815

TTC TCC TTG GCA CAA CAG TGC ATT GAC AAG GCC AGG GAC CTG CTG GAT    2496
Phe Ser Leu Ala Gln Gln Cys Ile Asp Lys Ala Arg Asp Leu Leu Asp
            820                 825                 830

GCT GAA TTA ACT GCA ATG GCA GGA GAG AGT TAC AGT CGG GCA TAT GGG    2544
Ala Glu Leu Thr Ala Met Ala Gly Glu Ser Tyr Ser Arg Ala Tyr Gly
        835                 840                 845

GCC ATG GTT TCT TGC CAC ATG CTG TCC GAG CTG GAG GAG GTT ATC CAG    2592
Ala Met Val Ser Cys His Met Leu Ser Glu Leu Glu Glu Val Ile Gln
    850                 855                 860

TAC AAA CTT GTC CCC GAG CGA CGA GAG ATC ATC CGC CAG ATC TGG TGG    2640
Tyr Lys Leu Val Pro Glu Arg Arg Glu Ile Ile Arg Gln Ile Trp Trp
865                 870                 875                 880

GAG AGA CTG CAG GGC TGC CAG CGT ATC GTA GAG GAC TGG CAG AAA ATC    2688
Glu Arg Leu Gln Gly Cys Gln Arg Ile Val Glu Asp Trp Gln Lys Ile
                885                 890                 895

CTT ATG GTG CGG TCC CTT GTG GTC AGC CCT CAT GAA GAC ATG AGA ACC    2736
Leu Met Val Arg Ser Leu Val Val Ser Pro His Glu Asp Met Arg Thr
```

-continued

```
                 900                    905                    910
TGG CTC AAG TAT GCA AGC CTG TGC GGC AAG AGT GGC AGG CTG GCT CTT    2784
Trp Leu Lys Tyr Ala Ser Leu Cys Gly Lys Ser Gly Arg Leu Ala Leu
            915                    920                    925

GCT CAT AAA ACT TTA GTG TTG CTC CTG GGA GTT GAT CCG TCT CGG CAA    2832
Ala His Lys Thr Leu Val Leu Leu Leu Gly Val Asp Pro Ser Arg Gln
        930                    935                    940

CTT GAC CAT CCT CTG CCA ACA GTT CAC CCT CAG GTG ACC TAT GCC TAC    2880
Leu Asp His Pro Leu Pro Thr Val His Pro Gln Val Thr Tyr Ala Tyr
945                    950                    955                    960

ATG AAA AAC ATG TGG AAG AGT GCC CGC AAG ATC GAT GCC TTC CAG CAC    2928
Met Lys Asn Met Trp Lys Ser Ala Arg Lys Ile Asp Ala Phe Gln His
                965                    970                    975

ATG CAG CAT TTT GTC CAG ACC ATG CAG CAA CAG GCC CAG CAT GCC ATC    2976
Met Gln His Phe Val Gln Thr Met Gln Gln Gln Ala Gln His Ala Ile
            980                    985                    990

GCT ACT GAG GAC CAG CAG CAT AAG CAG GAA CTG CAC AAG CTC ATG GCC    3024
Ala Thr Glu Asp Gln Gln His Lys Gln Glu Leu His Lys Leu Met Ala
        995                    1000                   1005

CGA TGC TTC CTG AAA CTT GGA GAG TGG CAG CTG AAT CTA CAG GGC ATC    3072
Arg Cys Phe Leu Lys Leu Gly Glu Trp Gln Leu Asn Leu Gln Gly Ile
        1010                   1015                   1020

AAT GAG AGC ACA ATC CCC AAA GTG CTG CAG TAC TAC AGC GCC GCC ACA    3120
Asn Glu Ser Thr Ile Pro Lys Val Leu Gln Tyr Tyr Ser Ala Ala Thr
1025                   1030                   1035                   1040

GAG CAC GAC CGC AGC TGG TAC AAG GCC TGG CAT GCG TGG GCA GTG ATG    3168
Glu His Asp Arg Ser Trp Tyr Lys Ala Trp His Ala Trp Ala Val Met
                1045                   1050                   1055

AAC TTC GAA GCT GTG CTA CAC TAC AAA CAT CAG AAC CAA GCC CGC GAT    3216
Asn Phe Glu Ala Val Leu His Tyr Lys His Gln Asn Gln Ala Arg Asp
            1060                   1065                   1070

GAG AAG AAG AAA CTG CGT CAT GCC AGC GGG GCC AAC ATC ACC AAC GCC    3264
Glu Lys Lys Lys Leu Arg His Ala Ser Gly Ala Asn Ile Thr Asn Ala
        1075                   1080                   1085

ACC ACT GCC GCC ACC ACG GCC GCC ACT GCC ACC ACC ACT GCC AGC ACC    3312
Thr Thr Ala Ala Thr Thr Ala Ala Thr Ala Thr Thr Thr Ala Ser Thr
        1090                   1095                   1100

GAG GGC AGC AAC AGT GAG AGC GAG GCC GAG AGC ACC GAG AAC AGC CCC    3360
Glu Gly Ser Asn Ser Glu Ser Glu Ala Glu Ser Thr Glu Asn Ser Pro
1105                   1110                   1115                   1120

ACC CCA TCG CCG CTG CAG AAG AAG GTC ACT GAG GAT CTG TCC AAA ACC    3408
Thr Pro Ser Pro Leu Gln Lys Lys Val Thr Glu Asp Leu Ser Lys Thr
                1125                   1130                   1135

CTC CTG ATG TAC ACG GTG CCT GCC GTC CAG GGC TTC TTC CGT TCC ATC    3456
Leu Leu Met Tyr Thr Val Pro Ala Val Gln Gly Phe Phe Arg Ser Ile
            1140                   1145                   1150

TCC TTG TCA CGA GGC AAC AAC CTC CAG GAT ACA CTC AGA GTT CTC ACC    3504
Ser Leu Ser Arg Gly Asn Asn Leu Gln Asp Thr Leu Arg Val Leu Thr
        1155                   1160                   1165

TTA TGG TTT GAT TAT GGT CAC TGG CCA GAT GTC AAT GAG GCC TTA GTG    3552
Leu Trp Phe Asp Tyr Gly His Trp Pro Asp Val Asn Glu Ala Leu Val
        1170                   1175                   1180

GAG GGG GTG AAA GCC ATC CAG ATT GAT ACC TGG CTA CAG GTT ATA CCT    3600
Glu Gly Val Lys Ala Ile Gln Ile Asp Thr Trp Leu Gln Val Ile Pro
1185                   1190                   1195                   1200

CAG CTC ATT GCA AGA ATT GAT ACG CCC AGA CCC TTG GTG GGA CGT CTC    3648
Gln Leu Ile Ala Arg Ile Asp Thr Pro Arg Pro Leu Val Gly Arg Leu
                1205                   1210                   1215

ATT CAC CAG CTT CTC ACA GAC ATT GGT CGG TAC CAC CCC CAG GCC CTC    3696
```

```
Ile His Gln Leu Leu Thr Asp Ile Gly Arg Tyr His Pro Gln Ala Leu
        1220                1225                1230

ATC TAC CCA CTG ACA GTG GCT TCT AAG TCT ACC ACG ACA GCC CGG CAC         3744
Ile Tyr Pro Leu Thr Val Ala Ser Lys Ser Thr Thr Thr Ala Arg His
        1235                1240                1245

AAT GCA GCC AAC AAG ATT CTG AAG AAC ATG TGT GAG CAC AGC AAC ACC         3792
Asn Ala Ala Asn Lys Ile Leu Lys Asn Met Cys Glu His Ser Asn Thr
        1250                1255                1260

CTG GTC CAG CAG GCC ATG ATG GTG AGC GAG GAG CTG ATC CGA GTG GCC         3840
Leu Val Gln Gln Ala Met Met Val Ser Glu Glu Leu Ile Arg Val Ala
1265                1270                1275                1280

ATC CTC TGG CAT GAG ATG TGG CAT GAA GGC TTG GAA GAG GCA TCT CGT         3888
Ile Leu Trp His Glu Met Trp His Glu Gly Leu Glu Glu Ala Ser Arg
                1285                1290                1295

TTG TAC TTT GGG GAA AGG AAC GTG AAA GGC ATG TTT GAG GTG CTG GAG         3936
Leu Tyr Phe Gly Glu Arg Asn Val Lys Gly Met Phe Glu Val Leu Glu
        1300                1305                1310

CCC TTG CAT GCT ATG ATG GAA CGG GGC CCC CAG ACT CTG AAG GAA ACA         3984
Pro Leu His Ala Met Met Glu Arg Gly Pro Gln Thr Leu Lys Glu Thr
        1315                1320                1325

TCC TTT AAT CAG GCC TAT GGT CGA GAT TTA ATG GAG GCC CAA GAG TGG         4032
Ser Phe Asn Gln Ala Tyr Gly Arg Asp Leu Met Glu Ala Gln Glu Trp
        1330                1335                1340

TGC AGG AAG TAC ATG AAA TCA GGG AAT GTC AAG GAC CTC ACC CAA GCC         4080
Cys Arg Lys Tyr Met Lys Ser Gly Asn Val Lys Asp Leu Thr Gln Ala
1345                1350                1355                1360

TGG GAC CTC TAT TAT CAT GTG TTC CGA CGA ATC TCA AAG CAG CTG CCT         4128
Trp Asp Leu Tyr Tyr His Val Phe Arg Arg Ile Ser Lys Gln Leu Pro
                1365                1370                1375

CAG CTC ACA TCC TTA GAG CTG CAA TAT GTT TCC CCA AAA CTT CTG ATG         4176
Gln Leu Thr Ser Leu Glu Leu Gln Tyr Val Ser Pro Lys Leu Leu Met
        1380                1385                1390

TGC CGG GAC CTT GAA TTG GCT GTG CCA GGA ACA TAT GAC CCC AAC CAG         4224
Cys Arg Asp Leu Glu Leu Ala Val Pro Gly Thr Tyr Asp Pro Asn Gln
        1395                1400                1405

CCA ATC ATT CGC ATT CAG TCC ATA GCA CCG TCT TTG CAA GTC ATC ACA         4272
Pro Ile Ile Arg Ile Gln Ser Ile Ala Pro Ser Leu Gln Val Ile Thr
        1410                1415                1420

TCC AAG CAG AGG CCC CGG AAA TTG ACA CTT ATG GGC AGC AAC GGA CAT         4320
Ser Lys Gln Arg Pro Arg Lys Leu Thr Leu Met Gly Ser Asn Gly His
1425                1430                1435                1440

GAG TTT GTT TTC CTT CTA AAA GGC CAT GAA GAT CTG CGC CAG GAT GAG         4368
Glu Phe Val Phe Leu Leu Lys Gly His Glu Asp Leu Arg Gln Asp Glu
                1445                1450                1455

CGT GTG ATG CAG CTC TTC GGC CTG GTT AAC ACC CTT CTG GCC AAT GAC         4416
Arg Val Met Gln Leu Phe Gly Leu Val Asn Thr Leu Leu Ala Asn Asp
        1460                1465                1470

CCA ACA TCT CTT CGG AAA AAC CTC AGC ATC CAG AGA TAC GCT GTC ATC         4464
Pro Thr Ser Leu Arg Lys Asn Leu Ser Ile Gln Arg Tyr Ala Val Ile
        1475                1480                1485

CCT TTA TCG ACC AAC TCG GGC CTC ATT GGC TGG GTT CCC CAC TGT GAC         4512
Pro Leu Ser Thr Asn Ser Gly Leu Ile Gly Trp Val Pro His Cys Asp
        1490                1495                1500

ACA CTG CAC GCC CTC ATC CGG GAC TAC AGG GAG AAG AAG AAG ATC CTT         4560
Thr Leu His Ala Leu Ile Arg Asp Tyr Arg Glu Lys Lys Lys Ile Leu
1505                1510                1515                1520

CTC AAC ATC GAG CAT CGC ATC ATG TTG CGG ATG GCT CCG GAC TAT GAC         4608
Leu Asn Ile Glu His Arg Ile Met Leu Arg Met Ala Pro Asp Tyr Asp
                1525                1530                1535
```

```
CAC TTG ACT CTG ATG CAG AAG GTG GAG GTG TTT GAG CAT GCC GTC AAT        4656
His Leu Thr Leu Met Gln Lys Val Glu Val Phe Glu His Ala Val Asn
             1540                1545                1550

AAT ACA GCT GGG GAC GAC CTG GCC AAG CTG CTG TGG CTG AAA AGC CCC        4704
Asn Thr Ala Gly Asp Asp Leu Ala Lys Leu Leu Trp Leu Lys Ser Pro
        1555                1560                1565

AGC TCC GAG GTG TGG TTT GAC CGA AGA ACC AAT TAT ACC CGT TCT TTA        4752
Ser Ser Glu Val Trp Phe Asp Arg Arg Thr Asn Tyr Thr Arg Ser Leu
        1570                1575                1580

GCG GTC ATG TCA ATG GTT GGG TAT ATT TTA GGC CTG GGA GAT AGA CAC        4800
Ala Val Met Ser Met Val Gly Tyr Ile Leu Gly Leu Gly Asp Arg His
1585                1590                1595                1600

CCA TCC AAC CTG ATG CTG GAC CGT CTG AGT GGG AAG ATC CTG CAC ATT        4848
Pro Ser Asn Leu Met Leu Asp Arg Leu Ser Gly Lys Ile Leu His Ile
                1605                1610                1615

GAC TTT GGG GAC TGC TTT GAG GTT GCT ATG ACC CGA GAG AAG TTT CCA        4896
Asp Phe Gly Asp Cys Phe Glu Val Ala Met Thr Arg Glu Lys Phe Pro
             1620                1625                1630

GAG AAG ATT CCA TTT AGA CTA ACA AGA ATG TTG ACC AAT GCT ATG GAG        4944
Glu Lys Ile Pro Phe Arg Leu Thr Arg Met Leu Thr Asn Ala Met Glu
        1635                1640                1645

GTT ACA GGC CTG GAT GGC AAC TAC AGA ATC ACA TGC CAC ACA GTG ATG        4992
Val Thr Gly Leu Asp Gly Asn Tyr Arg Ile Thr Cys His Thr Val Met
        1650                1655                1660

GAG GTG CTG CGA GAG CAC AAG GAC AGT GTC ATG GCC GTG CTG GAA GCC        5040
Glu Val Leu Arg Glu His Lys Asp Ser Val Met Ala Val Leu Glu Ala
1665                1670                1675                1680

TTT GTC TAT GAC CCC TTG CTG AAC TGG AGG CTG ATG GAC ACA AAT ACC        5088
Phe Val Tyr Asp Pro Leu Leu Asn Trp Arg Leu Met Asp Thr Asn Thr
                1685                1690                1695

AAA GGC AAC AAG CGA TCC CGA ACG AGG ACG GAT TCC TAC TCT GCT GGC        5136
Lys Gly Asn Lys Arg Ser Arg Thr Arg Thr Asp Ser Tyr Ser Ala Gly
            1700                1705                1710

CAG TCA GTC GAA ATT TTG GAC GGT GTG GAA CTT GGA GAG CCA GCC CAT        5184
Gln Ser Val Glu Ile Leu Asp Gly Val Glu Leu Gly Glu Pro Ala His
        1715                1720                1725

AAG AAA ACG GGG ACC ACA GTG CCA GAA TCT ATT CAT TCT TTC ATT GGA        5232
Lys Lys Thr Gly Thr Thr Val Pro Glu Ser Ile His Ser Phe Ile Gly
        1730                1735                1740

GAC GGT TTG GTG AAA CCA GAG GCC CTA AAT AAG AAA GCT ATC CAG ATT        5280
Asp Gly Leu Val Lys Pro Glu Ala Leu Asn Lys Lys Ala Ile Gln Ile
1745                1750                1755                1760

ATT AAC AGG GTT CGA GAT AAG CTC ACT GGT CGG GAC TTC TCT CAT GAT        5328
Ile Asn Arg Val Arg Asp Lys Leu Thr Gly Arg Asp Phe Ser His Asp
                1765                1770                1775

GAC ACT TTG GAT GTT CCA ACG CAA GTT GAG CTG CTC ATC AAA CAA GCG        5376
Asp Thr Leu Asp Val Pro Thr Gln Val Glu Leu Leu Ile Lys Gln Ala
            1780                1785                1790

ACA TCC CAT GAA AAC CTC TGC CAG TGC TAT ATT GGC TGG TGC CCT TTC        5424
Thr Ser His Glu Asn Leu Cys Gln Cys Tyr Ile Gly Trp Cys Pro Phe
        1795                1800                1805

TGG TAA                                                                5430
Trp (2) INFORMATION FOR SEQ ID NO:12:

(i) SEQUENCE CHARACTERISTICS:
        (A) LENGTH: 1809 amino acids
        (B) TYPE: amino acid
        (D) TOPOLOGY: linear
```

(ii) MOLECULE TYPE: protein (xi) SEQUENCE DESCRIPTION: SEQ ID NO:12:

```
Leu Glu His Ser Gly Ile Gly Arg Ile Lys Glu Gln Ser Ala Arg Met
 1               5                  10                  15

Leu Gly His Leu Val Ser Asn Ala Pro Arg Leu Ile Arg Pro Tyr Met
                20                  25                  30

Glu Pro Ile Leu Lys Ala Leu Ile Leu Lys Leu Lys Asp Pro Asp Pro
            35                  40                  45

Asp Pro Asn Pro Gly Val Ile Asn Asn Val Leu Ala Thr Ile Gly Glu
        50                  55                  60

Leu Ala Gln Val Ser Gly Leu Glu Met Arg Lys Trp Val Asp Glu Leu
65                  70                  75                  80

Phe Ile Ile Ile Met Asp Met Leu Gln Asp Ser Ser Leu Leu Ala Lys
                85                  90                  95

Arg Gln Val Ala Leu Trp Thr Leu Gly Gln Leu Val Ala Ser Thr Gly
            100                 105                 110

Tyr Val Val Glu Pro Tyr Arg Lys Tyr Pro Thr Leu Leu Glu Val Leu
        115                 120                 125

Leu Asn Phe Leu Lys Thr Glu Gln Asn Gln Gly Thr Arg Arg Glu Ala
130                 135                 140

Ile Arg Val Leu Gly Leu Leu Gly Ala Leu Asp Pro Tyr Lys His Lys
145                 150                 155                 160

Val Asn Ile Gly Met Ile Asp Gln Ser Arg Asp Ala Ser Ala Val Ser
                165                 170                 175

Leu Ser Glu Ser Lys Ser Ser Gln Asp Ser Ser Asp Tyr Ser Thr Ser
            180                 185                 190

Glu Met Leu Val Asn Met Gly Asn Leu Pro Leu Asp Glu Phe Tyr Pro
        195                 200                 205

Ala Val Ser Met Val Ala Leu Met Arg Ile Phe Arg Asp Gln Ser Leu
            210                 215                 220

Ser His His His Thr Met Val Val Gln Ala Ile Thr Phe Ile Phe Lys
225                 230                 235                 240

Ser Leu Gly Leu Lys Cys Val Gln Phe Leu Pro Gln Val Met Pro Thr
                245                 250                 255

Phe Leu Asn Val Ile Arg Val Cys Asp Gly Ala Ile Arg Glu Phe Leu
                260                 265                 270

Phe Gln Gln Leu Gly Met Leu Val Ser Phe Val Lys Ser His Ile Arg
            275                 280                 285

Pro Tyr Met Asp Glu Ile Val Thr Leu Met Arg Glu Phe Trp Val Met
290                 295                 300

Asn Thr Ser Ile Gln Ser Thr Ile Ile Leu Ile Glu Gln Ile Val
305                 310                 315                 320

Val Ala Leu Gly Gly Glu Phe Lys Leu Tyr Leu Pro Gln Leu Ile Pro
                325                 330                 335

His Met Leu Arg Val Phe Met His Asp Asn Ser Pro Gly Arg Ile Val
            340                 345                 350

Ser Ile Lys Leu Leu Ala Ala Ile Gln Leu Phe Gly Ala Asn Leu Asp
            355                 360                 365

Asp Tyr Leu His Leu Leu Pro Ile Val Lys Leu Phe Asp Ala
        370                 375                 380

Pro Glu Ala Pro Leu Pro Ser Arg Lys Ala Ala Leu Glu Thr Val Asp
385                 390                 395                 400
```

-continued

```
Arg Leu Thr Glu Ser Leu Asp Phe Thr Asp Tyr Ala Ser Arg Ile Ile
            405                 410                 415
His Pro Ile Val Arg Thr Leu Asp Gln Ser Pro Glu Leu Arg Ser Thr
        420                 425                 430
Ala Met Asp Thr Leu Ser Ser Leu Val Phe Gln Leu Gly Lys Lys Tyr
    435                 440                 445
Gln Ile Phe Ile Pro Met Val Asn Lys Val Leu Val Arg His Arg Ile
450                 455                 460
Asn His Gln Arg Tyr Asp Val Leu Ile Cys Arg Ile Val Lys Gly Tyr
465                 470                 475                 480
Thr Leu Ala Asp Glu Glu Asp Pro Leu Ile Tyr Gln His Arg Met
                485                 490                 495
Leu Arg Ser Gly Gln Gly Asp Ala Leu Ala Ser Gly Pro Val Glu Thr
            500                 505                 510
Gly Pro Met Lys Lys Leu His Val Ser Thr Ile Asn Leu Gln Lys Ala
        515                 520                 525
Trp Gly Ala Ala Arg Arg Val Ser Lys Asp Asp Trp Leu Glu Trp Leu
    530                 535                 540
Arg Arg Leu Ser Leu Glu Leu Leu Lys Asp Ser Ser Pro Ser Leu
545                 550                 555                 560
Arg Ser Cys Trp Ala Leu Ala Gln Ala Tyr Asn Pro Met Ala Arg Asp
                565                 570                 575
Leu Phe Asn Ala Ala Phe Val Ser Cys Trp Ser Glu Leu Asn Glu Asp
            580                 585                 590
Gln Gln Asp Glu Leu Ile Arg Ser Ile Glu Leu Ala Leu Thr Ser Gln
        595                 600                 605
Asp Ile Ala Glu Val Thr Gln Thr Leu Leu Asn Leu Ala Glu Phe Met
    610                 615                 620
Glu His Ser Asp Lys Gly Pro Leu Pro Leu Arg Asp Asp Asn Gly Ile
625                 630                 635                 640
Val Leu Leu Gly Glu Arg Ala Ala Lys Cys Arg Ala Tyr Ala Lys Ala
                645                 650                 655
Leu His Tyr Lys Glu Leu Glu Phe Gln Lys Gly Pro Thr Pro Ala Ile
            660                 665                 670
Leu Glu Ser Leu Ile Ser Ile Asn Asn Lys Leu Gln Gln Pro Glu Ala
        675                 680                 685
Ala Ala Gly Val Leu Glu Tyr Ala Met Lys His Phe Gly Glu Leu Glu
    690                 695                 700
Ile Gln Ala Thr Trp Tyr Glu Lys Leu His Glu Trp Glu Asp Ala Leu
705                 710                 715                 720
Val Ala Tyr Asp Lys Lys Met Asp Thr Asn Lys Asp Pro Glu Leu
                725                 730                 735
Met Leu Gly Arg Met Arg Cys Leu Glu Ala Leu Gly Glu Trp Gly Gln
            740                 745                 750
Leu His Gln Gln Cys Cys Glu Lys Trp Thr Leu Val Asn Asp Glu Thr
        755                 760                 765
Gln Ala Lys Met Ala Arg Met Ala Ala Ala Ala Trp Gly Leu Gly
    770                 775                 780
Gln Trp Asp Ser Met Glu Glu Tyr Thr Cys Met Ile Pro Arg Asp Thr
785                 790                 795                 800
His Asp Gly Ala Phe Tyr Arg Ala Val Leu Ala Leu His Gln Asp Leu
                805                 810                 815
Phe Ser Leu Ala Gln Gln Cys Ile Asp Lys Ala Arg Asp Leu Leu Asp
```

-continued

```
                820             825             830
Ala Glu Leu Thr Ala Met Ala Gly Glu Ser Tyr Ser Arg Ala Tyr Gly
            835             840             845

Ala Met Val Ser Cys His Met Leu Ser Glu Leu Glu Val Ile Gln
850             855             860

Tyr Lys Leu Val Pro Glu Arg Glu Ile Ile Arg Gln Ile Trp Trp
865             870             875             880

Glu Arg Leu Gln Gly Cys Gln Arg Ile Val Glu Asp Trp Gln Lys Ile
            885             890             895

Leu Met Val Arg Ser Leu Val Val Ser Pro His Glu Asp Met Arg Thr
            900             905             910

Trp Leu Lys Tyr Ala Ser Leu Cys Gly Lys Ser Gly Arg Leu Ala Leu
            915             920             925

Ala His Lys Thr Leu Val Leu Leu Gly Val Asp Pro Ser Arg Gln
            930             935             940

Leu Asp His Pro Leu Pro Thr Val His Pro Gln Val Thr Tyr Ala Tyr
945             950             955             960

Met Lys Asn Met Trp Lys Ser Ala Arg Lys Ile Asp Ala Phe Gln His
            965             970             975

Met Gln His Phe Val Gln Thr Met Gln Gln Ala Gln His Ala Ile
            980             985             990

Ala Thr Glu Asp Gln Gln His Lys Gln Glu Leu His Lys Leu Met Ala
            995             1000            1005

Arg Cys Phe Leu Lys Leu Gly Glu Trp Gln Leu Asn Leu Gln Gly Ile
            1010            1015            1020

Asn Glu Ser Thr Ile Pro Lys Val Leu Gln Tyr Tyr Ser Ala Ala Thr
1025            1030            1035            1040

Glu His Asp Arg Ser Trp Tyr Lys Ala Trp His Ala Trp Ala Val Met
            1045            1050            1055

Asn Phe Glu Ala Val Leu His Tyr Lys His Gln Asn Gln Ala Arg Asp
            1060            1065            1070

Glu Lys Lys Lys Leu Arg His Ala Ser Gly Ala Asn Ile Thr Asn Ala
            1075            1080            1085

Thr Thr Ala Ala Thr Thr Ala Ala Thr Ala Thr Thr Ala Ser Thr
            1090            1095            1100

Glu Gly Ser Asn Ser Glu Ser Glu Ala Glu Ser Thr Glu Asn Ser Pro
1105            1110            1115            1120

Thr Pro Ser Pro Leu Gln Lys Lys Val Thr Glu Asp Leu Ser Lys Thr
            1125            1130            1135

Leu Leu Met Tyr Thr Val Pro Ala Val Gln Gly Phe Phe Arg Ser Ile
            1140            1145            1150

Ser Leu Ser Arg Gly Asn Asn Leu Gln Asp Thr Leu Arg Val Leu Thr
            1155            1160            1165

Leu Trp Phe Asp Tyr Gly His Trp Pro Asp Val Asn Glu Ala Leu Val
            1170            1175            1180

Glu Gly Val Lys Ala Ile Gln Ile Asp Thr Trp Leu Gln Val Ile Pro
1185            1190            1195            1200

Gln Leu Ile Ala Arg Ile Asp Thr Pro Arg Pro Leu Val Gly Arg Leu
            1205            1210            1215

Ile His Gln Leu Leu Thr Asp Ile Gly Arg Tyr His Pro Gln Ala Leu
            1220            1225            1230

Ile Tyr Pro Leu Thr Val Ala Ser Lys Ser Thr Thr Thr Ala Arg His
            1235            1240            1245
```

-continued

Asn Ala Ala Asn Lys Ile Leu Lys Asn Met Cys Glu His Ser Asn Thr
    1250                1255                1260
Leu Val Gln Gln Ala Met Met Val Ser Glu Glu Leu Ile Arg Val Ala
1265            1270                1275                1280
Ile Leu Trp His Glu Met Trp His Glu Gly Leu Glu Glu Ala Ser Arg
                1285                1290                1295
Leu Tyr Phe Gly Glu Arg Asn Val Lys Gly Met Phe Glu Val Leu Glu
            1300                1305                1310
Pro Leu His Ala Met Met Glu Arg Gly Pro Gln Thr Leu Lys Glu Thr
        1315                1320                1325
Ser Phe Asn Gln Ala Tyr Gly Arg Asp Leu Met Glu Ala Gln Glu Trp
    1330                1335                1340
Cys Arg Lys Tyr Met Lys Ser Gly Asn Val Lys Asp Leu Thr Gln Ala
1345            1350                1355                1360
Trp Asp Leu Tyr Tyr His Val Phe Arg Arg Ile Ser Lys Gln Leu Pro
                1365                1370                1375
Gln Leu Thr Ser Leu Glu Leu Gln Tyr Val Ser Pro Lys Leu Leu Met
            1380                1385                1390
Cys Arg Asp Leu Glu Leu Ala Val Pro Gly Thr Tyr Asp Pro Asn Gln
        1395                1400                1405
Pro Ile Ile Arg Ile Gln Ser Ile Ala Pro Ser Leu Gln Val Ile Thr
    1410                1415                1420
Ser Lys Gln Arg Pro Arg Lys Leu Thr Leu Met Gly Ser Asn Gly His
1425            1430                1435                1440
Glu Phe Val Phe Leu Leu Lys Gly His Glu Asp Leu Arg Gln Asp Glu
                1445                1450                1455
Arg Val Met Gln Leu Phe Gly Leu Val Asn Thr Leu Leu Ala Asn Asp
            1460                1465                1470
Pro Thr Ser Leu Arg Lys Asn Leu Ser Ile Gln Arg Tyr Ala Val Ile
        1475                1480                1485
Pro Leu Ser Thr Asn Ser Gly Leu Ile Gly Trp Val Pro His Cys Asp
    1490                1495                1500
Thr Leu His Ala Leu Ile Arg Asp Tyr Arg Glu Lys Lys Lys Ile Leu
1505            1510                1515                1520
Leu Asn Ile Glu His Arg Ile Met Leu Arg Met Ala Pro Asp Tyr Asp
                1525                1530                1535
His Leu Thr Leu Met Gln Lys Val Glu Val Phe Glu His Ala Val Asn
            1540                1545                1550
Asn Thr Ala Gly Asp Asp Leu Ala Lys Leu Leu Trp Leu Lys Ser Pro
        1555                1560                1565
Ser Ser Glu Val Trp Phe Asp Arg Arg Thr Asn Tyr Thr Arg Ser Leu
    1570                1575                1580
Ala Val Met Ser Met Val Gly Tyr Ile Leu Gly Leu Gly Asp Arg His
1585            1590                1595                1600
Pro Ser Asn Leu Met Leu Asp Arg Leu Ser Gly Lys Ile Leu His Ile
                1605                1610                1615
Asp Phe Gly Asp Cys Phe Glu Val Ala Met Thr Arg Glu Lys Phe Pro
            1620                1625                1630
Glu Lys Ile Pro Phe Arg Leu Thr Arg Met Leu Thr Asn Ala Met Glu
        1635                1640                1645
Val Thr Gly Leu Asp Gly Asn Tyr Arg Ile Thr Cys His Thr Val Met
    1650                1655                1660

```
Glu Val Leu Arg Glu His Lys Asp Ser Val Met Ala Val Leu Glu Ala
1665                1670                1675                1680

Phe Val Tyr Asp Pro Leu Leu Asn Trp Arg Leu Met Asp Thr Asn Thr
            1685                1690                1695

Lys Gly Asn Lys Arg Ser Arg Thr Arg Thr Asp Ser Tyr Ser Ala Gly
                1700                1705                1710

Gln Ser Val Glu Ile Leu Asp Gly Val Glu Leu Gly Glu Pro Ala His
        1715                1720                1725

Lys Lys Thr Gly Thr Thr Val Pro Glu Ser Ile His Ser Phe Ile Gly
    1730                1735                1740

Asp Gly Leu Val Lys Pro Glu Ala Leu Asn Lys Lys Ala Ile Gln Ile
1745                1750                1755                1760

Ile Asn Arg Val Arg Asp Lys Leu Thr Gly Arg Asp Phe Ser His Asp
                1765                1770                1775

Asp Thr Leu Asp Val Pro Thr Gln Val Glu Leu Leu Ile Lys Gln Ala
            1780                1785                1790

Thr Ser His Glu Asn Leu Cys Gln Cys Tyr Ile Gly Trp Cys Pro Phe
        1795                1800                1805

Trp
```

(2) INFORMATION FOR SEQ ID NO:13:

(i) SEQUENCE CHARACTERISTICS:
        (A) LENGTH: 1794 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1686

(xi) SEQUENCE DESCRIPTION: SEQ ID NO:13:

```
TTG GTT TAC CCT TTG ACA GTT GCT ATT ACT TCC GAA TCA ACG AGC CGT        48
Leu Val Tyr Pro Leu Thr Val Ala Ile Thr Ser Glu Ser Thr Ser Arg
  1               5                  10                  15

AAA AAG GCA GCT CAA TCC ATT ATT GAA AAA ATG CGA GTA CAT TCT CCT        96
Lys Lys Ala Ala Gln Ser Ile Ile Glu Lys Met Arg Val His Ser Pro
             20                  25                  30

AGC TTG GTG GAT CAA GCA GAA TTA GTG AGT CGA GAA CTC ATC CGA GTT       144
Ser Leu Val Asp Gln Ala Glu Leu Val Ser Arg Glu Leu Ile Arg Val
         35                  40                  45

GCA GTT TTA TGG CAC GAA CAA TGG CAC GAT GCT TTG GAA GAT GCT AGC       192
Ala Val Leu Trp His Glu Gln Trp His Asp Ala Leu Glu Asp Ala Ser
     50                  55                  60

AGG TTT TTC TTT GGT GAA CAC AAC ACA GAA AAG ATG TTT GAA ACA TTG       240
Arg Phe Phe Phe Gly Glu His Asn Thr Glu Lys Met Phe Glu Thr Leu
 65                  70                  75                  80

GAA CCA TTA CAT CAA ATG TTG CAA AAG GGA CCA GAA ACG ATG AGG GAA       288
Glu Pro Leu His Gln Met Leu Gln Lys Gly Pro Glu Thr Met Arg Glu
                 85                  90                  95

CAA GCC TTT GCA AAT GCT TTT GGC AGG GAG TTG ACA GAT GCA TAC GAG       336
Gln Ala Phe Ala Asn Ala Phe Gly Arg Glu Leu Thr Asp Ala Tyr Glu
            100                 105                 110

TGG GTG CTC AAC TTT AGA AGA ACT AAA GAC ATA ACC AAT TTG AAT CAA       384
Trp Val Leu Asn Phe Arg Arg Thr Lys Asp Ile Thr Asn Leu Asn Gln
        115                 120                 125

GCA TGG GAT ATA TAC TAC AAT GTC TTT AGA AGA GTA AGC AAA CAG GTG       432
```

-continued

```
Ala Trp Asp Ile Tyr Tyr Asn Val Phe Arg Arg Val Ser Lys Gln Val
        130                 135                 140

CAG CTG TTA GCT AGT CTT GAG TTG CAG TAT GTA TCT CCG GAC TTA GAG      480
Gln Leu Leu Ala Ser Leu Glu Leu Gln Tyr Val Ser Pro Asp Leu Glu
145                 150                 155                 160

CAT GCT CAA GAT TTG GAA TTG GCT GTA CCA GGT ACT TAC CAA GCA GGC      528
His Ala Gln Asp Leu Glu Leu Ala Val Pro Gly Thr Tyr Gln Ala Gly
                165                 170                 175

AAA CCT GTG ATC AGA ATA ATC AAA TTT GAT CCT ACT TTT TCG ATT ATT      576
Lys Pro Val Ile Arg Ile Ile Lys Phe Asp Pro Thr Phe Ser Ile Ile
                180                 185                 190

TCA TCT AAA CAA AGA CCG AGA AAA TTA TCG TGC AGA GGA AGT GAT GGT      624
Ser Ser Lys Gln Arg Pro Arg Lys Leu Ser Cys Arg Gly Ser Asp Gly
                195                 200                 205

AAA GAC TAC CAA TAT GCG TTG AAA GGA CAT GAA GAT ATC AGA CAA GAT      672
Lys Asp Tyr Gln Tyr Ala Leu Lys Gly His Glu Asp Ile Arg Gln Asp
210                 215                 220

AAC TTA GTG ATG CAA TTG TTT GGT TTG GTT AAT ACG TTG TTG GTA AAT      720
Asn Leu Val Met Gln Leu Phe Gly Leu Val Asn Thr Leu Leu Val Asn
225                 230                 235                 240

GAT CCG GTA TGT TTC AAG AGA CAT TTG GAT ATA CAA CAA TAT CCT GCT      768
Asp Pro Val Cys Phe Lys Arg His Leu Asp Ile Gln Gln Tyr Pro Ala
                245                 250                 255

ATT CCA TTA TCA CCA AAA GTG GGA TTG CTT GGT TGG GTT CCA AAT AGT      816
Ile Pro Leu Ser Pro Lys Val Gly Leu Leu Gly Trp Val Pro Asn Ser
                260                 265                 270

GAC ACT TTC CAT GTA TTG ATC AAA GGC TAT CGC GAA TCA AGA AGT ATA      864
Asp Thr Phe His Val Leu Ile Lys Gly Tyr Arg Glu Ser Arg Ser Ile
                275                 280                 285

ATG TTG AAT ATT GAA CAC AGG CTT TTG TTG CAA ATG GCA CCT GAT TAT      912
Met Leu Asn Ile Glu His Arg Leu Leu Leu Gln Met Ala Pro Asp Tyr
290                 295                 300

GAT TTC TTG ACA TTA TTG CAA AAA GTT GAA GTG TTC ACA AGT GCA ATG      960
Asp Phe Leu Thr Leu Leu Gln Lys Val Glu Val Phe Thr Ser Ala Met
305                 310                 315                 320

GAT AAT TGT AAG GGA CAG GAT TTG TAC AAA GTG TTA TGG CTC AAA TCT     1008
Asp Asn Cys Lys Gly Gln Asp Leu Tyr Lys Val Leu Trp Leu Lys Ser
                325                 330                 335

AAA TCA TCC GAG GCG TGG TTG GAC CGT AGA ACA ACA TAC ACG AGA TCA     1056
Lys Ser Ser Glu Ala Trp Leu Asp Arg Arg Thr Thr Tyr Thr Arg Ser
                340                 345                 350

TTA GCT GTA ATG TCT ATG GTT GGG TAT ATA TTA GGT TTG GGG GAT AGG     1104
Leu Ala Val Met Ser Met Val Gly Tyr Ile Leu Gly Leu Gly Asp Arg
                355                 360                 365

CAC CCA TCA AAT TTG ATG TTG GAC CGT ATT ACT GGG AAA GTC ATC CAT     1152
His Pro Ser Asn Leu Met Leu Asp Arg Ile Thr Gly Lys Val Ile His
370                 375                 380

ATT GAT TTC GGA GAC TGT TTT GAA GCA GCA ATA TTA CGT GAG AAG TAT     1200
Ile Asp Phe Gly Asp Cys Phe Glu Ala Ala Ile Leu Arg Glu Lys Tyr
385                 390                 395                 400

CCA GAG AGA GTT CCG TTT AGA TTG ACG AGA ATG CTT AAT TAT GCC ATG     1248
Pro Glu Arg Val Pro Phe Arg Leu Thr Arg Met Leu Asn Tyr Ala Met
                405                 410                 415

GAA GTT AGT GGA ATA GAG GGC TCG TTC AGA ATC ACA TGT GAA CAT GTT     1296
Glu Val Ser Gly Ile Glu Gly Ser Phe Arg Ile Thr Cys Glu His Val
                420                 425                 430

ATG AGG GTG TTG CGT GAT AAT AAA GAG TCT TTA ATG GCA ATA TTA GAG     1344
Met Arg Val Leu Arg Asp Asn Lys Glu Ser Leu Met Ala Ile Leu Glu
                435                 440                 445
```

```
GCC TTT GCT TAC GAT CCC TTG ATA AAT TGG GGG TTT GAT TTC CCA ACA    1392
Ala Phe Ala Tyr Asp Pro Leu Ile Asn Trp Gly Phe Asp Phe Pro Thr
    450                 455                 460

AAG GCG TTG GCT GAA TCA ACG GGT ATA CGT GTT CCA CAA GTC AAC ACT    1440
Lys Ala Leu Ala Glu Ser Thr Gly Ile Arg Val Pro Gln Val Asn Thr
465                 470                 475                 480

GCA GAA TTA TTA CGC AGA GGA CAG ATT GAC GAA AAA GAA GCT GTA AGA    1488
Ala Glu Leu Leu Arg Arg Gly Gln Ile Asp Glu Lys Glu Ala Val Arg
                    485                 490                 495

TTG CAA AAG CAA AAT GAA TTG GAA ATA AGA AAC GCT AGA GCT GCA TTA    1536
Leu Gln Lys Gln Asn Glu Leu Glu Ile Arg Asn Ala Arg Ala Ala Leu
                500                 505                 510

GTG TTG AAA CGT ATT ACC GAT AAG TTA ACT GGT AAC GAT ATC AAA CGG    1584
Val Leu Lys Arg Ile Thr Asp Lys Leu Thr Gly Asn Asp Ile Lys Arg
            515                 520                 525

TTG AGA GGA TTA GAT GTG CCT ACT CAA GTC GAT AAA TTG ATT CAA CAA    1632
Leu Arg Gly Leu Asp Val Pro Thr Gln Val Asp Lys Leu Ile Gln Gln
        530                 535                 540

GCC ACC AGT GTT GAG AAT TTG TGT CAG CAT TAC ATT GGT TGG TGT TCG    1680
Ala Thr Ser Val Glu Asn Leu Cys Gln His Tyr Ile Gly Trp Cys Ser
545                 550                 555                 560

TGT TGG TAGGTTGATT ATCGTCATGT GTCGATAAGT ATGGTATTGT GGTAACTATT     1736
Cys Trp
TTATAAAGGG AAATATTAAA GAATTGTATA TTATTAAAAA AAAAAAAAAA AACTCGAG    1794

(2) INFORMATION FOR SEQ ID NO:14:

(i) SEQUENCE CHARACTERISTICS:
        (A) LENGTH: 562 amino acids
        (B) TYPE: amino acid
        (D) TOPOLOGY: linear (ii) MOLECULE TYPE: protein (xi) SEQUENCE DESCRIPTION: SEQ ID NO:14:

Leu Val Tyr Pro Leu Thr Val Ala Ile Thr Ser Glu Ser Thr Ser Arg
  1               5                  10                  15

Lys Lys Ala Ala Gln Ser Ile Ile Glu Lys Met Arg Val His Ser Pro
             20                  25                  30

Ser Leu Val Asp Gln Ala Glu Leu Val Ser Arg Glu Leu Ile Arg Val
         35                  40                  45

Ala Val Leu Trp His Glu Gln Trp His Asp Ala Leu Glu Asp Ala Ser
     50                  55                  60

Arg Phe Phe Phe Gly Glu His Asn Thr Glu Lys Met Phe Glu Thr Leu
 65                  70                  75                  80

Glu Pro Leu His Gln Met Leu Gln Lys Gly Pro Glu Thr Met Arg Glu
                 85                  90                  95

Gln Ala Phe Ala Asn Ala Phe Gly Arg Glu Leu Thr Asp Ala Tyr Glu
            100                 105                 110

Trp Val Leu Asn Phe Arg Arg Thr Lys Asp Ile Thr Asn Leu Asn Gln
        115                 120                 125

Ala Trp Asp Ile Tyr Tyr Asn Val Phe Arg Arg Val Ser Lys Gln Val
    130                 135                 140

Gln Leu Leu Ala Ser Leu Glu Leu Gln Tyr Val Ser Pro Asp Leu Glu
145                 150                 155                 160

His Ala Gln Asp Leu Glu Leu Ala Val Pro Gly Thr Tyr Gln Ala Gly
                165                 170                 175

Lys Pro Val Ile Arg Ile Ile Lys Phe Asp Pro Thr Phe Ser Ile Ile
            180                 185                 190
```

```
Ser Ser Lys Gln Arg Pro Arg Lys Leu Ser Cys Arg Gly Ser Asp Gly
        195                 200                 205

Lys Asp Tyr Gln Tyr Ala Leu Lys Gly His Glu Asp Ile Arg Gln Asp
        210                 215                 220

Asn Leu Val Met Gln Leu Phe Gly Leu Val Asn Thr Leu Leu Val Asn
225                 230                 235                 240

Asp Pro Val Cys Phe Lys Arg His Leu Asp Ile Gln Gln Tyr Pro Ala
                245                 250                 255

Ile Pro Leu Ser Pro Lys Val Gly Leu Leu Gly Trp Val Pro Asn Ser
                260                 265                 270

Asp Thr Phe His Val Leu Ile Lys Gly Tyr Arg Glu Ser Arg Ser Ile
        275                 280                 285

Met Leu Asn Ile Glu His Arg Leu Leu Gln Met Ala Pro Asp Tyr
290                 295                 300

Asp Phe Leu Thr Leu Leu Gln Lys Val Glu Val Phe Thr Ser Ala Met
305                 310                 315                 320

Asp Asn Cys Lys Gly Gln Asp Leu Tyr Lys Val Leu Trp Leu Lys Ser
                325                 330                 335

Lys Ser Ser Glu Ala Trp Leu Asp Arg Arg Thr Thr Tyr Thr Arg Ser
        340                 345                 350

Leu Ala Val Met Ser Met Val Gly Tyr Ile Leu Gly Leu Gly Asp Arg
        355                 360                 365

His Pro Ser Asn Leu Met Leu Asp Arg Ile Thr Gly Lys Val Ile His
        370                 375                 380

Ile Asp Phe Gly Asp Cys Phe Glu Ala Ala Ile Leu Arg Glu Lys Tyr
385                 390                 395                 400

Pro Glu Arg Val Pro Phe Arg Leu Thr Arg Met Leu Asn Tyr Ala Met
                405                 410                 415

Glu Val Ser Gly Ile Glu Gly Ser Phe Arg Ile Thr Cys Glu His Val
                420                 425                 430

Met Arg Val Leu Arg Asp Asn Lys Glu Ser Leu Met Ala Ile Leu Glu
        435                 440                 445

Ala Phe Ala Tyr Asp Pro Leu Ile Asn Trp Gly Phe Asp Phe Pro Thr
450                 455                 460

Lys Ala Leu Ala Glu Ser Thr Gly Ile Arg Val Pro Gln Val Asn Thr
465                 470                 475                 480

Ala Glu Leu Leu Arg Arg Gly Gln Ile Asp Glu Lys Glu Ala Val Arg
                485                 490                 495

Leu Gln Lys Gln Asn Glu Leu Glu Ile Arg Asn Ala Arg Ala Ala Leu
        500                 505                 510

Val Leu Lys Arg Ile Thr Asp Lys Leu Thr Gly Asn Asp Ile Lys Arg
        515                 520                 525

Leu Arg Gly Leu Asp Val Pro Thr Gln Val Asp Lys Leu Ile Gln Gln
        530                 535                 540

Ala Thr Ser Val Glu Asn Leu Cys Gln His Tyr Ile Gly Trp Cys Ser
545                 550                 555                 560

Cys Trp (2) INFORMATION FOR SEQ ID NO:15:

(i) SEQUENCE CHARACTERISTICS:
        (A) LENGTH: 399 base pairs
        (B) TYPE: nucleic acid
        (C) STRANDEDNESS: single
```

(D) TOPOLOGY: linear (ii) MOLECULE TYPE: cDNA (ix) FEATURE:
        (A) NAME/KEY: CDS
        (B) LOCATION: 1..399

(xi) SEQUENCE DESCRIPTION: SEQ ID NO:15:

```
GTT AGT CAC GAG TTG ATC AGA GTA GCC GTT CTA TGG CAC GAA TTA TGG      48
Val Ser His Glu Leu Ile Arg Val Ala Val Leu Trp His Glu Leu Trp
 1               5                  10                  15

TAT GAA GGA CTG GAA GAT GCG AGC CGC CAA TTT TTC GTT GAA CAT AAC      96
Tyr Glu Gly Leu Glu Asp Ala Ser Arg Gln Phe Phe Val Glu His Asn
                20                  25                  30

ATA GAA AAA ATG TTT TCT ACT TTA GAA CCT TTA CAT AAA CAC TTA GGC     144
Ile Glu Lys Met Phe Ser Thr Leu Glu Pro Leu His Lys His Leu Gly
             35                  40                  45

AAT GAG CCT CAA ACG TTA AGT GAG GTA TCG TTT CAG AAA TCA TTT GGT     192
Asn Glu Pro Gln Thr Leu Ser Glu Val Ser Phe Gln Lys Ser Phe Gly
 50                  55                  60

AGA GAT TTG AAC GAT GCC TAC GAA TGG TTG AAT AAC TAC AAA AAG TCA     240
Arg Asp Leu Asn Asp Ala Tyr Glu Trp Leu Asn Asn Tyr Lys Lys Ser
 65                  70                  75                  80

AAA GAC ATC AAT AAT TTG AAC CAA GCT TGG GAT ATT TAT TAT AAC GTC     288
Lys Asp Ile Asn Asn Leu Asn Gln Ala Trp Asp Ile Tyr Tyr Asn Val
                 85                  90                  95

TTC AGA AAA ATA ACA CGT CAA ATA CCA CAG TTA CAA ACC TTA GAC TTA     336
Phe Arg Lys Ile Thr Arg Gln Ile Pro Gln Leu Gln Thr Leu Asp Leu
                100                 105                 110

CAG CAT GTT TCT CCC CAG CTT CTG GCT ACT CAT GAT CTC GAA TTG GCT     384
Gln His Val Ser Pro Gln Leu Leu Ala Thr His Asp Leu Glu Leu Ala
            115                 120                 125

GTT CCT GGG ACA TAT                                                 399
Val Pro Gly Thr Tyr
        130
```

(2) INFORMATION FOR SEQ ID NO:16:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO:16:

```
Val Ser His Glu Leu Ile Arg Val Ala Val Leu Trp His Glu Leu Trp
 1               5                  10                  15

Tyr Glu Gly Leu Glu Asp Ala Ser Arg Gln Phe Phe Val Glu His Asn
                20                  25                  30

Ile Glu Lys Met Phe Ser Thr Leu Glu Pro Leu His Lys His Leu Gly
             35                  40                  45

Asn Glu Pro Gln Thr Leu Ser Glu Val Ser Phe Gln Lys Ser Phe Gly
 50                  55                  60

Arg Asp Leu Asn Asp Ala Tyr Glu Trp Leu Asn Asn Tyr Lys Lys Ser
 65                  70                  75                  80

Lys Asp Ile Asn Asn Leu Asn Gln Ala Trp Asp Ile Tyr Tyr Asn Val
                 85                  90                  95

Phe Arg Lys Ile Thr Arg Gln Ile Pro Gln Leu Gln Thr Leu Asp Leu
                100                 105                 110
```

```
Gln His Val Ser Pro Gln Leu Leu Ala Thr His Asp Leu Glu Leu Ala
    115                 120                 125

Val Pro Gly Thr Tyr
    130
```

(2) INFORMATION FOR SEQ ID NO:17:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..399

(xi) SEQUENCE DESCRIPTION: SEQ ID NO:17:

```
GTC AGC CAC GAA TTG ATA CGT ATG GCG GTG CTT TGG CAT GAG CAA TGG      48
Val Ser His Glu Leu Ile Arg Met Ala Val Leu Trp His Glu Gln Trp
 1               5                  10                  15

TAT GAG GGT CTG GAT GAC GCC AGT AGG CAG TTT TTT GGA GAA CAT AAT      96
Tyr Glu Gly Leu Asp Asp Ala Ser Arg Gln Phe Phe Gly Glu His Asn
            20                  25                  30

ACC GAA AAA ATG TTT GCT GCT TTA GAG CCT CTG TAC GAA ATG CTG AAG     144
Thr Glu Lys Met Phe Ala Ala Leu Glu Pro Leu Tyr Glu Met Leu Lys
        35                  40                  45

AGA GGA CCG GAA ACT TTG AGG GAA ATA TCG TTC CAA AAT TCT TTT GGT     192
Arg Gly Pro Glu Thr Leu Arg Glu Ile Ser Phe Gln Asn Ser Phe Gly
    50                  55                  60

AGG GAC TTG AAT GAC GCT TAC GAA TGG CTG ATG AAT TAC AAA AAA TCT     240
Arg Asp Leu Asn Asp Ala Tyr Glu Trp Leu Met Asn Tyr Lys Lys Ser
 65                  70                  75                  80

AAA GAT GTT AGT AAT TTA AAC CAA GCG TGG GAC ATT TAC TAT AAT GTT     288
Lys Asp Val Ser Asn Leu Asn Gln Ala Trp Asp Ile Tyr Tyr Asn Val
                85                  90                  95

TTC AGG AAA ATT GGT AAA CAG TTG CCA CAA TTA CAA ACT CTT GAA CTA     336
Phe Arg Lys Ile Gly Lys Gln Leu Pro Gln Leu Gln Thr Leu Glu Leu
            100                 105                 110

CAA CAT GTG TCG CCA AAA CTA CTA TCT GCG CAT GAT TTG GAA TTG GCT     384
Gln His Val Ser Pro Lys Leu Leu Ser Ala His Asp Leu Glu Leu Ala
        115                 120                 125

GTC CCC GGG ACC CGT                                                 399
Val Pro Gly Thr Arg
    130
```

(2) INFORMATION FOR SEQ ID NO:18:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO:18:

```
Val Ser His Glu Leu Ile Arg Met Ala Val Leu Trp His Glu Gln Trp
 1               5                  10                  15

Tyr Glu Gly Leu Asp Asp Ala Ser Arg Gln Phe Phe Gly Glu His Asn
            20                  25                  30

Thr Glu Lys Met Phe Ala Ala Leu Glu Pro Leu Tyr Glu Met Leu Lys
        35                  40                  45
```

```
Arg Gly Pro Glu Thr Leu Arg Glu Ile Ser Phe Gln Asn Ser Phe Gly
         50                  55                  60

Arg Asp Leu Asn Asp Ala Tyr Glu Trp Leu Met Asn Tyr Lys Lys Ser
 65                  70                  75                  80

Lys Asp Val Ser Asn Leu Asn Gln Ala Trp Asp Ile Tyr Tyr Asn Val
                 85                  90                  95

Phe Arg Lys Ile Gly Lys Gln Leu Pro Gln Leu Gln Thr Leu Glu Leu
                100                 105                 110

Gln His Val Ser Pro Lys Leu Leu Ser Ala His Asp Leu Glu Leu Ala
             115                 120                 125

Val Pro Gly Thr Arg
        130
```

(2) INFORMATION FOR SEQ ID NO:19:

(i) SEQUENCE CHARACTERISTICS:
        (A) LENGTH: 531 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:19:

```
TGACCCTCAC CCCTTCCACC TATCCCAAAA ACCTCACTGG GTCTGTGGAC AAACAACANA    60

AATNTTTTCC ANANAGGCCC CAAATGAGNC CCANGGGTCT NTCTTCCATC AGACCCAGTG   120

ATTCTGCGAC TCACACNCTT CAATTCAAGA CCTGACCNCT AGTAGGGAGG TTTANTCAGA   180

TCGCTGGCAN CCTCGGCTGA NCAGATNCAN AGNGGGGNTC GCTGTTCAGT GGGNCCACCC   240

TCNCTGGCCT TCTTCANCAG GGGTCTGGGA TGTTTTCAGT GGNCCNAANA CNCTGTTTAG   300

AGCCAGGGCT CAGNAAACAG AAAANCTNTC ATGGNGGTTC TGGACACAGG GNAGGTCTGG   360

NACATATTGG GGATTATGAN CAGNACCAAN ACNCCACTAA ATNCCCCAAG NANAAAGTGT   420

AACCATNTCT ANACNCCATN TTNTATCAGN ANAAATTTTN TTCCNATAAA TGACATCAGN   480

ANTTTNAACA TNAAAAAAAA AAAAAAAAA AAAANAAAAA AAAAAAAAAA A            531
```

(2) INFORMATION FOR SEQ ID NO:20:

(i) SEQUENCE CHARACTERISTICS:
        (A) LENGTH: 231 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: misc_feature
        (B) LOCATION: 128
        (D) OTHER INFORMATION: /label= XhoI (xi) SEQUENCE DESCRIPTION: SEQ ID NO:20:

```
GCGTATAACG CGTTTGGAAT CACTACAGGG ATGTTTAATA CCACTACAAT GGATGATGTA    60

TATAACTATC TATTCGATGA TGAAGATACC CCACCAAACC CAAAAAAAGA GATCTGGAAT   120

TCGGATCCTC GAGAGATCTA TGAATCGTAG ATACTGAAAA ACCCCGCAAG TTCACTTCAA   180

CTGTGCATCG TGCACCATCT CAATTTCTTT CATTTATACA TCGTTTTGCC T            231
```

(2) INFORMATION FOR SEQ ID NO:21:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:21:

TGAAGATACC CCACCAAACC C                                             21

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:22:

TGCACAGTTG AAGTGAAC                                                 18

(2) INFORMATION FOR SEQ ID NO:23:

(i) SEQUENCE CHARACTERISTICS:
        (A) LENGTH: 662 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 60..416

(xi) SEQUENCE DESCRIPTION: SEQ ID NO:23:

ACCAAACCCA AAAAAGAGA TCCTAGNAAC TAGTGGATCC CCCGGGCTGC AGGAATTCG       59

GTA CGA GTC GCC CTC AGC AGA CTC GCC CAG GAG AGG AAA GCA TGG AGG      107
Val Arg Val Ala Leu Ser Arg Leu Ala Gln Glu Arg Lys Ala Trp Arg
 1               5                  10                  15

AAA GAC CAC CCA TTT GGT TTC GTG GCT GTC CCA ACA AAA AAT CCC GAT      155
Lys Asp His Pro Phe Gly Phe Val Ala Val Pro Thr Lys Asn Pro Asp
             20                  25                  30

GGC ACG ATG AAC CTC ATG AAC TGG GAG TGC GCC ATT CCA GGA AAG AAA      203
Gly Thr Met Asn Leu Met Asn Trp Glu Cys Ala Ile Pro Gly Lys Lys
         35                  40                  45

GGG ACT CCG TGG GAA GGA GGC TTG TTT AAA CTA CGG ATG CTT TTC AAA      251
Gly Thr Pro Trp Glu Gly Gly Leu Phe Lys Leu Arg Met Leu Phe Lys
     50                  55                  60

GAT GAT TAT CCA TCT TCG CCA CCA AAA TGT AAA TTC GAA CCA CCA TTA      299
Asp Asp Tyr Pro Ser Ser Pro Pro Lys Cys Lys Phe Glu Pro Pro Leu
 65                  70                  75                  80

TTT CAC CCG AAT GTG TAC CCT TCG GGG ACA GTG TGC CTG TCC ATC TTA      347
Phe His Pro Asn Val Tyr Pro Ser Gly Thr Val Cys Leu Ser Ile Leu
                 85                  90                  95

GAG GAG GAC AAG GAC TGG AGG GCA GNC ATC ACA ATC AAA CAG GAT CCT      395
Glu Glu Asp Lys Asp Trp Arg Ala Xaa Ile Thr Ile Lys Gln Asp Pro
            100                 105                 110

ATT AGG AAT ACA GGA ACT TTC TAAATGAACC AAATATCCAA GACCAGNTCA         446
Ile Arg Asn Thr Gly Thr Phe
        115

AGCAGAGGGC TACANGATTT ACTGCCAAAA CAGAGTNGNG TACGAGAAAG GGTCCGAGCA    506
```

```
NAGCCAGAAG TTTGGGCCTC ATTAGCAGGG ACCTGGTGGA TCGTCAAAGG AGGTTTGGTT      566

GGGAAGACTT GTTCAANATT TNGGAANTTA AGTTGTCCNN NAACTNGCGG GGGGGGGNNN      626

NNCNNNTTNC CANTTCCCTN CCCCCNGTTT TTNGNT                                662

(2) INFORMATION FOR SEQ ID NO:24:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:24:

Val Arg Val Ala Leu Ser Arg Leu Ala Gln Glu Arg Lys Ala Trp Arg
 1               5                  10                  15

Lys Asp His Pro Phe Gly Phe Val Ala Val Pro Thr Lys Asn Pro Asp
                20                  25                  30

Gly Thr Met Asn Leu Met Asn Trp Glu Cys Ala Ile Pro Gly Lys Lys
            35                  40                  45

Gly Thr Pro Trp Glu Gly Gly Leu Phe Lys Leu Arg Met Leu Phe Lys
        50                  55                  60

Asp Asp Tyr Pro Ser Ser Pro Pro Lys Cys Lys Phe Glu Pro Pro Leu
65                  70                  75                  80

Phe His Pro Asn Val Tyr Pro Ser Gly Thr Val Cys Leu Ser Ile Leu
                85                  90                  95

Glu Glu Asp Lys Asp Trp Arg Ala Xaa Ile Thr Ile Lys Gln Asp Pro
                100                 105                 110

Ile Arg Asn Thr Gly Thr Phe
            115

(2) INFORMATION FOR SEQ ID NO:25:

(i) SEQUENCE CHARACTERISTICS:
        (A) LENGTH: 207 base pairs
        (B) TYPE: nucleic acid
        (C) STRANDEDNESS: both
        (D) TOPOLOGY: linear (ii) MOLECULE TYPE: other nucleic acid (xi) SEQUENCE DESCRIPTION: SEQ ID NO:25:

CCCTCCCTCC TGCCGCTCCT CTCTAGAACC TTCTAGAACC TGGGCTGTGC TGCTTTTGAG       60

CCTCAGACCC CAGGGCAGCA TCTCGGTTCT GCGCCACTTC CTTTGTGTTT ANATGGCGTT      120

TTGTCTGTGT TGCTGTTTAG AGTAGATNAA CTGTTTANAT AAAAAAAAAA NAAAATTNAC      180

TNGAGGGGGC NTGNAGGCAT GCNNAAC                                          207
```

IMMUNOSUPPRESSANT TARGET PROTEINS

RELATED APPLICATION

This application is a continuation of U.S. Ser. No. 08/360,144, filed Dec. 20, 1994, now U.S. Pat. No. ,150,137, which is a continuation-in-part of U.S. Ser. No. 08/250,795, filed May 27, 1994, abandoned, and entitled "Immunosuppressant Target Proteins", the specifications of which are incorporated by reference herein.

BACKGROUND OF THE INVENTION

Cyclosporin A, FK506, and rapamycin are microbial products with potent immunosuppressive properties that result primarily from a selective inhibition of T lymphocyte activation. Rapamycin was first described as an antifungal antibiotic extracted from a streptomycete (*Streptomyces hygroscopicus*) (Vezina et al. (1975) *J. Antibiot.*, 28:721; Sehgal et al. (1975) *J. Antibiot.* 28:727; and Sehgal et al., U.S. Pat. No. 3,929,992). Subsequently, the macrolide drug rapamycin was shown to exhibit immunosuppressive as well as antineoplastic and antiproliferative properties (Morris (1992) *Transplant Res* 6:39–87).

Each of these compounds, cyclosporin A, FK506 and rapamycin, suppress the immune system by blocking distinctly different biochemical reactions which would ordinarily initiate the activation of immune cells. Briefly, cyclosporin A and FK506 act soon after $Ca^{2+}$-dependent T-cell activation to prevent the synthesis of cytokines important for the perpetuation and amplification of the immune response. Rapamycin acts later to block multiple affects of cytokines on immune cells including the inhibition of interleukin-2 (IL2)-triggered T-cell proliferation, but its antiproliferative effects are not restricted solely to T and B cells. Rapamycin also selectively inhibits the proliferation of growth factor-dependent and growth factor-independent nonimmune cells. Rapamycin is generally believed to inhibit cell proliferation by blocking specific signaling events necessary for the initiation of S phase in a number of cell types, including lymphocytes (Bierer et al. (1990) *PNAS* 87:9231–9235; and Dumont et al. (1990) *J. Immunol* 144:1418–1424), as well as non-immune cells, such as hepatocytes (Francavilla et al. (1992) *Hepatology* 15:871–877; and Price et al. (1992) *Science* 257:973–977). Several lines of evidence suggest that the association of rapamycin with different members of a family of intracellular FK506/rapamycin binding proteins (FKBPs) is necessary for the inhibition of $G_1$ progression as mediated by rapamycin. For instance, the actions of rapamycin are reversed by an excess of the FKBP-ligands FK506 or 506BD (Bierer et al. supra.; Dumont et al. supra.; and Bierer et al. (1990) *Science* 250:556–559).

Cyclosporin A binds to a class of proteins called cyclophilins (Walsh et al. (1992) *J. Biol. Chem.* 267:13115–13118), whereas the primary targets for both FK506 and rapamycin, as indicated above, are the FKBPs (Harding et al. (1989) *Nature* 341:758–7601; Siekienka et al. (1989) *Nature* 341:755–757; and Soltoff et al. (1992 *J. Biol. Chem.* 267:17472–17477). Both the cyclophilin/cyclosporin and FKBPI2/FK506 complexes bind to a specific protein phosphatase (calcineurin) which is hypothesized to control the activity of IL-2 gene specific transcriptional activators (reviewed in Schreiber (1991) *Cell* 70:365–368). In contrast, the downstream cellular targets for the rapamycin-sensitive signaling pathway have not been especially well characterized, particularly with regard to the identity of the direct target of the FKBP-rapamycin complex.

The TOR1 and TOR2 genes of *S. cerevisiae* were originally identified by mutations that rendered cells resistant to rapamycin (Heitman et al. (1991) *Science* 253:905–909) and there was early speculation that the FKBP/rapamycin complex might inhibit the cellular function of the TOR gene product by binding directly to a phosphoserine residue of either TOR1 or TOR2. Subsequently, however, new models for rapamycin drug interaction have been proposed which do not involve direct binding of the FKBP/rapamycin complex to the TOR proteins. For example, based on experimental data regarding cyclin-cdk activity in rapamycin treated cells, Stuart Schreiber wrote in Albers et al. (1993) *J Biol. Chem.* 268:22825–22829:

"Although it is possible the TOR2 gene product is a direct target of the FKBP-rapamycin complex, a more likely explanation is that the TOR2 gene product lies downstream of the direct target of rapamycin and that the TOR2 mutation caused the protein to be constitutively active. If the latter model is correct, then the TOR2 gene product joins $p70^{s6k}$, cyclin-dependent kinases, and cyclin D1 as proteins that lie downstream of the direct target of the FKBP-rapamycin complex and have been shown to play important roles in cell cycle progression. The identification of the direct target of the FKBP-rapamycin complex will likely reveal an upstream component of the signal transduction pathway that leads to G1 progression and will help delineate the signal transduction pathways that link growth factor-mediated signaling events and cyclin-cdk activity required for cell cycle progression."

Likewise, after studying the role of TOR1 and TOR2 mutations in rapamycin-resistant yeast cells, George Livi wrote in Cafferkey et al. (1993) *Mol. Cell Biol.* 13:6012–6023:

"Thus, the amino acid changes that we have identified in the rapamycin-released DRR1 [TOR1] protein may allow it to compensate for the loss of the proliferative signal inhibited by rapamycin by constitutively activating an alternative signal rather than by preventing its association with the FKBP12-rapamycin complex. The positions of the mutations within the kinase domain, but in a region not shared by the PI 3-kinases, support this idea. Therefore, it is entirely possible that DRR1 is not a component of the rapamycin-sensitive pathway in wild-type yeast cells. Instead, missense mutations in DRR1 at Ser-1972 may alter its normal activity and allow it to substitute for the function of an essential protein which is the true target of rapamycin."

It is an object of the present invention to identify cellular proteins which are the direct downstream target proteins for the FKBP/rapamycin complex, and isolate the genes encoding those proteins.

SUMMARY OF THE INVENTION

The present invention relates to the discovery of novel proteins of mammalian origin which are immediate downstream targets for FKBP/rapamycin complexes. As described herein, a drug-dependent interaction trap assay was used to isolate a number of proteins which interact with an FK506-binding protein/rapamycin complex, and which are collectively referred to herein as "RAP-binding proteins" or "RAP-BPs". In particular, mouse and human genes have been cloned for a protein (referred to herein as "RAPT1") which is apparently related to the yeast TOR1 and TOR2 gene products. Furthermore, a novel ubiquitin-conjugating enzyme (referred to herein as "rap-UBC") has been cloned based on its ability to bind FKBP/rapamycin complexes. In addition, a RAPT1-like protein was cloned from the human pathogen *Candida albicans*. The present invention, therefore, makes available novel proteins (both recombinant and purified forms), recombinant genes, antibodies to RAP-binding proteins, and other novel reagents and assays for diagnostic and therapeutic use.

The present invention relates to the discovery in eukaryotic cells, particularly human cells, of novel protein-protein interactions between the Wilms tumor regulatory protein rapamycin complexes and certain cellular proteins, referred to hereinafter as "RAP-binding proteins" or "RAP-BP".

In general, the invention features a mammalian RAPT1 polypeptide, preferably a substantially pure preparation of a RAPT1 polypeptide, or a recombinant RAPT1 polypeptide. In preferred embodiments the polypeptide has a biological activity associated with its binding to rapamycin, e.g., it retains the ability to bind to an FKBP/rapamycin complex, though it may be able to either agonize or antagonize assembly of rapamycin-dependent complexes. The polypeptide can be identical to a polypeptide shown in one of SEQ ID No: 2 or 12, or it can merely be homologous to that sequence. For instance, the polypeptide preferably has an amino acid sequence at least 60% homologous to the amino acid sequence of at least one of either SEQ ID No: 2 or 12, though higher sequence homologies of, for example, 80%, 90% or 95% are also contemplated. The polypeptide can comprise the full length protein, or a portion of a full length protein, such as the RAPT1 polypetides represented in either SEQ ID No: 2 or 12, or an even smaller fragment of that protein, which fragment may be, for instance, at least 5, 10, 20, 50 or 100 amino acids in length. As described below, the RAPT1 polypeptide can be either an agonist (e.g. mimics), or alternatively, an antagonist of a biological activity of a naturally occuring form of the protein, e.g., the polypeptide is able to modulate assembly of rapamycin complexes, such as complexes involving FK506-binding proteins, or cell cycle regulatory proteins.

In a preferred embodiment, a peptide having at least one biological activity of the subject RAPT1 polypepides may differ in amino acid sequence from the sequence in SEQ ID No: 2 or 12, but such differences result in a modified protein which functions in the same or similar manner as the native RAPT1 protein or which has the same or similar characteristics of the native RAPT1 protein. However, homologs of the naturally occuring protein are contemplated which are antagonistic of the normal cellular role of the naturally occurring protein.

In yet other preferred embodiments, the RAPT1 protein is a recombinant fusion protein which includes a second polypeptide portion, e.g., a second polypeptide having an amino acid sequence unrelated to the RAPT1 polypeptide portion, e.g. the second polypeptide portion is glutathione-S-transferase, e.g. the second polypeptide portion is a DNA binding domain of transcriptional regulatory protein, e.g. the second polypeptide portion is an RNA polymerase activating domain, e.g. the fusion protein is functional in a two-hybrid assay.

Yet another aspect of the present invention concerns an immunogen comprising a RAPT1 peptide in an immunogenic preparation, the immunogen being capable of eliciting an immune response specific for the RAPT1 polypeptide; e.g. a humoral response, e.g. an antibody response; e.g. a cellular response. In preferred embodiments, the immunogen comprising an antigenic determinant, e.g. a unique determinant, from a protein represented by SEQ ID No: 2 and/or 12.

A still further aspect of the present invention features an antibody preparation specifically reactive with an epitope of the RAPT1 immunogen.

In another aspect, the invention features a ubiquitin conjugating enzyme (rap-UBC), preferably a substantially pure preparation of a rap-UBC polypeptide, or a recombinant rap-UBC polypeptide. As above, in preferred embodiments the rap-UBC polypeptide has a biological activity associated with its binding to rapamycin, e.g., it retains the ability to bind to a rapamycin complex, and may additionally retain a ubiquitin conjugating activity. The polypeptide can be identical to the polypeptide shown in SEQ ID No: 24, or it can merely be homologous to that sequence. For instance, the polypeptide preferably has an amino acid sequence at least 60% homologous to the amino acid sequence in SEQ ID No: 24, though higher sequence homologies of, for example, 80%, 90% or 95% are also contemplated. The rap-UBC polypeptide can comprise the full length polypeptide represented in SEQ ID No: 24, or it can comprise a fragment of that protein, which fragment may be, for instance, at least 5, 10, 20, 50 or 100 amino acids in length. The rap-UBC polypeptide can be either an agonist (e.g. mimics), or alternatively, an antagonist of a biological activity of a naturally occuring form of the protein.

In a preferred embodiment, a peptide having at least one biological activity of the subject rap-UBC polypeptide may differ in amino acid sequence from the sequence in SEQ ID No: 24, but such differences result in a modified protein which functions in the same or similar manner as the native rap-UBC or which has the same or similar characteristics of the native protein. However, homologs of the naturally occuring rap-UBC protein are contemplated which are antagonistic of the normal cellular role of the naturally occurring protein.

In yet other preferred embodiments, the rap-UBC protein is a recombinant fusion protein which includes a second polypeptide portion, e.g., a second polypeptide having an amino acid sequence unrelated to the rap-UBC sequence, e.g. the second polypeptide portion is glutathione-S-transferase, e.g. the second polypeptide portion is a DNA binding domain of transcriptional regulatory protein, e.g. the second polypeptide portion is an RNA polymerase activating domain, e.g. the fusion protein is functional in a two-hybrid assay.

Yet another aspect of the present invention concerns an immunogen comprising a rap-UBC peptide in an immunogenic preparation, the immunogen being capable of eliciting an immune response specific for the rap-UBC polypeptide; e.g. a humoral response, e.g. an antibody response; e.g. a cellular response. In preferred embodiments, the immunogen comprising an antigenic determinant, e.g. a unique determinant, from a protein represented by SEQ ID No: 24.

A still further aspect of the present invention features an antibody preparation specifically reactive with an epitope of the rap-UBC immunogen.

In still another aspect, the invention features a RAPT1-like polypeptide from a Candida species (caRAPT1), preferably a substantially pure preparation of a caRAPT1 polypeptide, or a recombinant caRAPT1 polypeptide. As above, in preferred embodiments the caRAPT1 polypeptide has a biological activity associated with its binding to rapamycin, e.g., it retains the ability to bind to a rapamycin complex, such as an FKBP/rapamycin complex. The polypeptide can be identical to the polypeptide shown in SEQ ID No: 14, or it can merely be homologous to that sequence. For instance, the caRAPT1 polypeptide preferably has an amino acid sequence at least 60% homologous to the amino acid sequence in SEQ ID No: 14, though higher sequence homologies of, for example, 80%, 90% or 95% are also contemplated. The caRAPT1 polypeptide can comprise the entire polypeptide represented in SEQ ID No: 14, or it can comprise a fragment of that protein, which fragment may be, for instance, at least 5, 10, 20, 50 or 100 amino acids in length. The caRAPT1 polypeptide can be either an agonist (e.g. mimics), or alternatively, an antagonist of a biological activity of a naturally occuring form of the protein.

In a preferred embodiment, a peptide having at least one biological activity of the subject caRAPT1 polypeptide may differ in amino acid sequence from the sequence in SEQ ID No: 14, but such differences result in a modified protein which functions in the same or similar manner as the native caRAPT1 or which has the same or similar characteristics of the native protein. However, homologs of the naturally occuring caRAPT1 protein are contemplated which are antagonistic of the normal cellular role of the naturally occurring protein.

In yet other preferred embodiments, the caRAPT1 protein is a recombinant fusion protein which includes a second polypeptide portion, e.g., a second polypeptide having an amino acid sequence unrelated to the caRAPT1 sequence, e.g. the second polypeptide portion is glutathione-S-transferase, e.g. the second polypeptide portion is a DNA binding domain of transcriptional regulatory protein, e.g. the second polypeptide portion is an RNA polymerase activating domain, e.g. the fusion protein is functional in a two-hybrid assay.

Yet another aspect of the present invention concerns an immunogen comprising a caRAPT1 peptide in an immunogenic preparation, the immunogen being capable of eliciting an immune response specific for the caRAPT1 polypeptide; e.g. a humoral response, e.g. an antibody response; e.g. a cellular response. In preferred embodiments, the immunogen comprising an antigenic determinant, e.g. a unique determinant, from a protein represented by SEQ ID No: 14.

A still further aspect of the present invention features an antibody preparation specifically reactive with an epitope of the caRAPT1 immunogen.

Another aspect of the present invention provides a substantially isolated nucleic acid having a nucleotide sequence which encodes a RAPT1 polypeptide. In preferred embodiments: the encoded polypeptide specifically binds a rapamycin complexes and/or is able to either agonize or antagonize assembly of rapamycin-containing protein complexes. The coding sequence of the nucleic acid can comprise a RAPT1-encoding sequence which can be identical to the cDNA shown in SEQ ID No: 1 or 11, or it can merely be homologous to that sequence. For instance, the RAPT1-encoding sequence preferably has a sequence at least 60% homologous to one or both of the nucleotide sequences in SEQ ID No: 1 or 11, though higher sequence homologies of, for example, 80%, 90% or 95% are also contemplated. The nucleic acid can comprise the nucleotide sequence represented in SEQ ID No: 1, or it can comprise a fragment of that nucleic acid, which fragment may be, for instance, encode a fragment of which is, for example, at least 5, 10, 20, 50, 100 or 133 amino acids in length. The polypeptide encoded by the nucleic acid can be either an agonist (e.g. mimics), or alternatively, an antagonist of a biological activity of a naturally occuring form of the RAPT1 protein, e.g., the polypeptide is able to modulate rapamycin-mediated protein complexes.

Furthermore, in certain preferred embodiments, the subject RAPT1 nucleic acid will include a transcriptional regulatory sequence, e.g. at least one of a transcriptional promoter or transcriptional enhancer sequence, which regulatory sequence is operably linked to the RAPT1 gene sequence. Such regulatory sequences can be used in to render the RAPT1 gene sequence suitable for use as an expression vector.

In yet a further preferred embodiment, the nucleic acid hybridizes under stringent conditions to a nucleic acid probe corresponding to at least 12 consecutive nucleotides of SEQ ID No: 1 and/or 11; preferably to at least 20 consecutive nucleotides, and more preferably to at least 40 consecutive nucleotides.

Another aspect of the present invention provides a substantially isolated nucleic acid having a nucleotide sequence which encodes a rap-UBC polypeptide. In preferred embodiments: the encoded polypeptide specifically binds a rapamycin complexes and/or is able to either agnoize or antagonize assembly of rapamycin-containing protein complexes. The coding sequence of the nucleic acid can comprise a rap-UBC-encoding sequence which can be identical to the cDNA shown in SEQ ID No: 23, or it can merely be homologous to that sequence. For instance, the rap-UBC-encoding sequence preferably has a sequence at least 60% homologous to the nucleotide sequences in SEQ ID No: 23, though higher sequence homologies of, for example, 80%, 90% or 95% are also contemplated. The nucleic acid can comprise the nucleotide sequence represented in SEQ ID No: 23, or it can comprise a fragment of that nucleic acid, which fragment may be, for instance, encode a fragment of which is, for example, at least 5, 10, 20, 50, or 100 amino acids in length. The polypeptide encoded by the nucleic acid can be either an agonist (e.g. mimics), or alternatively, an antagonist of a biological activity of a naturally occuring form of the rap-UBC protein, e.g., the polypeptide is able to modulate rapamycin-mediated protein complexes.

Furthermore, in certain preferred embodiments, the subject rap-UBC nucleic acid will include a transcriptional regulatory sequence, e.g. at least one of a transcriptional promoter or transcriptional enhancer sequence, which regulatory sequence is operably linked to the rap-UBC gene sequence. Such regulatory sequences can be used in to render the rap-UBC gene sequence suitable for use as an expression vector.

In yet a further preferred embodiment, the nucleic acid hybridizes under stringent conditions to a nucleic acid probe corresponding to at least 12 consecutive nucleotides of SEQ ID No: 23; preferably to at least 20 consecutive nucleotides, and more preferably to at least 40 consecutive nucleotides.

Another aspect of the present invention provides a substantially isolated nucleic acid having a nucleotide sequence which encodes a caRAPT1 polypeptide. In preferred embodiments: the encoded polypeptide specifically binds a rapamycin complexes and/or is able to either agnoize or antagonize assembly of rapamycin-containing protein complexes. The coding sequence of the nucleic acid can comprise a caRAPT1-encoding sequence which can be identical to the cDNA shown in SEQ ID No: 13, or it can merely be homologous to that sequence. For instance, the caRAPT1-encoding sequence preferably has a sequence at least 60% homologous to the nucleotide sequences in SEQ ID No: 13, though higher sequence homologies of, for example, 80%, 90% or 95% are also contemplated. The nucleic acid can comprise the nucleotide sequence represented in SEQ ID No: 13, or it can comprise a fragment of that nucleic acid, which fragment may be, for instance, encode a fragment of which is, for example, at least 5, 10, 20, 50, 100 or 133 amino acids in length. The polypeptide encoded by the nucleic acid can be either an agonist (e.g. mimics), or alternatively, an antagonist of a biological activity of a naturally occuring form of the caRAPT1 protein, e.g., the polypeptide is able to modulate rapamycin-mediated protein complexes.

Furthermore, in certain preferred embodiments, the subject caRAPT1 nucleic acid will include a transcriptional regulatory sequence, e.g. at least one of a transcriptional promoter or transcriptional enhancer sequence, which regulatory sequence is operably linked to the caRAPT1 gene sequence. Such regulatory sequences can be used in to render the caRAPT1 gene sequence suitable for use as an expression vector.

In yet a further preferred embodiment, the nucleic acid hybridizes under stringent conditions to a nucleic acid probe corresponding to at least 12 consecutive nucleotides of SEQ ID No: 13; preferably to at least 20 consecutive nucleotides, and more preferably to at least 40 consecutive nucleotides.

The invention also features transgenic non-human animals, e.g. mice, rats, rabbits or pigs, having a transgene, e.g., animals which include (and preferably express) a heterologous form of one of the RAP-BP genes described herein, e.g. a gene derived from humans, or which misexpress an endogenous RAP-BP gene, e.g., an animal in which expression of one or more of the subject RAP-binding proteins is disrupted. Such a transgenic animal can serve as an animal model for studying cellular disorders comprising mutated or mis-expressed RAP-BP alleles or for use in drug screening.

The invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of one of SEQ ID Nos: 1, 11, 13 or 24, or naturally occurring mutants thereof. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying transformed cells, such as for detecting in a sample of cells isolated from a patient, a level of a nucleic acid encoding one of the subject RAP-binding proteins; e.g. measuring the RAP-BP mRNA level in a cell, or determining whether the genomic RAP-BP gene has been mutated or deleted. Preferably, the oligonucleotide is at least 10 nucleotides in length, though primers of 20, 30, 50, 100, or 150 nucleotides in length are also contemplated.

In yet another aspect, the invention provides assay systems for screening test compounds for an molecules which induce an interaction between a RAP-binding protein and a rapamycin/protein complexes. An exemplary method includes the steps of (i) combining a RAP-binding protein of the invention, an FK506-binding protein, and a test compound, e.g., under conditions wherein, but for the test compound, the FK506-binding protein and the RAP-binding protein are unable to interact; and (ii) detecting the formation of a drug-dependent complex which includes the FK506-binding protein and the RAP-binding protein. A statistically significant change, such as an increase, in the formation of the complex in the presence of a test compound (relative to what is seen in the absence of the test compound) is indicative of a modulation, e.g., induction, of the interaction between the FK506-binding protein and the RAP-binding protein. Moreover, primary screens are provided in which the FK506-binding protein and the RAP-binding protein are combined in a cell-free system and contacted with the test compound; i.e. the cell-free system is selected from a group consisting of a cell lysate and a reconstituted protein mixture. Alternatively, FK506-binding protein and the RAP-binding protein are simultaneously expressed in a cell, and the cell is contacted with the test compound, e.g. as an interaction trap assay (two hybrid assay).

The present invention also provides a method for treating an animal having unwanted cell growth characterized by a loss of wild-type function of one or more of the subject RAP-binding proteins, comprising administering a therapeutically effective amount of an agent able to inhibit the interaction of the RAP-binding protein with other cellular or viral proteins. In one embodiment, the method comprises administering a nucleic acid construct encoding a polypeptides represented in one of SEQ ID Nos: 2, 12 or 24, under conditions wherein the construct is incorporated by cells deficient in that RAP-binding protein, and under conditions wherein the recombinant gene is expressed, e.g. by gene therapy techniques. In other embodiments, the action of a naturally-occurring RAP-binding protein is antagonized by therapeutic expression of a RAP-BP homolog which is an antagonist of, for example, assembly of rapamycin-mediated complexes, or by delivery of an antisense nucleic acid molecule which inhibits transcription and/or translation of the targeted RAP-BP gene.

Another aspect of the present invention provides a method of determining if a subject, e.g. a human patient, is at risk for a disorder characterized by unwanted cell proliferation. The method includes detecting, in a tissue of the subject, the presence or absence of a genetic lesion characterized by at least one of (i) a mutation of a gene encoding a protein represented by one of SEQ ID Nos: 1, 11 or 13, or a homolog thereof; (ii) the mis-expression of a gene encoding a protein represented by one of SEQ ID Nos: 1, 11 or 13; or (iii) the mis-incorporation of a RAP-binding protein in a regulatory protein complex, e.g. a rapamycin-containing complex. In preferred embodiments: detecting the genetic lesion includes ascertaining the existence of at least one of: a deletion of one or more nucleotides from the RAP-BP gene; an addition of one or more nucleotides to the gene, an substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; or a non-wild type level of the protein.

For example, detecting the genetic lesion can include (i) providing a probe/primer including an oligonucleotide containing a region of nucleotide sequence which hybridizes to a sense or antisense sequence of one of SEQ ID Nos: 1, 11 or 23, or naturally occurring mutants thereof or 5' or 3' flanking sequences naturally associated with the RAP-BP gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the RAP-BP gene and, optionally, of the flanking nucleic acid sequences. For instance, the probe/primer can be employed in a polymerase chain reaction (PCR) or in a ligation chain reaction (LCR). In alternate embodiments, the level of the RAP-binding protein is detected in an immunoassay using an antibody which is specifically immunoreactive with a protein represented by one of SEQ ID Nos: 1, 11 or 23.

Another aspect of the present invention concerns a novel in vivo method for the isolation of genes encoding proteins which physically interact with a "bait" protein/drug complex. The method relies on detecting the reconstitution of a transcriptional activator in the presence of the drug, particularly wherein the drug is a non-peptidyl small organic molecule (e.g.<2500K), e.g. a macrolide, e.g. rapamycin, FK506 or cyclosporin. In particular, the method makes use of chimeric genes which express hybrid proteins. The first hybrid comprises the DNA-binding domain of a transcriptional activator fused to the bait protein. The second hybrid protein contains a transcriptional activation domain fused to a "fish" protein, e.g. a test protein derived from a cDNA library. If the fish and bait proteins are able to interact in a drug-dependent manner, they bring into close proximity the two domains of the transcriptional activator. This proximity is sufficient to cause transcription of a reporter gene which is operably linked to a transcriptional regulatory site responsive to the transcriptional activator, and expression of the marker gene can be detected and used to score for the interaction of the bait protein/drug complex with another protein.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. : 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

DESCRIPTION OF THE FIGURES

FIGS. 3A–3L illustrate the relative strengths of interaction between pairs of FK506-binding proteins and rapamycin-binding domain (BD) fusions in the presence of varying concentrations of rapamycin, measured by β-galactosidase expression (see Example 8). The yeast reporter strain VBY567 was transformed with the indicated pairs of plasmids. LexA DNA-binding domain fusions to human FKBP12, yeast FKBP12 and an unrelated sequence serving as negative control were used as "baits". The VP16 acidic activation domain fusions to human RAPT1 BD, human RAPT1 BD containing the serine to arginine substitution, yeast Tor1 BD, yeast Tor2 BD (not shown) and Candida albicans RAPT1 BD were tested for interaction against the bait fusions. Transformants containing each pair of plasmids were tested for β-galactosidase expression on media containing the chromogenic substrate X-gal. Colonies were scored as either white (open bars) or blue (solid bars) after growth at 30° C. for 2 days. The levels of β-galactosidase expression were qualitatively scored by the intensity of the blue color, ranging from 1 (light blue) to 4 (deep blue).

DETAILED DESCRIPTION OF THE INVENTION

Figure 1:
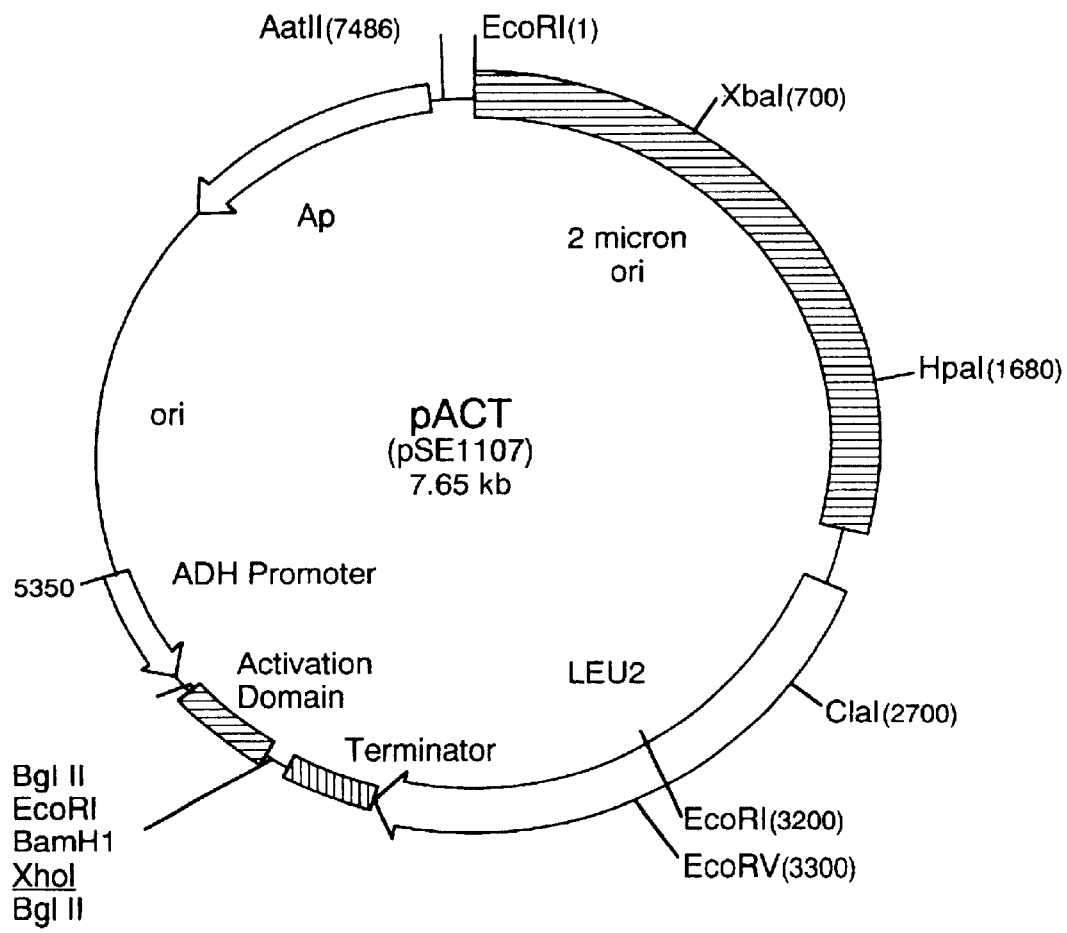
FIG. 1 illustrates the map of the pACT vector used to clone the human RAPT1 clone. The RAPT1-containing version of pACT, termed "pIC524" has been deposited with the ATCC.

Recent studies have provided some remarkable insights into the molecular basis of eukaryotic cell cycle regulation. Passage of a mammalian cell through the cell cycle is regulated at a number of key control points. Among these are the points of entry into and exit from quiescence ($G_0$), the restriction point, the $G_1$/S transition, and the $G_2$/M transition (for review, see Draetta (1990) *Trends Biol Sci* 15:378–383; and Sherr (1993) *Cell* 73:1059–1065). Ultimately, information from these check-point controls is integrated through the regulated activity of a group of related kinases, the cyclin-dependent kinases (CDKs). For example, the $G_1$-to-S phase transition is now understood to be timed precisely by the transient assembly of multiprotein complexes involving the periodic interaction of a multiplicity of cyclins and cyclin-dependent kinases.

To illustrate, stimulation of quiescent T lymphocytes by cell-bound antigens triggers a complex activation program resulting in cell cycle entry ($G_0$-to-$G_1$ transition) and the expression of high affinity interleukin-2 (IL-2) receptors. The subsequent binding of IL-2 to its high affinity receptor drives the progression of activated T cells through a late $G_1$-phase "restriction point" (Pardee (1989) *Science* 246:603–608), after which the cells are committed to complete a relatively autonomous program of DNA replication and, ultimately, mitosis.

One important outcome of the information concerning eukaryotic cell cycle regulation is the delineation of a novel class of molecular targets for potential growth-modulatory drugs. The macrolide ester, rapamycin, is a potent immunosuppressant whose mechanism of action is related to the inhibition of cytokine-dependent T cell proliferation (Bierer et al. (1990) *PNAS* 87:9231–9235; Dumont et al. (1990) *J. Immunol* 144:1418–1424; Sigal et al. (1991) *Transplant Proc* 23:1–5; and Sigal et al. (1992) *Annu Rev Immunol* 10:519–560). Rapamycin specifically interferes with a late $G_1$-phase event required for the progression of IL-2 stimulated cells into S-phase (Morice et al. (1993) *J Biol Chem* 268:3734–3738). The location of the cell cycle arrest point induced by rapamycin hints that this drug interferes with the regulatory proteins that govern the $G_1$-to-S phase transition, particularly in lymphocytes.

As described herein, the present invention relates to the discovery of novel proteins of mammalian origin which are immediate downstream targets for FKBP/rapamycin complexes. As described below, a drug-dependent interaction trap assay was used to isolate a number of proteins which bind the FKBP12/rapamycin complex, and which are collectively referred to herein as "RAP-binding proteins" or "RAP-BPs". In particular, mouse and human genes have been cloned for a protein (referred to herein as "RAPT1") which is apparently related to the yeast TOR1 and TOR2 gene products. Furthermore, a novel ubiquitin-conjugating enzyme (referred to herein as "rap-UBC") has been cloned based on its ability to bind FKBP/rapamycin complexes. The present invention, therefore, makes available novel proteins (both recombinant and purified forms), recombinant genes, antibodies to RAP-binding proteins, and other novel reagents and assays for diagnostic and therapeutic use. Moreover, drug discovery assays are provided for identifying agents which can modulate the binding of one or more of the subject RAP-binding proteins with FK506-binding proteins. Such agents can be useful therapeutically to alter the growth and/or differentiation of a cell, but can also be used in vitro as cell-culture additives for controlling proliferation and/or differentiation of cultured cells and tissue. Other aspects of the invention are described below or will be apparent to those skilled in the art in light of the present disclosure.

For convience, certain terms employed in the specfication, examples, and appended claims are collected here.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

The term "gene" or "recombinant gene" refers to a nucleic acid comprising an open reading frame encoding a RAP-binding protein of the present invention, including both exon and (optionally) intron sequences. A "recombinant gene" refers to nucleic acid encoding a RAP-binding protein and comprising RAP-BP encoding exon sequences, though it may optionally include intron sequences which are either derived from a chromosomal RAP-BP gene or from an unrelated chromosomal gene. Exemplary recombinant genes encoding illustrative RAP-binding proteins include a nucleic acid sequence represented by on of SEQ ID Nos: 1, 11 or 23. The term "intron" refers to a DNA sequence present in a given RAP-BP gene which is not translated into protein and is generally found between exons.

As used herein, the term "transfection" refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of the RAP-binding protein of the present invention or where anti-sense expression occurs from the transferred gene, the expression for a naturally-occurring form of the RAP-binding protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant RAP-BP gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the RAP-binding protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a lymphoid lineage, e.g. B or T lymphocytes, or alternatively, e.g. hepatic cells. In an illustrative embodiment, gene constructs utilizing lymphoid-specific promoters can be used as a part of gene therapy to provide dominant negative mutant forms of a RAP-binding protein to render lymphatic cells resistant to rapamycin by directing expression of the mutant form of RAP-BP in only lymphatic tissue. The term also covers so-called "leaky" promoters, which regulate expression of a selected DNA primarily in one tissue, but cause expression in other tissues as well.

As used herein, a "transgenic animal" is any animal, preferably a non-human mammal, a bird or an amphibian, in which one or more of the cells of the animal contain heterologous nucleic acid introduced by way of human intervention, such as by trangenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of a subject RAP-binding protein, e.g. either agonistic or antagonistic forms. However, transgenic animals in which the recombinant RAP-BP gene is silent are also contemplated, as for example, the FLP or CRE recombinase dependent constructs described below. The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding, for example, embryogenesis and tissue patterning. The term "chimeric animal" is used herein to refer to animals in which the recombinant gene is found, or in which the recombinant is expressed in some but not all cells of the animal. The term "tissue-specific chimeric animal" indicates that the recombinant RAP-BP gene is present and/or expressed in some tissues but not others.

As used herein, the term "transgene" means a nucleic acid sequence (encoding, e.g., a RAP-binding protein), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a RAP-binding protein" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject RAP-binding proteins with a second amino acid sequence defining a domain foreign to and not substantially homologous with any domain of the subject RAP-BP. A chimeric protein may present a foreign domain which is found (albeit in a different protein) in an organism which also expresses the first protein, or it may be an "interspecies", "intergeneric", etc. fusion of protein structures expressed by different kinds of organisms.

The term "evolutionarily related to", with respect to nucleic acid sequences encoding RAP-binding proteins, refers to nucleic acid sequences which have arisen naturally in an organism, including naturally occurring mutants. Moreover, the term also refers to nucleic acid sequences which, while initially derived from naturally-occurring isoforms of RAP-binding proteins, have been altered by mutagenesis, as for example, such combinatorial mutagenesis as described below, yet which still encode polypeptides that bind FKBP/rapamycin complexes, or that retain at least one activity of the parent RAP-binding protein, or which are antagonists of that protein's activities.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding one of the subject RAP-binding proteins preferably includes no more than 10 kilobases (kb) of nucleic acid sequence which naturally immediately flanks that particular RAP-BP gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As used herein, an "rapamycin-binding domain" refers to a polypeptide sequence which confers a binding activity for specifically interacting with an FKBP/rapamycin complex. Exemplary rapamycin-binding domains are represented within the polypeptides defined by Val28 Tyr160 of SEQ ID No. 2, Val1272-Tyr1404 of SEQ ID No. 12, Val41-Tyr173 of SEQ ID No. 14, Val1-Tyr133 of SEQ ID No. 16, and Val1-Arg133 of SEQ ID No. 18.

A "RAPT1-like polypeptide" refers to a eukaryotic cellular protein which is a direct binding target protein for an FKBP/rapamycin complex, and which shares some sequence homology with a mammalian RAPT1 protein of the present invention. Exemplary RAPT1-like polypeptides include the yeast TOR1 and TOR2 proteins.

A "soluble protein" refers to a polypeptide which does not precipitate (e.g. at least about 95-percent, more preferably at least 99-percent remains in the supernatant) from an aqueous buffer under physiologically isotonic conditios, for example, 0.14M NaCl or sucrose, at a protein concentration of as much as 10 $\mu$M, more preferably as much as 10 mM. These conditions specifically relate to the absence of detergents or other denaturants in effective concentrations.

As described below, one aspect of this invention pertains to an isolated nucleic acid comprising the nucleotide sequence encoding a RAP-binding protein, fragments thereof, and/or equivalents of such nucleic acids. The term nucleic acid as used herein is intended to include such fragments and equivalents. The term equivalent is understood to include nucleotide sequences encoding functionally equivalent RAP-binding proteins or functionally equivalent peptides which, for example, retain the ability to bind to the FKBP/rapamycin complex, and which may additionally retain other activities of a RAP-binding protein such as described herein. Equivalent nucleotide sequences will include sequences that differ by one or more nucleotide substitutions, additions or deletions, such as allelic variants; and will also include sequences that differ from the nucleotide sequence of the mammalian RAPT1 genes represented in SEQ ID No: 1 or SEQ ID No. 11, or the nucleotide sequence of the fungal RAPT1 protein of SEQ ID No. 13, or the nucleotide sequence encoding the UBC enzyme represented in SEQ ID No. 23, due to the degeneracy of the genetic code. Equivalent nucleic acids will also include nucleotide sequences that hybridize under stringent conditions (i.e., equivalent to about 20–27° C. below the melting temperature ($T_m$) of the DNA duplex formed in about 1M salt) to a nucleotide sequence of a RAPT1 protein comprising either the sequence shown in SEQ ID No: 2 or 12, or to a nucleotide sequence of the RAPT1 gene insert of pIC524 (ATCC accession no. 75787). Likewise, equivalent nucleic acids encoding homologs of the subject rap-UBC enzyme include nucleotide sequences that hybridize under stringent conditions to a nucleotide sequence represented in SEQ ID No. 23, or to a nucleotide sequence of the rap-UBC gene insert of SMR4-15 (ATCC accession no. 75786). In one embodiment, equivalents will further include nucleic acid sequences derived from, and evolutionarily related to, a nucleotide sequence comprising that shown in either SEQ ID No. 1, or SEQ ID No. 11, or SEQ ID No. 13, or SEQ ID No. 23.

The amino acid sequences shown in each of SEQ ID Nos: 2 and 12 represent biologically active portions of larger full-length forms of mammalian RAPT1 proteins. In preferred embodiments, the RAPT1 polypeptide includes a binding domain for binding to FKBP/rapamyin complexes, such as the rap-binding domains represented by residues 28–160 of SEQ ID No. 2, or residues 1272–1404 of SEQ ID No. 12. In preferred embodiments, portions of the RAPT1 protein isolated from the full-length form will retain a specfic binding affinity for an FKBP/rapamycin complex, e.g. an FKBP12/rapamycin complex, e.g. an affinity at least 50%, more prefereably at least 75%, and even more preferably at least 90% that of the binding affinity of a naturally-occurring form of RAPT1 for such a rapamycin complex. A polypeptide is considered to possess a biological activity of a RAPT1 protein if the polypeptide has one or more of the following properties: the ability to bind an FKBP/drug complex, e.g., an FKBP/macrolide complex, e.g., an FKBP/rapamycin complex; the ability to bind to an FKBP12/rapamycin complex; the ability to modulate assembly of FKBP/rapamycin-complexes; the ability to regulate cell proliferation, e.g., to regulate the cell-cycle, e.g., to regulate the progression of a cell through the $G_1$ phase. Moreover, based on sequence analysis, the biological function of the subject RAPT1 proteins can include a phosphatidyl inositol-kinase activity, such as a PI-3-kinase activity. A protein also has biological activity if it is a specific agonist or antagonist of one of the above recited properties.

Likewise, the amino acid sequence shown in SEQ ID No. 24 represents a biologically active portion of a larger full-length form of a human ubiquitin-conjugating enzyme. Accordingly, preferred embodiments of the subject rap-UBC comprise at least a portion of the amino acid sequence of SEQ ID No. 24 (or of the rap-UBC gene insert of SMR4-15 described in Example 5) which possess either the ability to bind a FKBP/rapamycin complex or the ability to conjugating ubiquitin to a cellular protein, or both. Given that rapamycin causes a block in the cell-cycle during G1 phase, it is probable that the spectrum of biological activity of the subject rap-UBC enzyme includes control of half-lives of certain cell cycle regulatory proteins, particularly relatively short lived proteins (e.g. proteins which have half-lives on the order of 30 minutes to 2 hours). For example, the subject UBC may have the ability to mediate ubiquitination of, for example, p53, myc and/or cyclins, and therefore affects the cellular half-life of a cell-cycle regulatory protein in proliferating cells. The binding of the rap-UBC to the FKBP/rapamycin complex may result in sequestering of the enzyme away from its substrate proteins. Thus, rapamycin may intefere with the ubiquitin-meditated degradation of p53 in a manner which causes cellular p53 levels to rise which in turn inhibits progression of the G1 phase.

Moreover, it will be generally appreciated that, under certain circumstances, it may be advantageous to provide homologs of the cloned RAP-binding proteins which function in a limited capacity as one of either a RAP-BP agonists or a RAP-BP antagonists, in order to either promote or inhibit only a subset of the biological activities of the naturally occurring form of the protein. Thus, specific biological effects can be elicited by treatment with a homolog of limited function, and with fewer side effects relative to treatment with agonists or antagonists which are directed to all RAP-BP related biological activities. For instance, RAPT1 analogs and rap-UBC analogs can be generated which do not bind in any substantial fashion to an FKBP/rapamycin complex, yet which retain most of the other biological functions ascribed to the naturally-occurring form of the protein. For example, the RAPT1 homolog might retain a kinase activity, such as a phosphatidyl inositol kinase activity, e.g. a PI-3-kinase activity. Conversely, the RAPT1 homolog may be engineered to lack a kinase activity, yet retain the ability to bind an FKBP/rapamycin complex. For instance, the FKBP/rapamycin binding portions of the RAPT1 homologs, such as the rapamycin-binding domains represented in SEQ ID Nos. 2 or 12, can be used to competitively inhibit binding to rapamycin complexes by the naturally-occurring form of RAPT1. In similar fashion, rap-UBC homologs can be provided which, for example, are catalytically inactive (e.g. an active site mutant, e.g. Cys-92 to Ser) yet which still binds an FKBP/rapamycin complex. Such a homolog is likely to act antagonistically to the role of the natural enzyme in rapamycin action.

Homologs of the subject RAP-binding proteins can be generated by mutagenesis, such as by discrete point mutation(s), or by truncation. For instance, mutation can give rise to homologs which retain substantially the same, or merely a subset, of the biological activity of the RAP-BP from which it was derived. Alternatively, antagonistic forms of the protein can be generated which are able to inhibit the function of the naturally occurring form of the protein, such as by competitively binding to FKBP/rapamycin complexes.

The nucleotide sequence shown in SEQ ID No: 1 encodes a biologically active portion of the mouse RAPT1 protein, and in particular, includes a rapamycin-binding domain. Accordingly, in one embodiment of the present invention, the nucleic acid is a cDNA encoding a peptide including an amino acid sequence substantially homologous to that portion of the RAPT1 protein represented by SEQ ID No: 2. Preferably, the nucleic acid is a cDNA molecule comprising at least a portion of the nucleotide sequence shown in SEQ ID No: 1. Likewise, the nucleotide sequence shown in SEQ ID No. 11 encodes a biologically active portion of the human RAPT1 protein. Thus, another embodiment of the present invention provides a cDNA encoding a peptide having an amino acid sequence substantially homologous to that portion of the RAPT1 protein represented by SEQ ID No. 12. In similar fashion, the present invention provides a cDNA encoding at least a portion of the Candida RAPT1 polypeptide of SEQ ID No. 14.

Preferred nucleic acids encode a polypeptide including an amino acid sequence which is at least 60% homologous, more preferably 70% homologous and most preferably 80% homologous with an amino acid sequence shown in one or more of SEQ ID Nos: 2, 12 or 14. Nucleic acids encoding peptides, particularly peptides having an activity of a RAPT1 protein, and comprising an amino acid sequence which is at least about 90%, more preferably at least about 95%, and most preferably at least about 98–99% homologous with a sequence shown in either SEQ ID No: 2, 12 or 14 are also within the scope of the invention, as of course are proteins which are identical to the aforementioned sequence listings. In one embodiment, the nucleic acid is a cDNA encoding a peptide having at least one activity of a subject RAP-binding protein. Preferably, the nucleic acid is a cDNA molecule comprising at least a portion of the nucleotide sequence represented in one of SEQ ID Nos: 2, 12 or 14. A preferred portion of these cDNA molecules includes the coding region of the gene. For instance, a recombinant RAP-BP gene can include nucleotide sequences of a PCR fragment generated by amplifying the coding sequences for one of the RAP-BP clones of ATCC deposit No: 75787.

The nucleotide sequence shown in SEQ ID No: 23 encodes a biologically active portion of the human rap-UBC enzyme. Accordingly, in one embodiment of the present invention, the nucleic acid is a cDNA encoding a peptide including an amino acid sequence substantially homologous to that portion of the rap-UBC protein represented by SEQ ID No: 24. Preferably, the nucleic acid is a cDNA molecule comprising at least a portion of the nucleotide sequence shown in SEQ ID No: 23. Preferred nucleic acids encode a peptide comprising an amino acid sequence which is at least 60% homologous, more preferably 70% homologous and most preferably 80% homologous with an amino acid sequence shown in SEQ ID No: 24. Nucleic acids encoding polypeptides, particularly those having a ubiquitin conjugating activity, and comprising an amino acid sequence which is at least about 90%, more preferably at least about 95%, and most preferably at least about 98–99% homologous with a sequence shown in SEQ ID No: 24 are also within the scope of the invention.

In a further embodiment of the invention, the recombinant RAP-BP genes can further include, in addition to the amino acid sequence shown in SEQ ID No. 2, 12 or 24, additional nucleotide sequences which encode amino acids at the C-terminus and N-terminus of the protein though not shown in those sequence listings. For instance, the recombinant RAPT1 gene can include nucleotide sequences of a PCR fragment generated by amplifying the RAPT1 coding sequence of pIC524 using sets of primers such described in Example 4. Additionally, in light of the present disclosure, it will be possible using no more than routine experimentation to isolate from, for example, a cDNA library, the remaining 5' sequences of RAPT1, such as by RACE PCR using primers designed from the present sequences. In particular, the invention contemplates a recombinant RAPT1 gene encoding the full-length RAPT1 protein. Yet another embodiment of the invention includes nucleic acids that encode isoforms of the mouse or human RAPT1, especially isoforms (e.g. splicing variants, allelic variants, etc.) that are capable of binding with the FKBP12/rapamycin complex. Such isoforms, as well as other members of the larger family of RAP-binding proteins, can be isolated using the drug-dependent interaction trap assays described in further detail below.

Another aspect of the invention provides a nucleic acid that hybridizes under high or low stringency conditions to a nucleic acid which encodes a peptide having at least a portion of an amino acid sequence represented by one of SEQ ID Nos.: 2, 12, 14 or 24. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids having a sequence which differs from the nucleotide sequence shown in any of SEQ ID Nos: 1, 11, 13 or 23 due to degeneracy in the genetic code are also within the scope of the invention. Such nucleic acids encode functionally equivalent peptides (i.e., a peptide having a biological activity of a RAP-binding protein) but that differ in sequence from the appended sequence listings due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of the RAP-binding protein. However, it is expected that DNA sequence polymorphisms that do lead to changes in the amino acid sequences of the subject RAP-binding proteins will exist among vertebrates. One skilled in the art will appreciate that these variations in one or more nucleotides (up to about 3–5% of the nucleotides) of the nucleic acids encoding polypeptides having an activity of a RAP-binding protein may exist among individuals of a given species due to natural allelic variation. Any and all such nucleotide variations and resulting amino acid polymorphisms are within the scope of this invention.

The present invention also provides nucleic acid encoding only a portion of a RAPT1 protein, such as the rapamycin-binding domain. As used herein, a fragment of a nucleic acid encoding such a portion of a RAP-binding protein refers to a nucleotide sequence having fewer nucleotides than the nucleotide sequence encoding the entire amino acid sequence of a full-length RAP-binding protein, yet which still includes enough of the coding sequence so as to encode a polypeptide which is capable of binding to an FKBP/rapamycin complex. Moreover, nucleic acid fragments within the scope of the invention include those fragments capable of hybridizing under high or low stringency conditions with nucleic acids from other vertebrate species, particularly other mammals, and can be used in screening protocols to detect homologs, of the subject RAP-binding proteins. Nucleic acids within the scope of the invention may also contain linker sequences, modified restriction endonuclease sites and other sequences useful for molecular cloning, expression or purification of recombinant peptides derived from RAP-binding proteins.

As indicated by the examples set out below, a nucleic acid encoding a RAP-binding protein may be obtained from mRNA present in any of a number of cells from a vertebrate organism, particularly from mammals, e.g. mouse or human. It should also be possible to obtain nucleic acids encoding RAP-binding proteins from genomic DNA obtained from both adults and embryos. For example, a gene encoding a RAP-binding protein can be cloned from either a cDNA or a genomic library in accordance with protocols herein described, as well as those generally known in the art. For instance, a cDNA encoding a RAPT1 protein, particularly other isoforms of the RAPT1 proteins represented by either SEQ ID No. 2 or 12, can be obtained by isolating total mRNA from a mammalian cell, e.g. a human cell, generating double stranded cDNAs from the total mRNA, cloning the cDNA into a suitable plasmid or bacteriophage vector, and isolating RAPT1 clones using any one of a number of known techniques, e.g. oligonucleotide probes or western blot analysis. Genes encoding proteins related to the subject RAP-binding proteins can also be cloned using established polymerase chain reaction techniques in accordance with the nucleotide sequence information provided by the invention. The nucleic acid of the invention can be DNA or RNA.

Another aspect of the invention relates to the use of the isolated nucleic acid in "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding a RAP-binding protein so as to inhibit expression of that protein, as for example by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a RAP-binding protein. Alternatively, the antisense construct can be an oligonucleotide probe which is generated ex vivo and which, when introduced into the cell causes inhibition of expression by hybridizing with the mRNA and/or genomic sequences of a RAP-BP gene. Such oligonucleotide probes are preferably modified oligonucleotides which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al. (1988) Biotechniques 6:958–976; and Stein et al. (1988) Cancer Res 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneuos for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of a RAP-binding protein, can be used in the manipulation of tissue, e.g. tissue proliferation and/or differentiation, both for in vivo and ex vivo tissue culture systems.

This invention also provides expression vectors containing a nucleic acid encoding a RAP-binding protein of the present invention, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of a recombinant RAP-binding protein. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences-sequences that control the expression of a DNA sequence when operatively linked to it may be used in these vectors to express DNA sequences encoding the RAP-binding proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered. In one embodiment, the expression vector includes a recombinant gene encoding a polypeptide which mimics or otherwise agonizes the action of a RAP-binding protein, or alternatively, which encodes a polypeptide that antagonizes the action of an authentic RAP-binding protein. Such expression vectors can be used to transfect cells and thereby produce polypeptides, including fusion proteins, encoded by nucleic acids as described herein.

Moreover, the gene constructs of the present invention can also be used as a part of a gene therapy protocol to deliver nucleic acids encoding either an agonistic or antagonistic form of one or more of the subject RAP-binding proteins. Thus, another aspect of the invention features expression vectors for in vivo transfection and expression of a RAP-binding protein in particular cell types so as to reconstitute the function of, or alternatively, abrogate the function of one or more of the subject RAP-binding proteins in a cell in which that protein or other transcriptional regulatory proteins to which it bind are misexpressed. For example, gene therapy can be used to deliver a gene encoding a rapamycin-insensitive RAP-binding protein in order to render a particular tissue or cell-type resistant to rapamycin induced cell-cycle arrest.

Expression constructs of the subject RAP-binding proteins, and mutants thereof, may be administered in any biologically effective carrier, e.g. any formulation or composition capable of effectively delivering the RAP-BP gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of RAP-BP expression are also useful for in vitro transduction of cells, such as in diagnostic assays.

A preferred approach for in vivo introduction of nucleic acid into a cell is by use of a viral vector containing nucleic acid, e.g. a cDNA, encoding the particular form of the RAP-binding protein desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding one of the subject receptors rendering the retrovirus replication defective.

The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including lymphocytes, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci USA* 89:10892–10895; Hwu et al. (1993) *J. Immunol.* 150:4104–4115; U.S. Pat. Nos. 4,868,116; 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue-or cell-specific transcriptional regulatory sequences which control expression of the RAP-BP gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109–127). Expression of the inserted RAP-BP gene can be under control of, for example, the E1A promoter, the major late promoter (MLP) and associated leader sequences, the E3 promoter, or exogenously added promoter sequences.

Yet another viral vector system useful for delivery of the subject RAP-BP gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol* 51:611–619; and Flotte et al. (1993) *J. Biol Chem.* 268:3781–3790).

In addition to viral transfer methods, such as those illustrated above, non-viral methods can also be employed to cause expression of an RAP-binding protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject RAP-BP gene by the targeted cell. Exemplary gene delivery systems of this type include liposomal derived systems, poly-lysine conjugates, and artificial viral envelopes.

In a representative embodiment, a gene encoding one of the subject RAP-binding proteins can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075). For example, lipofection of cells can be carried out using liposomes tagged with monoclonal antibodies against any cell surface antigen present on, for example, T-cells.

In clinical settings, the gene delivery systems for the therapeutic RAP-BP gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Another aspect of the present invention concerns recombinant RAP-binding proteins which are encoded by genes derived from eukaryotic cells, e.g. mammalian cells, e.g. cells from humans, mice, rats, rabbits, or pigs. The term "recombinant protein" refers to a protein of the present invention which is produced by recombinant DNA techniques, wherein generally DNA encoding, for example, the RAPT1 protein, is inserted into a suitable expression vector which is in turn used to transform a host cell to produce the heterologous protein. Moreover, the phrase "derived from", with respect to a recombinant gene encoding the recombinant RAP-binding protein, is meant to include within the meaning of "recombinant protein" those proteins having an amino acid sequence of a native RAP-binding protein, or an amino acid sequence similar thereto, which is generated by mutation so as to include substitutions and/or deletions relative to a naturally occurring form of the RAP-binding protein of a organism. Recombinant RAPT1 proteins preferred by the present invention, in addition to those having an amino acid sequence of a native RAPT1 protein, comprise amino acid sequences which are at least 70% homologous, more preferably 80% homologous and most preferably 90% homologous with an amino acid sequence shown in one of SEQ ID No: 2, 12 or 14. A polypeptide having a biological activity of a RAPT1 protein and which comprises an amino acid sequence that is at least about 95%, more preferably at least about 98%, and most preferably are identical to a sequence represented in one of SEQ ID No: 2, 12 or 14 are also within the scope of the invention.

Likewise, preferred embodiments of recombinant rap-UBC proteins include an amino acid sequence which is at least 70% homologous, more preferably 80% homologous, and most preferably 90% homologous with an amino acid sequence represented by SEQ ID No. 24. Recombinant rap-UBC proteins which are identical, or substantially identical (e.g. 95 to 98% homologous) with an amino acid sequence of SEQ ID No. 24 are also specifically contemplated by the present invention.

In addition, the invention expressly encompasses recombinant RAPT1 proteins produced from the ATCC deposited clones described in Example 4, e.g. from ATCC deposit number 75787, as well as recombinant ubiquitin-conjugating enzymes produced from ATCC deposit number 75786, described in Example 5.

The present invention further pertains to recombinant forms of the subject RAP-binding proteins which are evolutionarily related to a RAP-binding protein represented in one of SEQ ID No: 2, 12 or 24, that is, not identical, yet which are capable of functioning as an agonist or an antagonist of at least one biological activity of a RAP-binding protein. The term "evolutionarily related to", with respect to amino acid sequences of recombinant RAP-binding proteins, refers to proteins which have amino acid sequences that have arisen naturally, as well as to mutational variants which are derived, for example, by recombinant mutagenesis.

Another aspect of the present invention pertains to methods of producing the subject RAP-binding proteins. For example, a host cell transfected with a nucleic acid vector directing expression of a nucleotide sequence encoding the subject RAPT1 protein or rap-UBC can be cultured under appropriate conditions to allow expression of the peptide to occur. The peptide may be secreted and isolated from a mixture of cells and medium containing the recombinant protein. Alternatively, the peptide may be retained cytoplasmically, as the naturally occurring forms of the subject RAP-binding proteins are believed to be, and the cells harvested, lysed and the protein isolated. A cell culture includes host cells, media and other byproducts. Suitable media for cell culture are well known in the art. The recombinant RAP-binding proteins can be isolated from cell culture medium, host cells, or both using techniques known in the art for purifying proteins including ion-exchange chromatography, gel filtration chromatography, ultrafiltration, electrophoresis, and immunoaffinity purification with antibodies specific for a RAP-binding protein. In one embodiment, the RAP-binding protein is a fusion protein containing a domain which facilitates its purification, such as a RAPT1-GST fusion protein or a rapUBC-GST fusion protein.

The present invention also provides host cells transfected with a RAP-BP gene for expressing a recombinant form of a RAP-binding protein. The host cell may be any prokaryotic or eukaryotic cell. Thus, a nucleotide sequence derived from the cloning of the RAP-binding proteins of the present invention, encoding all or a selected portion of a protein, can be used to produce a recombinant form of a RAP-BP via microbial or eukaryotic cellular processes. Ligating a polynucleotide sequence into a gene construct, such as an expression vector, and transforming or transfecting host cells with the vector are standard procedures used in producing other well-known proteins, e.g. insulin, interferons, p53, myc, cyclins and the like. Similar procedures, or modifications thereof, can be employed to prepare recombinant RAP-binding proteins, or portions thereof, by microbial means or tissue-culture technology in accord with the subject invention. Host cells suitable for expression of a recombinant RAP-binding protein can be selected, for example, from amongst eukaryotic (yeast, avian, insect or mammalian) or prokaryotic (bacterial) cells.

The recombinant RAP-BP gene can be produced by ligating nucleic acid encoding a RAP-binding protein, or a portion thereof, into a vector suitable for expression in either prokaryotic cells, eukaryotic cells, or both. Expression vectors for production of recombinant forms of RAP-binding proteins include plasmids and other vectors. For instance, suitable vectors for the expression of a RAP-BP include plasmids of the types: pBR322-derived plasmids, pEMBL-derived plasmids, pEX-derived plasmids, pBTac-derived plasmids and pUC-derived plasmids for expression in prokaryotic cells, such as $E.\ coli$.

A number of vectors exist for the expression of recombinant proteins in yeast. For instance, YEP24, YIP5, YEP51, YEP52, pYES2, and YRP17 are cloning and expression vehicles useful in the introduction of genetic constructs into $S.\ cerevisiae$ (see, for example, Broach et al. (1983) in Experimental Manipulation of Gene Expression, ed. M. Inouye Academic Press, p. 83, incorporated by reference herein). These vectors can replicate in $E.\ coli$ due the presence of the pBR322 ori, and in $S.\ cerevisiae$ due to the replication determinant of the yeast 2 micron plasmid. In addition, drug resistance markers such as ampicillin can be used.

Preferred mammalian expression vectors contain prokaryotic sequences to facilitate the propagation of the vector in bacteria, and one or more eukaryotic transcription regulatory sequences that cause expression of a recombinant RAP-BP gene in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found above in the description of gene therapy delivery systems.

In some instances, it may be desirable to express a recombinant RAP-binding protein by the use of a baculovirus expression system (see, for example, Current Protocols in Molecular Biology, eds. Ausubel et al. John Wiley & Sons: 1992). Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

When expression of a portion of one of the subject RAP-binding proteins is desired, i.e. a trunction mutant, such as the RAPT1 polypeptides of SEQ ID Nos. 2, 12 or 14, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from $E.\ coli$ (Ben-Bassat et al. (1987) $J.\ Bacteriol.$ 169:751–757) and Salmonella typhimurium and its in vitro activity has been demonstrated on recombinant proteins (Miller et al. (1987) PNAS 84:2718–1722). Therefore, removal of an N-terminal methionine, if desired, can be achieved either in vivo by expressing RAP-BP-derived polypeptides in a host which produces MAP (e.g., $E.$

*coli* or CM89 or *S. cerevisiae*), or in vitro by use of purified MAP (e.g., procedure of Miller et al., supra).

Alternatively, the coding sequences for the polypeptide can be incorporated as a part of a fusion gene so as to be covalently linked in-frame with a second nucleotide sequence encoding a different polypeptide. This type of expression system can be useful, for instance, where it is desirable to produce an immunogenic fragment of a RAP-binding protein. For example, the VP6 capsid protein of rotavirus can be used as an immunologic carrier protein for portions of the RAPT1 polypeptide, either in the monomeric form or in the form of a viral particle. The nucleic acid sequences corresponding to the portion of the RAPT1 protein to which antibodies are to be raised can be incorporated into a fusion gene construct which includes coding sequences for a late vaccinia virus structural protein to produce a set of recombinant viruses expressing fusion proteins comprising a portion of the protein RAPT1 as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an RAPT1 protein and the poliovirus capsid protein can be created to enhance immunogenicity of the set of polypeptide antigens (see, for example, EP Publication No. 0259149; and Evans et al. (1989) *Nature* 339:385; Huang et al. (1988) *J. Virol.* 62:3855; and Schlienger et al. (1992) *J. Virol* 66:2). The subject ubiquitin-conjugating enzyme can be manipulated as an immunogen in like fashion.

The Multiple Antigen Peptide system for peptide-based immunization can also be utilized, wherein a desired portion of a RAP-binding protein is obtained directly from organochemical synthesis of the peptide onto an oligomeric branching lysine core (see, for example, Posnett et al. (1988) *JBC* 263:1719 and Nardelli et al. (1992) *J. Immunol.* 148:914). Antigenic determinants of the RAP-binding proteins can also be expressed and presented by bacterial cells.

In addition to utilizing fusion proteins to enhance immunogenicity, it is widely appreciated that fusion proteins can also facilitate the expression and purification of proteins, such as any one of the RAP-binding proteins of the present invention. For example, a RAP-binding protein can be generated as a glutathione-S-transferase (GST) fusion protein. Such GST fusion proteins can simplify purification of a RAP-binding protein, as for example by affinity purification using glutathione-derivatized matrices (see, for example, *Current Protocols in Molecular Biology*, eds. Ausabel et al. (N.Y.: John Wiley & Sons, 1991)). In another embodiment, a fusion gene coding for a purification leader sequence, such as a peptide leader sequence comprising a poly-(His)/enterokinase cleavage sequence, can be added to the N-terminus of the desired portion of a RAP-binding protein in order to permit purification of the poly(His)-fusion protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which are subsequently annealed to generate a chimeric gene sequence (see, for example, *Current Protocols in Molecular Biology*, eds. Ausubel et al. John Wiley & Sons: 1992).

The present invention also makes available purified, or otherwise isolated forms of the subject RAP-binding proteins which is isolated from, or otherwise substantially free of other cellular proteins, especially FKBP or other rapamycin binding proteins, as well as ubiquitin and ubiquitin-dependent enzymes, signal transduction, and cell-cycle regulatory proteins, which may be normally associated with the RAP-binding protein. The term "substantially free of other cellular or viral proteins" (also referred to herein as "contaminating proteins") or "substantially pure or purified preparations" are defined as encompassing preparations of RAP-binding proteins having less than 20% (by dry weight) contaminating protein, and preferably having less than 5% contaminating protein. Functional forms of the subject RAP-binding proteins can be prepared, for the first time, as purified preparations by using recombinant proteins as described herein. Alternatively, the subject RAP-binding proteins can be isolated by affinity purification using, for example, matrix bound FKBP/rapamycin protein. By "purified", it is meant, when referring to a peptide or DNA or RNA sequence, that the indicated molecule is present in the substantial absence of other biological macromolecules, such as other proteins (particularly FK506 binding proteins, as well as other contaminating proteins). The term "purified" as used herein preferably means at least 80% by dry weight, more preferably in the range of 95–99% by weight, and most preferably at least 99% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

Furthermore, isolated peptidyl portions of the subject RAP-binding proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a RAP-binding protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a RAP-binding protein activity, such as by microinjection assays or in vitro protein binding assays. In an illustrative embodiment, peptidyl portions of a RAP-binding protein, such as RAPT1 or rapUBC, can be tested for FKBP/rapamycin-binding activity.

It will also be possible to modify the structure of a RAP-binding protein for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the RAP-binding protein described in more detail herein. Such modified peptide can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the folding of the protein, and may or may not have much of an effect on the biological activity of the resulting molecule. Conservative replacements are those that take place within a family of amino acids that are related in their side chains. Genetically encoded amino acids are can be divided into four families: (1) acidic aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic= glycine, alanine, valine, leucine, isoleucine, serine, threonine, with serine and threonine optionally be grouped separately as aliphatic-hydroxyl; (4) aromatic= phenylalanine, tyrosine, tryptophan; (5) amide=asparagine, glutamine; and (6) sulfur -containing=cysteine and methionine (see, for example, *Biochemistry*, 2nd ed., Ed. by L. Stryer, W H Freeman and Co.: 1981). Alternatively, amino acid replacement can be based on steric criteria, e.g. isosteric replacements, without regard for polarity or charge of amino acid sidechains. Whether a change in the amino acid sequence of a peptide results in a functional RAP-BP homolog (e.g. functional in the sense that it acts to mimic or antagonize the wild-type form) can be readily determined by assessing the ability of the variant peptide to produce a response in cells in a fashion similar to the wild-type RAP-BP or competitively inhibit such a response. Peptides in which more than one replacement has taken place can readily be tested in the same manner.

This invention further contemplates a method of generating sets of combinatorial mutants of RAP-binding proteins, e.g. of RAPT1 proteins and/or rap-UBC enzymes, as well as truncation mutants, thereof and is especially useful for identifying variant sequences (e.g RAP-BP homologs) that are functional in regulating rapamycin-mediated effects, as well as other aspects of cell growth or differentiation. In similar fashion, RAP-BP homologs can be generated by the present combinatorial approach which are antagonists in that they are able to interfere with the normal cellular functions of authentic forms of the protein.

One purpose for screening such combinatorial libraries is, for example, to isolate novel RAP-BP homologs from the library which function in the capacity as one of either an agonists or an antagonist of the biological activities of the wild-type ("authentic") protein, or alternatively, which possess novel biological activities all together. To illustrate, RAPT1 homologs can be engineered by the present method to provide homologs which are unable to bind to the FKBP/rapamycin complex, yet still retain at least a portion of the normal cellular activity associated with authentic RAPT1. Thus, combinatorially-derived homologs can be generated to provide rapamycin-resistance. Such proteins, when expressed from recombinant DNA constructs, can be used in gene therapy protocols.

Likewise, mutagenesis can give rise to RAP-BP homologs which have intracellular half-lives dramatically different than the corresponding wild-type protein. For example, the altered protein can be rendered either more stable or less stable to proteolytic degradation or other cellular process which result in destruction of, or otherwise inactivation of, the authentic RAP-binding protein. Such homologs, and the genes which encode them, can be utilized to alter the envelope of expression of a particular RAP-BP by modulating the half-life of the protein. For instance, a short half-life can give rise to more transient RAPT1 biological effects and, when part of an inducible expression system, can allow tighter control of recombinant RAPT1 levels within the cell. As above, such proteins, and particularly their recombinant nucleic acid constructs, can be used in gene therapy protocols.

In an illustrative embodiment of this method, the amino acid sequences for a population of RAP-BP homologs, or other related proteins, are aligned, preferably to promote the highest homology possible. Such a population of variants can include, for example, RAPT1 homologs from one or more species, e.g. a sequence alignment of the mouse and human RAPT1 proteins represented by SEQ ID Nos. 2 and 12, or different RAP-BP isoforms from the same species, e.g. different human RAPT1 isoforms. Amino acids which appear at each position of the sequence alignment can be selected to create a degenerate set of combinatorial sequences.

In a preferred embodiment, the combinatorial RAP-BP library is produced by way of a degenerate library of genes encoding a library of polypeptides which each include at least a portion of potential RAP-BP sequences, e.g. the portion of RAPT1 represented by SEQ ID No:2 or 12, or the portion of rap-UBC represented by SEQ ID No. 24. A mixture of synthetic oligonucleotides can be enzymatically ligated into gene sequences such that the degenerate set of potential RAP-BP sequences are expressible as individual polypeptides, or alternatively, as a set of larger fusion proteins (e.g. for phage display) containing the RAP-BP sequence library therein.

There are many ways by which the library of RAP-BP homologs can be generated from a degenerate oligonucleotide sequence. For instance, chemical synthesis of a degenerate gene sequence can be carried out in an automated DNA synthesizer, and the synthetic genes then ligated into an appropriate gene for expression. The purpose of a degenerate set of RAP-BP genes is to provide, in one mixture, all of the sequences encoding the desired set of potential RAP-BP sequences. The synthesis of degenerate oligonucleotides is well known in the art (see, for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Alternatively, other forms of mutagenesis can be utilized to generate a combinatorial library. For example, RAP-BP homologs (both agonist and antagonist forms) can be generated and isolated from a library generated by using, for example, alanine scanning mutagenesis and the like (Ruf et al. (1994) *Biochemistry* 33:1565–1572; Wang et al. (1994) *J. Biol. Chem.* 269:3095–3099; Balint et al. (1993) *Gene* 137:109–118; Grodberg et al. (1993) *Eur. J. Biochem.* 218:597–601; Nagashima et al. (1993) *J. Biol. Chem.* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol. Cell Biol.* 12:2644–2652; McKnight et al. (1982) *Science* 232:316); by saturation mutagenesis (Meyers et al. (1986) *Science* 232:613); by PCR mutagenesis (Leung et al. (1989) *Method Cell Mol Biol* 1:11–19); or by random mutagenesis (Miller et al. (1992) *A Short Course in Bacterial Genetics*, CSHL Press, Cold Spring Harbor, N.Y.; and Greener et al. (1994) *Strategies in Mol Biol* 7:32–34).

A wide range of techniques are known in the art for screening gene products of variegated gene libraries made by combinatorial mutagenesis, especially for identifying individual gene products having a certain property. Such techniques will be generally adaptable for rapid screening of the gene libraries generated by the combinatorial mutagenesis of, for example, RAPT1 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate RAP-BP sequences created by combinatorial mutagenesis techniques.

In one screening assay, the candidate RAP-BP gene products are displayed on the surface of a cell or viral particle, and the ability of particular cells or viral particles to bind the FKBP12/rapamycin complex via this gene product is detected in a "panning assay". For instance, the degenerate RAP-BP gene library can be cloned into the gene for a surface membrane protein of a bacterial cell, and the resulting fusion protein detected by panning protocols (see, for example, Ladner et al., WO 88/06630; Fuchs et al. (1991) *Bio/Technology* 9:1370–1371; and Goward et al. (1992) *TIBS* 18:136–140). In a similar fashion, fluorescently labeled molecules which bind the RAP-binding protein, such as fluorescently labeled rapamycin or FKBP12/rapamycin complexes, can be used to score for potentially functional RAP-BP homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461). In an illustrative embodiment, the recombinant phage antibody system (RPAS, Pharmacia Catalog number 27-9400-01) can be easily modified for use in expressing and screening RAP-BP combinatorial libraries, and the RAP-BP phage library can be panned on glutathione-immobilized FKBP-GST/rapamycin complexes. Successive rounds of reinfection, phage amplification, and panning will greatly enrich for homologs which retain FKBP/rapamycin binding and which can be subsequently screened for further biological activities in order to discern between agonists and antagonists.

Homologs of the human and mouse RAP-binding proteins can also be generated through the use of interaction trap assays to screen combinatorial libraries of RAP-BP mutants. As described in Example 10 below, the same two hybrid assay used to screen cDNA libraries for proteins which interact with FK506-binding proteins in a drug-dependent manner can also be used to sort through combinatorial libraries of, for example, RAPT1 mutants, to find both agonistic and antagonistic forms. By controlling the sensitivity of the assay for inteactions, e.g. through the manipulation of the strength of the promoter sequence used to drive expression of the reporter construct, the assay can be generated to favor agonistic forms of RAPT1 with tighter binding affinities for rapamycin then the authentic form of the protein. Alternatively, as described in Example 10, the assay can be used to select for RAPT1 homologs which are now unable to bind rapamycin complexes and hence are versions of the RAPT1 protein which can render a cell insensitive to treatment with that macrolide.

The invention also provides for reduction of the rapamycin-binding domains of the subject RAP-binding proteins to generate mimetics, e.g. peptide or non-peptide agents, which are able to disrupt binding of a polypeptide of the present invention with an FKBP/rapamycin complex. Thus, such mutagenic techniques as described above are also useful to map the determinants of RAP-binding proteins which participate in interactions involved in, for example, binding to an FKBP/rapamycin complex. To illustrate, the critical residues of a RAP-binding protein which are involved in molecular recognition of FKBP/rapamycin can be determined and used to generate RAP-BP-derived peptidomimetics that competitively inhibit binding of the RAP-BP to rapamycin complexes. By employing, for example, scanning mutagenesis to map the amino acid residues of a particular RAP-binding protein involved in binding FKBP/rapamycin complexes, peptidomimetic compounds can be generated which mimic those residues in binding to the rapamycin complex, and which, by inhibiting binding of the RAP-BP to FKBP/rapamycin, can interfere with the function of rapamycin in cell-cycle arrest. For instance, non-hydrolyzable peptide analogs of such residues can be generated using retro-inverse peptides (e.g., see U.S. Pat. Nos. 5,116,947 and 5,218,089; and Pallai et al. (1983) *Int J Pept Protein Res* 21:84–92) benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in

*Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Communl*26:419; and Dann et al. (1986) *Biochem Biophys Res Commun* 134:71). Utilizing side-by-side assays, peptidomimetics can be designed to specifically inhibit the interaction of human RAPT1 (or other mammalian homologs) with the FKBP12/rapamycin complex in mammalian cells, but which do not substantially affect the interaction of the yeast protein TOR1 or TOR2 with the FKB1/rapamycin complex. Such a peptide analog could be used in conjunction with rapamycin treatment of mycotic infections to protect the host mammal from rapamycin side-effects, such as immunosuppression, without substantially reducing the efficacy of rapamycin as an anti-fungal agent.

Another aspect of the invention pertains to an antibody specifically reactive with one or more of the subject RAP-binding proteins. For example, by using immunogens derived from a RAP-binding protein, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., a full length RAP-binding protein or an antigenic fragment which is capable of eliciting an antibody response). Techniques for conferring immunogenicity on a protein or peptide include conjugation to carriers or other techniques well known in the art. An immunogenic portion of the subject RAP-binding proteins can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the RAP-binding proteins of the present invention, e.g. antigenic determinants of a protein represented in one of SEQ ID Nos: 2, 12 or 24 or a closely related human or non-human mammalian homolog thereof. For instance, a favored anti-RAP-BP antibody of the present invention does not substantially cross react (i.e. react specifically) with a protein which is less than 90 percent homologous to one of SEQ ID Nos: 2, 12 or 24; though antibodies which do not substantially cross react with a protein which is less than 95 percent homologous with one of SEQ ID Nos: 2, 12 or 24, or even less than 98–99 percent homologous with one of SEQ ID Nos: 2, 12 or 24, are specifically contemplated. By "not substantially cross react", it is meant that the antibody has a binding affinity for a non-homologous protein (e.g. a yeast TOR1 or TOR2 protein) which is less than 10 percent, more preferably less than 5 percent, and even more preferably less than 1 percent, of the binding affinity for a protein represented one of SEQ ID Nos: 2, 12 or 24.

Following immunization, anti-RAP-BP antisera can be obtained and, if desired, polyclonal anti-RAP-BP antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature,* 256: 495–497), the human B cell hybridoma technique (Kozbar et al., (1983) *Immunology Today,* 4: 72), and the EBV-hybridoma technique to produce human monoclonal antibodies (Cole et al., (1985) *Monoclonal Antibodies and Cancer Therapy,* Alan R. Liss, Inc. pp. 77–96). Hybridoma cells can be screened immunochemically for production of antibodies specifically reactive with a RAP-binding protein of the present invention and monoclonal antibodies isolated from a culture comprising such hybridoma cells.

An antibody preparation of this invention prepared from a polypeptide as described above can be in dry form as obtained by lyophilization. However, the antibodies are normally used and supplied in an aqueous liquid composition in serum or a suitable buffer such as PBS.

The term antibody as used herein is intended to include fragments thereof which are also specifically reactive with one of the subject RAP-binding protein. Antibodies can be fragmented using conventional techniques, including recombinant engineering, and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments. The antibody of the present invention is further intended to include bispecific and chimeric molecules having an anti-RAP-BP portion.

Both monoclonal and polyclonal antibodies (Ab) directed against a RAP-binding protein can be used to block the action of that protein and allow the study of the role of a particular RAP-binding protein in, for example, cell-cycle regulation generally, or in the etiology of proliferative and/or differentiative disorders specifically, or in the mechanism of action of rapamycin, e.g. by microinjection of anti-RAP-BP antibodies into cells.

Antibodies which specifically bind RAP-BP epitopes can also be used in immunohistochemical staining of tissue samples in order to evaluate the abundance and pattern of expression of each of the subject RAP-binding proteins. Anti-RAP-BP antibodies can be used diagnostically in immuno-precipitation and immuno-blotting to detect and evaluate RAP-BP levels in tissue or bodily fluid as part of a clinical testing procedure. For instance, such measurements as the level of free RAP-BP to RAP-BP/FKBP/drug complexes can be useful in predictive valuations of the efficacy of a particular rapamycin analog, and can permit determination of the efficacy of a given treatment regimen for an individual. The level of a RAP-binding protein can be measured in cells found in bodily fluid, such as in cells from samples of blood, or can be measured in tissue, such as produced by biopsy.

Another application of the subject antibodies is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a RAP-binding protein can then be detected with antibodies, as, for example, reacting nitrocellulose filters lifted from infected plates with anti-RAP-BP antibodies.

Phage, scored by this assay, can then be isolated from the infected plate. Thus, the presence of RAP-BP homologs can be detected and cloned from other animals, and alternate isoforms (including splicing variants) can be detected and cloned from human sources.

Moreover, the nucleotide sequence determined from the cloning of the subject RAP-binding proteins from a human cell line will further allow for the generation of probes designed for use in identifying homologs in other human cell types, as well as RAP-BP homologs (e.g. orthologs) from other mammals. For example, by identifying highly conserved nucleotides sequence through comparison of the mammalian RAPT1 genes with the yeast TOR genes, it will be possible to design degenerate primers for isolating RAPT1 homologs from virtually any eukaryotic cell. For instance, alignment of the mouse RAPT1 gene sequence and the yeast DRR-1 and TOR2 sequences, we have determined that optimal primers for isolating RAPT1 homologs from other mammalian homologs, as well as from pathogenic fungi, include the primers GRGAYTTRAWBGAB-GCHYAMGAWTGG SEQ ID NO: 31, CAAGCBTGG-GAYMTYMTYTAYTATMAYGTBTTCAG SEQ ID NO: 32, and GAYYBGARTTGGCTGTBCCHGG SEQ ID NO: 33.

Accordingly, the present invention also provides a probe/primer comprising a substantially purified oligonucleotide, which oligonucleotide comprises a region of nucleotide sequence that hybridizes under stringent conditions to at least 10 consecutive nucleotides of sense or anti-sense sequence of one of SEQ ID Nos: 1, 11 or 23, or naturally occurring mutants thereof. In preferred embodiments, the probe/primer further comprises a label group attached thereto and able to be detected, e.g. the label group is selected from the group consisting of radioisotopes, fluorescent compounds, enzymes, and enzyme co-factors. Such probes can also be used as a part of a diagnostic test kit for identifying transformed cells, such as for measuring a level of a RAP-BP nucleic acid in a sample of cells from a patient; e.g. detecting mRNA encoding a RAP-BP mRNA level; e.g. determining whether a genomic RAP-BP gene has been mutated or deleted.

In addition, nucleotide probes can be generated which allow for histological screening of intact tissue and tissue samples for the presence of a RAP-BP mRNA. Similar to the diagnostic uses of anti-RAP-BP antibodies, the use of probes directed to RAP-BP mRNAs, or to genomic RAP-BP sequences, can be used for both predictive and therapeutic evaluation of allelic mutations which might be manifest in, for example, neoplastic or hyperplastic disorders (e.g. unwanted cell growth) or abnormal differentiation of tissue. Used in conjunction with an antibody immunoassays, the nucleotide probes can help facilitate the determination of the molecular basis for a developmental disorder which may involve some abnormality associated with expression (or lack thereof) of a RAP-binding protein. For instance, variation in synthesis of a RAP-binding protein can be distinguished from a mutation in the genes coding sequence.

Thus, the present invention provides a method for determining if a subject is at risk for a disorder characterized by unwanted cell proliferation or abherent control of differentiation. In preferred embodiments, the subject method can be generally characterized as comprising detecting, in a tissue sample of the subject (e.g. a human patient), the presence or absence of a genetic lesion characterized by at least one of (i) a mutation of a gene encoding one of the subject RAP-binding proteins or (ii) the mis-expression of a RAP-BP gene. To illustrate, such genetic lesions can be detected by ascertaining the existence of at least one of (i) a deletion of one or more nucleotides from a RAP-BP gene, (ii) an addition of one or more nucleotides to such a RAP-BP gene, (iii) a substitution of one or more nucleotides of a RAP-BP gene, (iv) a gross chromosomal rearrangement of one of the RAP-BP genes, (v) a gross alteration in the level of a messenger RNA transcript of a RAP-BP gene, (vi) the presence of a non-wild type splicing pattern of a messenger RNA transcript of a RAP-BP gene, and (vii) a non-wild type level of a RAP-binding protein. In one aspect of the invention there is provided a probe/primer comprising an oligonucleotide containing a region of nucleotide sequence which is capable of hybridizing to a sense or antisense sequence of one of SEQ ID Nos: 1, 11 or 23, or naturally occurring mutants thereof, or 5' or 3' flanking sequences or intronic sequences naturally associated with the subject RAP-BP genes. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR) (see, e.g., U.S. Pat. Nos: 4,683,195 and 4,683,202) or, alternatively, in a ligation chain reaction (LCR) (see, e.g., Landegran et al. (1988) Science, 241:1077–1080; and NaKazawa et al. (1944) PNAS 91:360–364) the later of which can be particularly useful for detecting point mutations in the RAP-BP gene. Alternatively, immunoassays can be employed to determine the level of RAP-binding protein and/or its participation in protein complexes, particularly transcriptional regulatory complexes such as those involving FKBP/rapamycin.

Also, by inhibiting endogenous production of a particular RAP-binding protein, anti-sense techniques (e.g. microinjection of antisense molecules, or transfection with plasmids whose transcripts are anti-sense with regard to a RAP-BP mRNA or gene sequence) can be used to investigate role of each of the subject RAP-BP in growth and differentiative events, such as those giving rise to Wilm's tumor, as well as normal cellular functions of each of the subject RAP-binding proteins, e.g. in regulation of transcription. Such techniques can be utilized in cell culture, but can also be used in the creation of transgenic animals.

Furthermore, by making available purified and recombinant RAP-binding proteins, the present invention provides for the generation of assays which can be used to screen for drugs which are either agonists or antagonists of the cellular function of each of the subject RAP-binding proteins, or of their role in the pathogenesis of proliferative and differentiative disorders. For instance, an assay can be generated according to the present invention which evaluates the ability of a compound to modulate binding between a RAP-binding protein and an FK506-binding protein. In particular, such assays can be used to design and screen novel rapamycin analogs, as well as test completely unrelated compounds for their ability to mediate formation of FKBP/RAP-BP complexes. Such assays can be used to generate more potent anti-proliferative agents having a similar mechanism of action as rapamycin, e.g. rapamycin analogs. A variety of assay formats will suffice and, in light of the present inventions, will be comprehended by skilled artisan.

One aspect of the present invention which facilitates the generation of drug screening assays, particularly the high-throughout assays described below, is the identification of the rapamycin binding domain of RAPT1-like proteins. For instance, the present invention provides portions of the RAPT-like proteins which are easier to manipulate than the full length protein. The full length protein is, because of its size, more difficult to express as a recombinant protein or a fusion protein which would retain rapamycin-binding activity, and may very well be insoluble. Accordingly, the present invention provides soluble polypeptides which include a soluble portion of a RAPT1-like polypeptide that binds to said FKBP/rapamycin complex, such as the rapamycin-binding domain represented by an amino acid sequence selected from the group consisting Val28-Tyr160 of SEQ ID No. 2, Val1272-Try1404 of SEQ ID No. 12, Val41-Tyr173 of SEQ ID No. 14, Val1-Tyr133 of SEQ ID No. 16, and Val1-Arg133 of SEQ ID No. 18.

For instance, RAPT1 polypeptides useful in the subject screening assays may be represented by the general formula X-Y-Z, Y represents an amino acid sequence of a rapamycin-binding domain within residues 1272 to 1404 of SEQ ID No. 12, X is absent, or represents all or a C-terminal portion of the amino acid sequence between residues 1000 and 1404 of SEQ ID No. 12 not represented by Y, and Z is absent, or represents all or a N-terminal portion of the amino acid sequence between residues 1272 and 1809 of SEQ ID No. 12 not represented by Y. Preferably, the polypeptide includes only about 50 to 200 residues of RAPT1 protein sequence. Similar polypeptides can be generated for other RAPT1-like proteins.

Moreover, the same formula can also be used to designate a fusion protein, wherein Y represents a rapamycin-binding domain within residues 1272 to 1404 of SEQ ID No. 12, X is absent or represents a polypeptide from 1 to about 500 amino acid residues of SEQ ID No. 12 immediately N-terminal to the rapamycin-binding domain, and Z is absent or represents from 1 to about 365 amino acid residues of SEQ ID No. 2 immediately C-terminal to the rapamycin-binding domain.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target when contacted with a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. Accordingly, in an exemplary screening assay of the present invention, the compound of interest (the "drug") is contacted with a mixture generated from an isolated and purified RAP-binding protein, such as RAPT1 or rapUBC, and an FK506-binding protein. Detection and quantification of drug-depedent FKBP/RAP-BP complexes provides a means for determining the compound's efficacy for mediating complex formation between the two proteins. The efficacy of the compound can be assessed by generating dose response curves from data obtained using various concentrations of the test compound. Moreover, a control assay can also be performed to provide a baseline for comparison. In the control assay, isolated and purified RAP-BP is added to a composition containing the FK506-binding protein, and the formation of FKBPRAP-BP complexes is quantitated in the absence of the test compound.

Complex formation between the RAP-binding protein and an FKBP/drug complex may be detected by a variety of techniques. For instance, modulation in the formation of complexes can be quantitated using, for example, detectably labelled proteins (e.g. radiolabelled, fluorescently labelled, or enzymatically labelled), by immunoassay, or by chromatographic detection.

Typically, it will be desirable to immobilize either the FK506-binding protein or the RAP-binding protein to facilitate separation of drug-dependent protein complexes from uncomplexed forms of one of the proteins, as well as to accommodate automation of the assay. In an illustrative embodiment, a fusion protein can be provided which adds a domain that permits the protein to be bound to an insoluble matrix. For example, glutathione-S-transferase/FKBP (FKBP-GST) fusion proteins can be adsorbed onto glutathione sepharose beads (Sigma Chemical, St. Louis, Mo.) or glutathione derivatized microtitre plates, which are then combined with the RAP-binding protein, e.g. an $^{35}$S-labeled RAP-binding protein, and the test compound and incubated under conditions conducive to complex formation (see, for instance, Example 9). Following incubation, the beads are washed to remove any unbound RAP-BP, and the matrix bead-bound radiolabel determined directly (e.g. beads placed in scintilant), or in the superntantant after the FKBP/RAP-BP complexes are dissociated, e.g. when microtitre plates are used. Alternatively, after washing away unbound protein, the complexes can be dissociated from the matrix, separated by SDS-PAGE gel, and the level of RAP-BP found in the matrix-bound fraction quantitated from the gel using standard electrophoretic techniques.

Other techniques for immobilizing proteins on matrices are also available for use in the subject assay. For instance, the FK506-binding protein can be immobilized utilizing conjugation of biotin and streptavidin. Biotinylated FKBP can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the FKBP can be derivatized to the wells of the plate, and FKBP trapped in the wells by antibody conjugation. As above, preparations of a RAP-binding protein and a test compound are incubated in the FKBP-presenting wells of the plate, and the amount of FKBP/RAP-BP complex trapped in the well can be quantitated. Exemplary methods for detecting such complexes, in addition to those described above for the GST-immobilized complexes, include immunodetection of complexes using antibodies reactive with the RAP-binding protein, or which are reactive with the FK506-binding protein and compete for binding with the RAP-BP; as well as enzyme-linked assays which rely on detecting an enzymatic activity associated with the RAP-binding protein. In the instance of the latter, the enzymatic activity can be endogenous, such as a kinase (RAPT1 ) or ubiquitin ligase (rapUBC) activity, or can be an exogenous activity chemically conjugated or provided as a fusion protein with the RAP-binding protein. To illustrate, the RAP-binding protein can be chemically cross-linked with alkaline phosphatase, and the amount of RAP-BP trapped in the complex can be assessed with a chromogenic substrate of the enzyme, e.g. paranitrophenyl phosphate. Likewise, a fusion protein comprising the RAP-BP and glutathione-S-transferase can be provided, and complex formation quantitated by detecting the GST activity using 1-chloro-2,4-dinitrobenzene (Habig et al (1974) *J Biol Chem* 249:7130).

For processes which rely on immunodetection for quantitating one of the proteins trapped in the complex, antibodies against the protein, such as the anti-RAP-BP antibodies described herein, can be used. Alternatively, the protein to be detected in the complex can be "epitope tagged" in the form of a fusion protein which includes, in addition to the RAP-BP or FKBP sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, N.J.).

Additionally, the subject RAP-binding proteins can be used to generate a drug-dependent interaction trap assay, as described in the examples below, for detecting agents which induce complex formation between a RAP-binding protein and an FK506-binding protein. As described below, the interaction trap assay relies on reconstituting in vivo a functional transcriptional activator protein from two separate fusion proteins, one of which comprises the DNA-binding domain of a transcriptional activator fused to an FK506-binding protein (see also U.S. Pat. No: 5,283,317; PCT publication WO94/10300; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696). The second fusion protein comprises a transcriptional activation domain (e.g. able to initiate RNA polymerase transcription) fused to one of the subject RAP-binding proteins. When the FKBP and RAP-binding protein interact in the presence of an agent such as rapamycin, the two domains of the transcriptional activator protein are brought into sufficient proximity as to cause transcription of a reporter gene. In addition to the LexA interaction trap described in the examples below, yet another illustrative embodiment comprises *Saccharomyces cerevisiae* YPB2 cells transformed simultaneously with a plasmid encoding a GAL4db-FKBP fusion (db: DNA binding domain) and with a plasmid encoding the GAL4 activation domain (GAL4ad) fused to a subject RAP-BP. Moreover, the strain is transformed such that the GAL4-responsive promoter drives expression of a phenotypic marker. For example, the ability to grow in the absence of histidine can depends on the expression of the HIS3 gene. When the HIS3 gene is placed under the control of a GAL4-responsive promoter, relief of this auxotrophic phenotype indicates that a functional GAL4 activator has been reconstituted through the drug-dependent interaction of FKBP and the RAP-BP. Thus, agent able to promote RAP-BP interaction with an FKBP will result in yeast cells able to grow in the absence of histidine. Commercial kits which can be modified to develop two-hybrid assays with the subject RAP-binding proteins are presently available (e.g., MATCHMAKER kit, ClonTech catalog number K1605-1, Palo Alto, Calif.).

In a preferred embodiment, assays which employ the subject mammalian RAP-binding proteins can be used to identify rapamycin mimetics that have therapeutic indexes more favorable than rapamycin. For instance, rapamycin-like drugs can be identified by the present invention which have enhanced tissue-type or cell-type specficity relative to rapamycin. To illustrate, the subject assays can be used to generate compounds which preferentially inhibit IL-2 mediated proliferation/activation of lymphocytes without substantially interfering with other tissues, e.g. hepatocytes. Likewise, similar assays can be used to identify rapamycin-like drugs which inhibit proliferation of yeast cells or other lower eukaryotes, but which have a substantially reduced effect on mammalian cells, thereby improving therapeutic index of the drug as an anti-mycotic agent relative to rapamycin.

In one embodiment, the identification of such compounds is made possible by the use of differential screening assays which detect and compare drug-mediated formation of two or more different types of FKBP/RAP-BP complexes. To illustrate, the assay can be designed for side-by-side comparison of the effect of a test compound on the formation of tissue-type specific FKBP/RAPT1 complexes. Given the diversity of FKBPs, and the substantial likelihood that RAPT1 represents a single member of a larger family of related proteins, it is probable that different functional FKBP/RAPT1 complexes exist and, in certain instances, are localized to particular tissue or cell types. As described in PCT publication WO93/23548, entitled "*Method of Detecting Tissue-Specific FK506 Binding Protein Messenger RNAs and Uses Thereof*", the tissue distribution of FKBPs can vary from one species of the protein to the next. Thus, test compounds can be screened for agents able to mediate the tissue-specific formation of only a subset of the possible repertoire of FKBP/RAPT1 complexes. In an exemplary embodiment, an interaction trap assay can be derived using two or more different bait proteins, e.g. FKBP12 (SEQ ID Nos. 5 and 6), FKBP25 (GenBank Accession M90309), or FKBP52 (Genbank Accession M88279), while the fish protein is constant in each, e.g. a human RAPT1 construct. Running the ITS side-by-side permits the detection of agents which have a greater effect (e.g. statistically significant on the formation of one of the FKBP/RAPT1 complexes than on the formation of the other FKBP complexes.

In similar fashion, differential screening assays can be used to exploit the difference in drug-mediated formation of mammalian FKBP/RAP-BP complexes and yeast FKBP/TOR complexes in order to identify agents which display a statistically significant increase in specificity for the yeast complexes relative to the mammalian complexes. Thus, lead compounds which act specifically on pathogens, such as fungus involved in mycotic infections, can be developed. By way of illustration, the present assays can be used to screen for agents which may ultimately be useful for inhibiting at least one fungus implicated in such mycosis as candidiasis, aspergillosis, mucormycosis, blastomycosis, geotrichosis, cryptococcosis, chromoblastomycosis, coccidioidomycosis, conidiosporosis, histoplasmosis, maduromycosis, rhinosporidosis, nocaidiosis, para-actinomycosis, penicilliosis, monoliasis, or sporotrichosis. For example, if the mycotic infection to which treatment is desired is candidiasis, the present assay can comprise comparing the relative effectiveness of a test compound on mediating formation of a mammalian FKBP/RAPT1 complex with its effectiveness towards mediating such complexes formed from genes cloned from yeast selected from the group consisting of *Candida albicans, Candida stellatoidea, Candida tropicalis, Candida parapsilosis, Candida krusei, Candida pseudotropicalis, Candida quillermondii*, or *Candida rugosa*. Likewise, the present assay can be used to identify anti-fungal agents which may have therapeutic value in the treatment of aspergillosis by making use of the subject drug-dependent interaction trap assays derived from FKBP and TOR genes cloned from yeast such as *Aspergillus fumigatus, Aspergillus flavus, Aspergillus niger, Aspergillus nidulans*, or *Aspergillus terreus*. Where the mycotic infection is mucormycosis, the complexes can be derived from yeast such as *Rhizopus arrhizus, Rhizopus oryzae, Absidia corymbifera, Absidia ramosa*, or *Mucor pusillus*. Sources of other rapamycin-dependent complexes for comparison with a mammalian FKBP/RAPT1 complex includes the pathogen *Pneumocystis carinii*. Exemplary FK506-binding proteins from human pathogens and other lower eukaryotes are provided by, for example, GenBank Accession numbers: M84759 (*Candida albican*); U01195, U01198, U01197, U01193, U01188, U01194, U01199 (Neisseria spp.); and M98428 (*Streptomyces chrysomallus*).

In an exemplary embodiment, the differential screening assay can be generated using at least the rapamycin-binding domain of the *Candida albican* RAPT1 protein (see Example 11) and a Candida FK506-binding protein (such as RBP1, GenBank No. M84759, see also Ferrara et al. (1992) *Gene* 113:125–127), or a yeast FK506-binding protein (see Example 8 and FIG. 3). Comparison of formation of human RAPT1 complexes and Candida RAPT1 complexes provides a means for identifying agents which are more selective for the formation of caRAPT1 complexes and, accordingly, likely to be more specific as anti-mycotic agents relative to rapamycin.

Furthermore, inhibitors of the enzymatic activity of each of the subject RAP-binding proteins can be identified using assays derived from measuring the ability of an agent to inhibit catalytic conversion of a substrate by the subject proteins. For example, the ability of the subject RAPT1 proteins to phosphorylate a phosphatidylinositol substrate, such as phosphatidylinositol-4,5-biphosphate (PIP2), in the presence and absence of a candidate inhibitor, can be determined using standard enzymatic assays. Likewise, the ability of the subject ubiquitin-conjugating enzyme to accept ubiquitin (e.g. from an E1:Ub conjugate) or subsequently transfer ubiquitin to a substrate protein, can be readily ascertained in the presence and absence of a candidate inhibitor. Exemplary assays in which the rapUBC enzyme of the present invention can be used are set forth in U.S. patent application Ser. No. 08/176,937, entitled "Assay and Reagents for Detecting Inhibitors of Ubiquitin-dependent Degradation of Cell Cycle Regulatory Proteins", the specification of which was filed Jan. 4, 1994, and U.S. patent application Ser. No. 08/247,904, entitled "Human Ubiquitin Conjugating Enzyme", the specification of which was filed May 23, 1994.

Another aspect of the present invention concerns transgenic animals which are comprised of cells (of that animal) which contain a transgene of the present invention and which preferably (though optionally) express an exogenous RAP-binding protein in one or more cells in the animal. The RAP-BP transgene can encode the wild-type form of the protein, or can encode homologs thereof, including both agonists and antagonists, as well as antisense constructs designed to inhibit expression of the endogenous gene. In preferred embodiments, the expression of the transgene is restricted to specific subsets of cells, tissues or developmental stages utilizing, for example, through the use of cis-acting sequences that control expression in the desired pattern. In the present invention, such mosaic expression of the subject RAP-binding proteins can be essential for many forms of lineage analysis and can additionally provide a means to assess the effects of loss-of-function mutations, which deficiency might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of a subject RAP-binding protein. For example, excision of a target sequence which interferes with the expression of a recombinant RAP-BP gene can be designed to activate expression of that gene. This interference with expression of the protein can result from a variety of mechanisms, such as spatial separation of the gene from a promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a RAP-binding protein can be regulated via regulation of recombinase expression.

Use of the cre/loxP recombinase system to regulate expression of a recombinant RAP-binding protein, such as RAPT1 or rapUBC, requires the construction of a transgenic animal containing transgenes encoding both the Cre recombinase and the subject protein. Animals containing both the Cre recombinase and the recombinant RAP-BP genes can be provided through the construction of "double" transgenic animals. A convenient method for providing such animals is to mate two transgenic animals each containing a transgene, e.g., the RAP-BP gene in one animal and recombinase gene in the other.

One advantage derived from initially constructing transgenic animals containing a transgene in a recombinase-mediated expressible format derives from the likelihood that the subject protein will be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which, for example, an antagonistic RAP-BP transgene is silent will allow the study of progeny from that founder in which disruption of cell-cycle regulation in a particular tissue or at developmental stages would result in, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed using, for example, one of the gene therapy constructs described above. By this method, the RAP-BP transgene could remain silent into adulthood and its expression "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce a RAP-BP transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

Methods of making knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert recombinase target sequences, such that tissue specific and/or temporal control of inactivation of a RAP-BP gene can be controlled as above.

Another aspect of the present invention concerns a novel in vivo method for the isolation of genes encoding proteins which physically interact with a "bait" protein/drug complex. The method relies on detecting the reconstitution of a transcriptional activator in the presence of the drug, particularly wherein the drug is a non-peptidyl small organic molecule (e.g. <2500K), e.g. a macrolide, e.g. rapamycin, FK506 or cyclosporin. In particular, the method makes use of chimeric genes which express hybrid proteins. The first hybrid comprises the DNA-binding domain of a transcriptional activator fused to the bait protein. The second hybrid protein contains a transcriptional activation domain fused to a "fish" protein, e.g. a test protein derived from a cDNA library. If the fish and bait proteins are able to interact in a drug-dependent manner, they bring into close proximity the two domains of the transcriptional activator. This proximity is sufficient to cause transcription of a reporter gene which is operably linked to a transcriptional regulatory site responsive to the transcriptional activator, and expression of the marker gene can be detected and used to score for the interaction of the bait protein/drug complex with another protein.

One advantage of this method is that a multiplicity of proteins can be simultaneously tested to determine whether any interact with the drug/protein complex. For example, a DNA fragment encoding the DNA-binding domain can be fused to a DNA fragment encoding the bait protein in order to provide one hybrid. This hybrid is introduced into the cells carrying the marker gene, and the cells are contacted with a drug which is known to bind the bait protein. For the second hybrid, a library of plasmids can be constructed which may include, for example, total mammalian complementary DNA (cDNA) fused to the DNA sequence encoding the activation domain. This library is introduced into the cells carrying the first hybrid. If any individual plasmid from the test library encodes a protein that is capable of interacting with the drug/protein complex, a positive signal may be obtained by detecting expression of the reporter gene. In addition, when the interaction between the drug complex and a novel protein occurs, the gene for the newly identified protein is readily available.

As illustrated herein, the present interaction trap system is a valuable tool in the identification of novel genes encoding proteins which act at a point in a given signal transduction pathway that is directly upstream or downstream from a particular protein/drug complex. For example, the subject assay can be used to identify the immediate downstream targets of an FKBP/rapamycin complex, or of an FKBP/FK506 complex, or of a cyclophilin/cyclosporin complex. Proteins that interact in a drug-dependent manner with one of such complexes may be identified, and these proteins can be of both diagnostic and therapeutic value.

A first chimeric gene is provided which is capable of being expressed in the host cell, preferably a yeast cell, most preferably *Saccharomyces cerevisiae* or *Schizosaccharomyces pombe*. The host cell contains a detectable gene having a binding site for the DNA-binding domain of the transcriptional activator, such that the gene expresses a marker protein when the marker gene is transcriptionally activated. Such activation occurs when the transcriptional activation domain of a transcriptional activator is brought into sufficient proximity to the DNA-binding domain of the transcriptional activator. The first chimeric gene may be present in a chromosome of the host cell. The gene encodes a chimeric protein which comprises a DNA-binding domain that recognizes the binding site on the marker gene in the host cell and a bait protein which is to be tested for drug-mediated interaction with a second test protein or protein fragment.

A second chimeric gene is provided which is capable of being expressed in the host cell. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid. The second chimeric gene contains a DNA sequence that encodes a second hybrid protein. The second hybrid protein contains a transcriptional activation domain. The second hybrid protein also contains a second test protein or a protein fragment which is to be tested for interaction with the first test protein or protein fragment. Preferably, the DNA-binding domain of the first hybrid protein and the transcriptional activation domain of the second hybrid protein are derived from transcriptional activators having separate DNA-binding and transcriptional activation domains. These separate DNA-binding and transcriptional activation domains are also known to be found in the yeast GAL4 protein, and are also known to be found in the yeast GCN4 and ADR1 proteins. Many other proteins involved in transcription also have separable binding and transcriptional activation domains which make them useful for the present invention. In another embodiment, the DNA-binding domain and the transcriptional activation domain may be from different transcriptional activators. The second hybrid protein is preferably encoded on a library of plasmids that contain genomic, cDNA or synthetically generated DNA sequences fused to the DNA sequence encoding the transcriptional activation domain.

The drug-mediated interaction between the first test protein and the second test protein in the host cell, therefore, causes the transcriptional activation domain to activate transcription of the detectable gene. The method is carried out by introducing the first chimeric gene and the second chimeric gene into the host cell, and contacting the cell with the drug of interest. The host cell is subjected to conditions under which the first hybrid protein and the second hybrid protein are expressed in sufficient quantity for the detectable gene to be activated. The cells are then tested for drug-dependent expression of the detectable gene.

Thus, interactions between a first test protein and a library of proteins can be tested in the presence of the drug of interest, in order to determine which members of the library are involved in the formation of drug-dependent complexes between the first and second protein. For example, the bait protein may be a protein which binds FK506, rapamycin, or cyclosporin, e.g. can be an FKBP or cyclophilin. The second test protein may be derived from a cDNA library.

Exemplification

The invention now being generally described, it will be more readily understood by reference to the following examples which are included merely for purposes of illustration of certain aspects and embodiments of the present invention, and are not intended to limit the invention.

EXAMPLE 1

Construction of the Bait Plasmids for the 2-Hybrid Screen

A. LexA-FKBP12 Bait

The bait protein and fish protein constructs used in the present drug-dependent interaction trap are essentially the same as constructs used for other 2 hybrid assays (see, for example, U.S. Pat. No. 5,283,317; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696). Using the following olignucleotides:

Coding Strand

G GGT TTG GAA TTC CTA ATA ATG TCT GTA CAA GTA
GAA ACC (SEQ ID No: 3)

Non-coding Strand

GGG TTT CGG GAT CCC GTC ATT CCA GTT TTA
GAAG (SEQ ID No:4)

PCR amplification was carried out from a lymphocyte cDNA library to isolated the coding sequence for the FKBP12 protein. The sequence of the human FKBP12 cloned was confirmed as:

ATGTCCGTACAAGTAGAAACCATCTcCCCAGGAGACGGG
CGCACCTTcCCCAAGCGCGGCCAGACCTGCGTGGTG
CACTACACCGGgATGCTTGAAGATGGAAAGAAATTT
GATTCCTCCCGTGACCGTAACAAGCCCTTTAAGTTt
ATgCTAGGCaAGCAGGAGGTGATCCGAGGCTGGGAA
GAagGGGTTGcCCAGATGAGTGTGGgTCAGCGTGCC
AAaCTgACTAtAtCTCcAGaTtATgCcTATGgTGCCACT
GGGCACcCAGGCATCATCCCACCACATGCCACTCTC
GTCTTCGATGTGGAGCTTCTAAAACTGGAA
TGA (SEQ ID No: 34)

The resulting PCR product containing the human FKBP12 coding sequences was then digested with EcoRI and BamHI, and cloned into the EcoRI+BamHI sites of pBTM116 creating an in-frame fusion between LexA and FKBP12. The resulting plasmid is referred to below as plC504.

B. LexA-(gly)$_6$-FKBP12 Bait

In order to generate an in frame fusion between LexA and FKBP12 separated by six glycine residues, the coding sequence from human FKBP12 was cloned by PCR as above, except that the sense oligonucleotide provided an additional 18 nucleotides which inserted 6 glycines in the open reading frame of the fusion protein. The oligos used for PCR were:

Coding Strand

TCG CCG GAA TTC GGG GGC GGA GGT GGA GGA GTA
CAA GTA GAA ACC ATC        (SEQ ID No: 7)

Non-coding Strand

GGG TTT CGG GAT CCC GTC ATT CCA GTT
TTA GAA G        (SEQ ID No: 8)

The PCR product containing the human FKBP12 coding sequences was then digested with EcoRI and BamHI and cloned into the EcoRI+BamHI sites of pBTM116 as above. The resulting plasmid is referred to below as plC506.

EXAMPLE 2

Construction of the FKBP12 Deletion Strain

A 1.8 kb HindIII-EcoRI yeast genomic fragment containing FKB1 (the *S. Cerveisia* homolog of FKBP12) was cloned into the HindIII+EcoRI sites of pSP72 (Promega).

A one-step PCR strategy was used to create a precise deletion of the FKB1 coding sequences extending from the ATG start codon to the TGA stop codon. Simultaneously a unique BamHI site was introduced in lieu of the FKB1 coding sequences. The oligos used to generate the FKB1 deletion and introduction of the unique BamHI site were:

CGCGGATCCGCGCATTATTACTTGTTTTGATTGAT
TTTTTG        (SEQ ID No: 9)

CGCGGATCCGCGTAAAAGCAAAGTACTATCAATT
GAGCCG        (SEQ ID No: 10)

The yeast ADE2 gene on a 3.6 kb BamHI fragment was then cloned into the unique BamHI site of the plasmid described above to generate the plasmid pVB172. Flanking the ADE2 disruption marker of pVB172 in the 5' and 3' noncoding sequence of FKB1 are XhoI sites. pVB172 was digested with XhoI to release a linear fragment containing ADE2 flanked by FKBI noncoding sequences. This linear fragment was used to transform yeast strain L40 (Mat a his3 Δ200 trpl-901 leu2-3,112 ade2 LYS2::(lexAop)4-HIS3 URA3::(lexAtop)$_8$-lacZ GAL4 gal80) selecting for adenine prototrophy.

ADE+ yeast transformants were tested for rapamycin resistance to confirm that the wild type FKB1 allele was replaced by ADE2. This disruption allele of FKB1 is designated L40-fkbl-2.

EXAMPLE 3

Cloning of Mammalian Rapamycin Target Genes

We used the drug-dependent interaction trap described in Example 1 above, with the LexA binding-domain fusion constructs as bait to detect interaction with clones from cDNA libraries containing VP16 activation-domain fusions. The reporters used as "read-outs" signaling interaction in this system are the *S. cerevisiae* HIS3 and the *E. coli* LacZ genes. The yeast strain L40, the bait vector plasmid pBTM1 16 and the mouse embryonic PCR library in the vector pVP16 were used to construct the cDNA fusion protein library The strain L40-fkb1-2, described above in Example 2, was transformed with each of two bait plasmids, plC504, encoding the LexA-FKBP12 fusion protein, or plC506, encoding the LexA-(gly)6-FKBP12 fusion protein. The transformants, L40-fkb1-2/plC504 (named ICY99) and L40-fkb1-2/plC506 (named ICY101) were maintained on yeast media lacking tryptophan which selects for cells harboring the bait plasmid.

A mouse embryo PCR library in pVP16 (designated pSH10.5), which was generated by standard protocols using random-primed synthesis of 10.5 day-post-coital CD1 mouse embryo polyA+ RNA and size-selected for inserts between 350 bp and 700 bp in length, was used to transform the yeast ICY99 and ICY101. The transformed yeast cells were plated onto media lacking tryptophan and leucine. Approximately $10^7$ transformants from each strain were pooled, thoroughly mixed, and stored frozen in aliquots in 50% glycerol at –80° C.

Prior to screening, cells were thawed, grown for 5 hours in liquid medium, and plated onto selective medium. Approximately $1.5 \times 10^7$ ICY99/pSH10.5 cells were plated onto phosphate-buffered (pH7) synthetic agar medium containing (i) all amino acids except tryptophan, leucine and histidine, (ii) Rapamycin at 125 ng/ml, (iii) the chromogenic substrate X-gal at 100 ng/ml, and (iv) 2% glucose as carbon source, at a plating density of approximately $10^6$ per 15 cm plate. An identical protocol was used for screening ICY101/pSH10.5 transformants, except that a lower concentration of rapamycin was used, at 15.6 ng/ml.

Colonies which both grew on the selective medium and were blue were picked for further testing. These represent cells which do not require hisitidine for growth and which are expressing the β-galactosidase reporter. Candidate colonies appeared between 4–11 days after plating, and the blue color ranged from very light blue to deep blue. They were then subjected to the following tests.

i) Rapamycin-dependence

Each candidate was streaked onto media lacking histidine and containing either 125 ng/ml (for ICY99/pSH10.5 candidates), 15.6 ng/ml (for ICY101/pSH10.5 candidates) rapamycin, or no rapamycin (for both). Candidate clones which grew in the presence of rapamycin and failed to grow on media without rapamycin were chosen for the next test.

For the ICY99/pSH10.5 screen, out of 107 His+ and LacZ+ candidates screened, 24 were rapamycin-dependent for growth on medium lacking hisitidine. For the ICY101/pSH10.5 screen, 20 out of 101 His+ and LacZ+ candidates screened were rapamycin-dependent.

ii) plasmid-linkage

To eliminate false positives caused by chromosomal mutations, each candidate was grown in non-selective medium (YPD) to permit loss of the bait (Trp+) and the cDNA (Leu+) plasmids. Cells which had lost the bait plasmid (Trp–), the cDNA plasmid (Leu–) or both plasmids (Trp– and Leu–), as well as those which had retained both plasmids (Trp+ and Leu+), were streaked onto media containing rapamycin but lacking histidine. Those candidates for which only the derivatives containing both plasmids (Trp+ and Leu+) grew, while the other three derivatives did not, were chosen for further analysis.

For the ICY99/pSH10.5 screen, 23 out of 24 passed the test. For the ICY101/pSH10.5 screen, all 20 passed the test.

iii) Positive and Negative Interaction with Control Baits

Whereas the previous test asked if the interaction disappears when either or both members of the interaction (bait and fish constructs) are lost, the present test asks if the candidate cDNA plasmid (Leu+) can confer interaction when transformed into yeast strains harboring various baits. DNA samples were prepared from each candidate and used to transform E. coli strain B290 (auxotrophic for trptophan and leucine). Since the yeast TRP1 and LEU2 genes can complement the bacterial auxotrophies, respectively, B290 cells containing the bait plasmid are Trp+ and can grow on medium lacking tryptophan, while B290 cells containing the cDNA plasmid are Leu+ and can grow on medium lacking leucine. Plasmid DNA samples were each containing a different bait: i) ICY99, the original strain used in the screen, containing the LexA::FKBP12 bait fusion; ii) ICY101, containing the LexA::(gly)$_6$::FKBP12 bait fusion, and iii) ICY102, containing a LexA fusion bait irrelevant for the present study and which serves as a negative control. The ideal candidate clone should confer His+ and LacZ+ to ICY99 and ICY101 in a rapamycin-dependent manner, but not to ICY102.

For the ICY99/pSH10.5 screen, 11 out of the 23 candidates fulfilled the above criteria. For the ICY101/pSH10.5 screen, 10 out of the 20 candidates fulfilled the above criteria.

The cDNA inserts of these candidate clones were sequenced in both strands using the ABI fluorescent sequencing system. All 11 candidates from the ICY99/pSH10.5 screen, and at least 4 out of 10 of the candidates from the ICY101/pSH10.5 screen contain overlapping fragments of an identical sequence. The 14 clones represent at least 5 independent cloning events from the library as judged by the insert/vector boundaries of each clone. The longest and the shortest inserts differ by approximately 70 bp at the amino-terminus and about 10 bp at the amino-terminus. The partial nucleotide sequence, and corresponding amino acid sequence, isolated from the mouse rapamycin/FKBP12 binding protein (RAPT1 ), is given in SEQ ID No: 1 and SEQ ID No: 2, respectively.

Surprisingly, a search of the GenBank database using the program BLAST, revealed that the peptide encoded by the above sequence shares some homology, though less than 60 percent absolute homology, to the S. cerevisiae TOR1 (and DRR1) and TOR2 gene products previously isolated from yeast.

EXAMPLE 4

Cloning of Human Homologs of Rapamycin Target Genes

Having isolated a partial sequence for the gene encoding a rapamycin-target-protein from a mouse library, we proceeded to isolate the human gene using the mouse sequence as a probe. The plasmid clone p1C99.1.5, containing the longest insert of the RAPT1 clone, was chosen as probe for hybridization. The insert (500 bp) was separated from plasmid DNA by digestion with Not I restriction endonuclease followed by agarose gel electrophoresis and fragment purification. The fragment was radiolabelled with $\alpha P^{32}$-labeled dCTP by random-incorporation with the Klenow fragment of DNA polymerase. The radiolabelled DNA probe was isolated away from free nucleotides by a G50 column, alkali-denatured, and added to the hybridization mix at $2 \times 10^6$ cpm/ml.

Approximately $3 \times 10^6$ phage of a human B cell cDNA library in λ-pACT (FIG. 1) were screened by filter hybridization using the probe described above, in 30% formamide, 5×SSC, 5× Denhardts, 20 μg/ml denatured salmon sperm DNA, and 1% SDS, at 37° C. Following hybridization, the filters were washed at 0.5×SSC and 0.1% SDS, at 50° C. These represent conditions of medium stringency appropriate for mouse-to-human cross-species hybridizations. A number of positive plaques were obtained, and several were analyzed. A number of the isolated clones turned out to be various 3' fragments of the same gene, or very closely related genes, which, after sequence analysis, was determined to be the human RAPT1 gene. The clone containing the longest coding sequence fragment, comprising what is believed to be roughly half the full-length protein (C-terminus) and including the FKBP/rapamycin binding site and the putative PI-kinase acitivity, is designated as plasmid pIC524. A deposit of the pACT plasmid form of pIC524 was made with the American Type Culture Collection (Rovkville, Md.) on May 27, 1994, under the terms of the Budapest Treaty. ATCC Accession number 75787 has been assigned to the deposit.

FIG. 1 is a map of the human RAPT1 clone of pIC524 (inserted at the XhoI site). The insert is approximately 3.74 kb in length, and nucleotide RAPT1 coding sequence from the insert has been obtained and is represented by nucleotide residues 2401–5430 of SEQ ID No. 11. The corresponding amino acid sequence is represented by residues His801-Trp1809 of SEQ ID No. 12. The region of the human RAPT1 clone corresponding to the mouse RAPT1 fragment is greater than 95% homologous at the amino acid level and 90% homologous at the nucleotide level. In addition to the pIC524 clone, further 5' sequence of the human RAPT1 gene was obtained from other overlapping clones, with the additional sequence of the 3'end of the ~5.4 kb partial gene given in SEQ ID No. 11. Furthermore, SEQ ID No. 19 provides additional 3' non-coding sequence (obtained from another clone) which flanks the RAPT1 coding sequence.

It will be evident to those skilled in the art that, given the present sequence information, PCR primers can be designed to amplify all, or certain fragments of the RAPT1 gene sequence provided in pIC524. For example, the primers TGAAGATACCCCACCAAACCC (SEQ ID No. 21) and TGCACAGTTGAAGTGAAC (SEQ ID No. 22) correspond to pACT sequences flanking the XhoI site, and can be used to PCR amplify the entire RAPT1 sequence from pIC524. Alternatively, primers based on the nucleic acid sequence of SEQ ID No. 11 can be used to amplify fragments of the RAPT1 gene in pIC524. The PCR primers can be subsequently sub-cloned into expression vectors, and used to produce recombinant forms of the subject RAPT1 protein. Thus, the present provides recombinant RAPT1 proteins encoded by recombinant genes comprising RAPT1 nucleotide sequences from ATCC deposit number 75787. Moreover, it is clear that primer/probes can be generated which include even those portion of pIC524 not yet sequenced by simply providing PCR primers based on the known sequences.

Furthermore, our preliminary data indicate that other proteins which are related to RAPT1, e.g. RAPT1 homologs, were also obtained from the present assay, suggesting that RAPT1 is a member of a larger family of related proteins.

EXAMPLE 5

Cloning of Novel Human Ubiquitin Conjugating Enzyme

Constructs similar to those described above for the drug-dependent interaction trap assay were used to screen a WI38 (mixed $G_0$ and dividing fibroblast) cDNA library (Clonetech, Palo Alto Calif.) in pGADGH (XhoI insert, Clonetech). Briefly, the two hybrid assay was carried out as above, using GAL4 constructs instead of LexA, and in an HF7C yeast cell (Clonetech) in which FKB1 gene was disrupted (see Example 1). Of the clones isolated, a novel human ubiquitin-conjugating enzyme (rap-UBC) has been identified. A deposit of the pGADGH plasmid (clone "SMR-4-15") was made with the American Type Culture Collection (Rovkville, Md.) on May 27, 1994, under the terms of the Budapest Treaty. ATCC Accession number 75786 has been assigned to the deposit. The insert is approximately 1 kB.

The sequence of the 5' portion of the SMR4-15 insert is given by SEQ ID No. 23 (nucleotide) and SEQ ID No. 24 (amino acid) and comprises a substantial portion of the coding region for rap-UBC, including the active site cysteine. The sequence for the 3' portion of the clone is provided by SEQ ID No. 25. As described above, primers based on the nucleic acid sequence of SEQ ID No. 23 (and 25) can be used to amplify fragments of the rap-UBC gene from SMR4-15. The PCR primers can be subsequently subcloned into expression vectors, and used to produce recombinant forms of the subject enzyme. Thus, the present provides recombinant rap-UBC proteins encoded by recombinant genes comprising rap-UBC nucleotide sequences from ATCC deposit number 75786.

EXAMPLE 6

Construction of the Serine-to-Argenine mRAPT1 Mutation

The smallest mRAPT1 clone that interacted with the FKBP12/rapamycin complex was 399 bp, defingin a rapamycin binding domain. The RAPT1 binding domain corresponds to a region in yeast TOR1/TOR2 located immediately upstream, but outside of the lipid kinase consensus sequence. This region contains the serine residue which when mutated in yeast TOR1 confers resistance to rapamycin (Cafferkey et al. (1993) *Mol Cell Biol* 13:6012–6023). A mouse RAPT1 serine-to-argenine mutation was constructed by oligonucleotide mutagenesis. Coding and noncoding strand oligonucleotides containing the mutations were: GAAGAGGCAAGACGCTTGTAC (SEQ ID NO:26) and GTACAAGCGTCTTGCCTCTT (SEQ ID NO:27). PCR reactions were performed using these oligonucleotides in combination with oligonucleotides GAGTTTGAGCAGAT-GTTTA (SEQ ID NO:28) and the M13 universal primer which are sequences in the pVP16 vector, 5' and 3' of the mRAPT1 insert, respectively. pVP16 containing mRAPT1 was used as the template for PCR. The PCR product, digested with BamHI and EcoRI, was cloned into the BamHI and EcoRI sites in pVP16. The resulting clone was sequenced to verify that the clone contained the serine-to-argenine mutation and no others.

The smallest mRAPT1 clone that interacted with the FKBP12/rapamycin complex was 399 bp, defining the RAPT1 binding domain. The RAPT1 binding domain corresponds to a region in yeast TOR located immediately upstream, but outside of the lipid kinase consensus sequence. This region contains the serine residue which when mutated in yeast TOR1 (also called DRR1) confers resistance to rapamycin (Cafferkey et al. (1993) *Mol. Cell Biol.* 13:6012–6023; Helliwell et al. (1994) *Mol. Cell Biol.* 5:105–118). The corresponding mutation was constructed in mRAPT1. The serine-to-argenine mutation abolishes interaction of mRAPT1 with the FKBP12/rapamycin complex (see FIG. 3), activating neither HIS3 nor lacZ expression on the two-hybrid assay, indicating that the serine is involved in the association of the FKBP12/rapamycin complex with mRAPT1.

EXAMPLE 7

Northern Analysis

The multiple tissue Northern blots (containing 2 μg of human RNA per lane) were obtained from Clonetech Labs., Inc. Hybridizations were at 42° C. in 5× SSPE, 5× Denhardt's, 30% formamide, 1% SDS and 200 μg/ml denatured salmon sperm DNA. Washes were at 0.1×SSC and 0.1% SDS at 55° C. The blot was exposed for 5 days prior to autoradiography. The levels of RNA loaded in each lane were independently monitored by hybridizing the same blots with a human G3PDH probe and were found to be similar in all lanes, with the exception of skeletal muscle, which had approximatelly 2–3 fold the signal.

RAPT1 specifies a single transcript of approximatelly 9 kb that is present in all tissues examined, exhibiting the highest levels in testis. The transcript is sufficient to encode a protein equivalent to the size of yeast TOR which is 284 kDa. Assuming that RAPT1 is of similar size, a small fragment of 133 amino acids has been cloned from within a large protein, but which fragment is sufficient to bind FKBP12/rapamycin complex.

EXAMPLE 8

High throughput Assay Based on the Two-hybrid System for Identifying Novel Rapamycin Analogs To develop a high throughput screen based on the two-hybrid system, we devised a procedure to quantitate protein-protein interaction mediated by a small molecule. Since protein-protein interaction in the two-hybrid system stimulates transcription of the lacZ reporter gene, the assay utilizes a substrate of β-galactosidase (the lacZ gene product lacZ gene product) which when cleaved produces a chemiluminescent signal that can be quantitated. This assay can be performed in microtiter plates, allowing thousands of compounds to be screened per week. The assay includes the following steps:

1. Inoculate yeast cells from a single colony into 50 ml of growth medium, synthetic complete medium lacking leucine and tryptophan (Sherman, F. (1991) *Methods Enzymol.* 194:3–20). Incubate the flask overnight at 30° C. with shaking (~200 rpm).
2. Dilute the overnight culture to a final $A_{600}$ of 0.02 in growth medium and incubate overnight as described in step 1.
3. Dilute the second overnight culture to a final $A_{600}$ of 0.5 in growth medium. Using a Quadra 96 pipettor (TomTec, Inc.), dispense 135 μl aliquots of the cell suspension into wells of a round bottom microtiter plate pre-loaded with 15 μl/well of the compound to be tested at various concentrations. (The compounds are dissolved in 5% dimethyl sulfoxide, so that the final DMSO concentration added to cells is 0.5% which does not perturb yeast cell growth.) Cover microtiter plates and incubate at 30° C. for 4 hr with shaking at 300 rpm.
4. Centrifuge microtiter plate for 10 min at 2000 rpm. Remove the supernatant with the Quadra 96 pipettor and wash with 225 μl phosphate buffered saline.
5. Dispense 100 μl of lysis buffer (100 mM $M_2HPO_4$ pH 7.8; 0.2% Triton X-100; 1.0 mM ditiothriotol) into each well, cover, and incubate for 30 min at room temperature with shaking at 300 rpm.
6. Dispense into each well of a Microfluor plate (Dynatech Laboratories, Chantilly, Va.), 50 μl of the chemiluminescent substrate, Galacton Plus™ (Tropix, Inc., Bedford, Ma.) in diluent (100 mM $Na_2HPO_4$, 1 mM MgC12, pH 8.0). To these wells, transfer 20 μl of cell lysate and incubate in the dark for 60 min at room temperature.
7. Add to each well 75 μl of Emeral™ accelerator. Cover plate and count in a Topcount scintillation counter (Packard, Inc.) for 0.01 min/well.

The rapamycin target proteins, isolated as described above, were incorporated into the quantitative assay, as was a variety of FKBPs. The FKBPs included in the screen were human FKBP12 and that from pathogenic fungi, FKBP13 (Jin et al. (1991) *Proc. Natl. Acad. Sci.* 88:6677) and FKBP25 (Jin et al. (1992) *J. Biol. Chem.* 267:2942; Galat et al. (1992) *Biochem.* 31:2427–2434). Yeast strains containing different FKBP-target pairs can be tested against libraries of rapamycin and FK506 analogs. Such a screen can yield different classes of compounds including (i) target-specific compounds, those that mediate interaction between a specific target and more than one FKBP, (ii) FKBP-specific compounds, those that mediate interaction between a particular FKBP and more than one target and, most ideally, (iii) FKBP/target-specific compounds, those that mediate interaction between a particular FKBP and target. The protein interactions mediated by the test compounds and measured in this assay can be correlated with immunosuppressive, antifungal, antiproliferative and toxicity profiles, as well as their Ki's for inhibition of FKBP PPIase activity.

Figure 2:
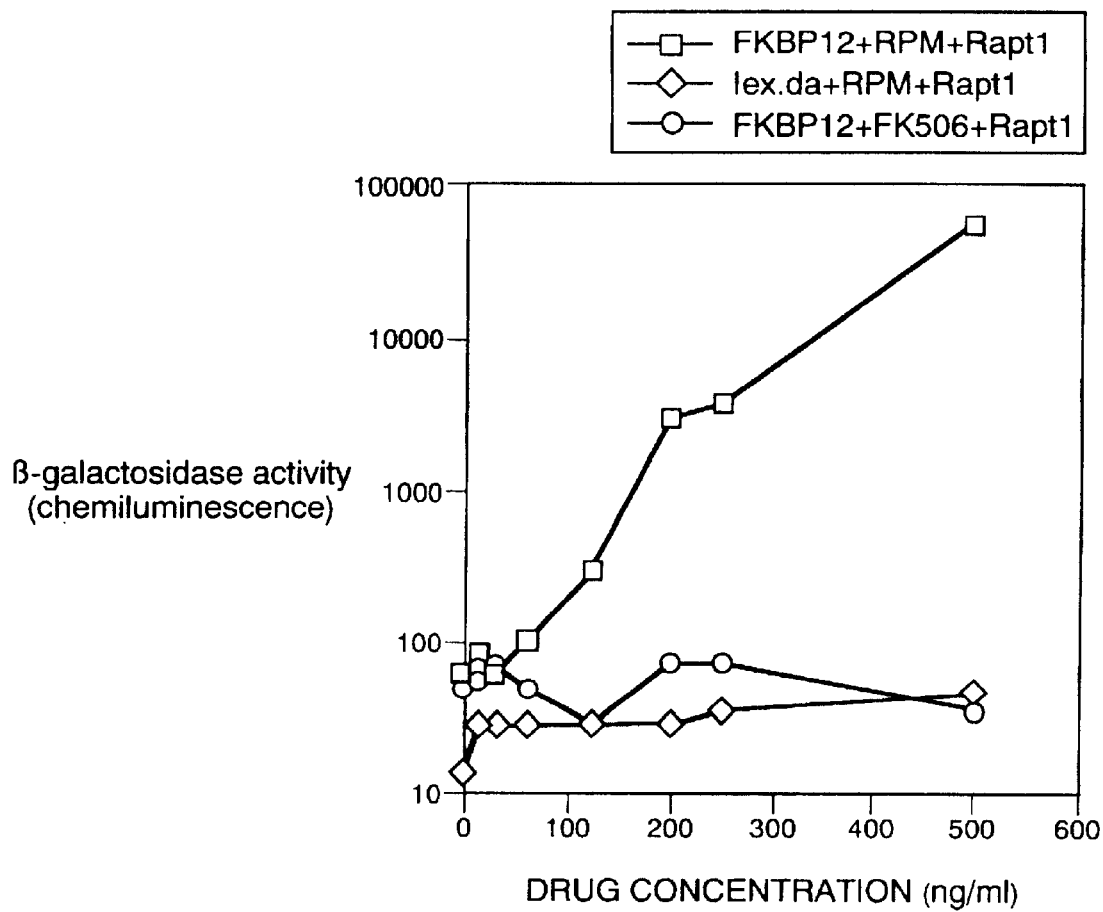
FIG. 2 illustrates the interaction of FKBP12 and hRAPT1 (rapamycin-binding domain) as a function of rapamycin concentration. INteraction is detected as β-galactosidase activity. No interaction is detected if FK506 is used in place of rapamycin, or if lex.da (a control plasmid) replaces FKBP12.
Figure 3A:
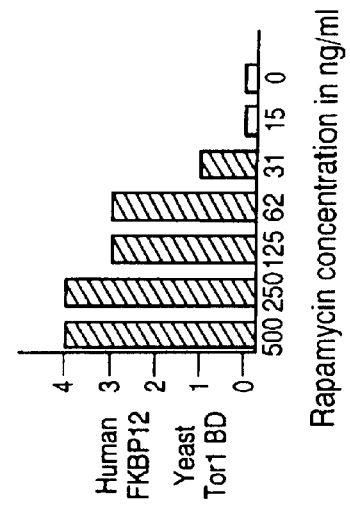
Figure 3B:
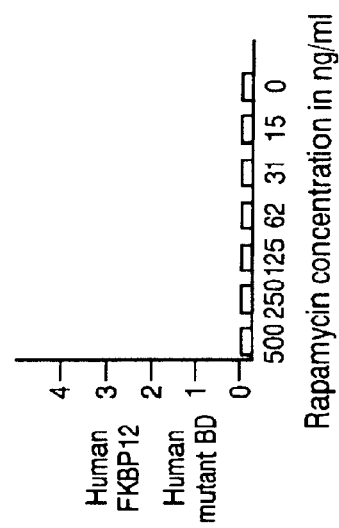
Figure 3C:
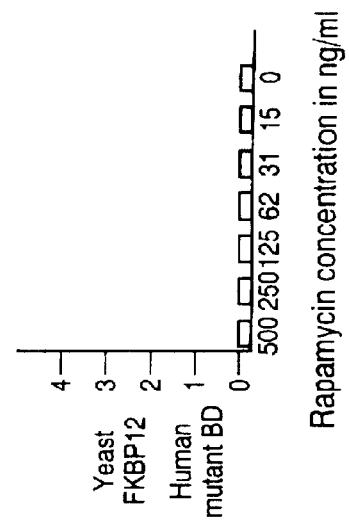
Figure 3D:
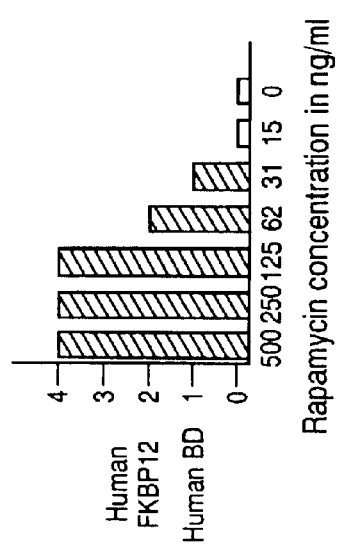
Figure 3E:
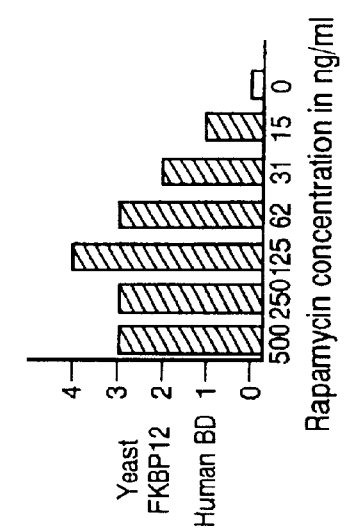
Figure 3F:
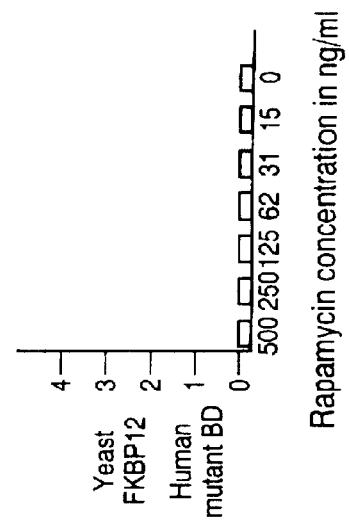

Using the quantitative chemiluminescence assay described above, the interaction of human LexA-FKBP12 and VP16-RAPT1 was analyzed in the presence and absence of rapamycin. Interaction between FKBP12 and RAPT1 was measured as a function of drug concentration. Addition of rapamycin from 0 to 500 ng/ml increased β-galactosidase activity approximately one thousand-fold. This effect was specific for rapamycin; FK506 over the same concentration range did not increase β-galactosidase activity significantly over background levels. If lexA-da, a control construct, is substituted for the lexA-FKBP12, β-galactosidase activity does not increase as a function of rapamycin addition. The basal levels of β-galactosidase in the negative controls are 0.1 per cent of the maximum levels detected in the yeast strain containing the FKBP12 and RAPT1 constructs, grown in media containing 500 ng/ml rapamycin. These results, illustrated in FIG. 2, indicate that protein interactions mediated by a small molecule in the two-hybrid system can be quantitated and assayed in a microtiter format that can be used for high throughput screening. Employing various FKBPs and RAPT1 proteins in the two-hybrid format (FIG. 3) rapamycin-mediated interactions were measured in this quantitative assay.

EXAMPLE 9

In vitro Protein Interactions Mediated by Rapamycin

Drug-mediated interactions of FK506-binding proteins and the RAPT1 proteins is analyzed in vitro using purified FKBP12 fused to glutathione-S-transferase (GST) and $^{35}$S labeled RAPT1 proteins prepared by in vitro transcription and translation. For this purpose FKBP12 is fused in the frame of GST in pGEX (Pharmacia, Piscataway, N.J.). GST-FKBP12 fusion proteins are expressed and purified from *E. coli* (Vojtek et al. (1993) Cell 74:205–214). RAPT1 coding sequences are cloned behind the CMV and T7 promoters in the mammalian expression vector, pX (Superti-Furga et al. (1991) *J. Immunol. Meths.* 151:237–244). RAPT1 sequences are transcribed from the T7 promoter and translated in vitro using commercially available reagents (Promega, Madison, Wis.) in a reaction containing $^{35}$S-methionine. For in vitro binding (Toyoshima et al. (1994) *Cell* 78:67–74), 5 to 20 μl of the in vitro transcription/translation reactions are added to 200 μl of binding buffer (20 mM HEPES[pH7.4], 150 mM NaCl, 10% glycerol, 0.05% NP-40). After addition of 10 μl of GST-FKBP12 bound to glutathione-agarose beads, the reaction is incubated at 4° C. for 2 hr with rotation. Various contrations of drug are added to reactions, such as 0.1 to 10-fold that of FKBP 12 on a molar basis. No drug is added to control reactions. The agarose beads are then precipitated and washed four times with binding buffer. Bound proteins iseluted by boiling in Laemmli sample buffer, resolved on 4–20% gradient SDS polyacrylamide gels, and visualized by autoradiography. Detection of $^{35}$S-labelled RAPT1 protein from binding reactions containing drug demonstrates direct binding to FKBP 12 as a function of drug.

EXAMPLE 10

Effect of RAPT1 Mutations on Complex Formation and Rapamycin Sensitivity

To more particularly map the rapamycin-binding domain of RAPT1 requires the isolation of mutants that fail to bind to a FKBP/rapamycin complex. As described in the Examples above, association with the FKBP/rapamycin can be tested in the LexA two-hybrid system in which FKBP12 is expressed as a fusion to LexA and RAPT1 proteins are expressed as fusions to the VP16 activation domain. Accordingly, a library of mutant RAPT1 proteins is generated by mutagenizing coding sequences through PCR-generated random mutagenesis (Cadwell and Joyce (1992) *PCR Methods Appl* 2:28–33). The 5' and 3' oligos for PCR contain BamH1 and EcoRI restriction sites, respectively, that allow subsequent cloning of the PCR products into pVP16 creating an in-frame fusion. In addition, the 3' oligo contains a 27 bp HA epitope sequence followed by an in frame stop codon. The addition of the HA epitope tag to the C-terminal end of the fusion proteins allows the characterization of the mutant RAPT1 proteins (see below).

Upon completion of the mutagenesis, the EcoR1-BamHI digested PCR products are inserted into pVP16. The library of mutant RAPT1 proteins is amplified by transformation into *E. coli*. To identify those mutations that impair the ability of a RAPT1 to interact with an FKBP/rapamycin complex, the mutagenized RAPT1 library is introduced into a yeast strain containing the LexA-FKBP bait protein. Each transformed cell carries one individual mutant RAPT1 fused to the transcriptional activator VP16. Interaction between the FKBP and wild type RAPT1 occurs when cells are grown in media containing rapamycin, inducing lacZ expression and turning colonies blue on X-GAL indicator plates. Colonies in which the interaction between an FKBP/rapamycin complex and the RAPT1 mutant is impaired are light blue or white. Two classes of mutations can produce this phenotype: nonsense mutations resulting in truncated version of RAPT1 or sense mutations that affect the binding of RAPT1 to the FKBP/rapamycin complex. To distinguish between these two types of mutations, total protein extracts made from these colonies is subjected to Western blot analysis using an anti-HA antibody. Nonsense mutations that give rise to shorter, truncated proteins do not contain the HA epitope at their C-terminus and thus are not be detected by the anti-HA antibody. Conversely, full-length proteins with an incorporated sense mutations are detected with this antibody.

The library plasmids from the light blue or white colonies that express full-length RAPT1 protein with the HA epitope are rescued by retransformation into *E. Coli*. The position of the mutation is determined by sequence analysis, and the phenotype verified by retransformation of these plasmids back into the yeast strain containing LexA-FKBP12.

Mutants that retest can also be cloned into the mammalian expression vector, pX. pX-RAPT1 or pX lacking RAPT1 sequences, are thenintroduced into the lymphoid (CTLL and Kit225) and nonlymphoid cells (MG63 and RH30) sensitive to rapamycin. The effect of the mutation on rapamycin sensitivity is measured in terms of inhibition of DNA synthesis monitored by BrdU incorporation. Mutants that confer resistance of rapamycin by virtue of being unable to bind to the FKBP12/rapamycin complex indicate which mutations mediate drug sensitivity in lymphoid and non-lymphoid cells. Of particular interest is whether different RAPT1s mediate drug sensitivity in different cell types.

EXAMPLE 11

Cloning of a RAPT1-like Polypeptide from Candida albican

In order to clone homologs of the RAPT1 genes from human pathogen Candida, degenerate oligonucleotides based on the conserved regions of the RAPT1 and TOR proteins were designed and used to amplify C. albicans cDNA in λZAP (strain 3153A). The amplification consisted of 30 cycles of 94° C. for 1minute, 55° C. for 1 minute and 72° C. for 1 minute with the PCR amplimers GGNAARGC-NCAYCCNCARGC SEQ ID NO: 29, and ATNGCNGGR-TAYTGYTGDATNTC. The PCR reactions were separated on a 2.5% low melting agarose gel, that identified a sizable fragment. The fragment was eluted and cloned into pCRII (TA cloning system, Invitrogen corporation).

The C. albicans DNA probes were $^{32}$P-labeled by nick translation and used on Southern blots to confirm the species identity of the fragments and to further screen C. albicans cDNA libraries. Sequencing of the larger cDNAs confirmed the identity of the clones. The partial sequence of a C. albicans RAPT1-like polypeptide, with the open-reading frame desiganted, is provided by SEQ ID Nos. 13 and 14.

All of the above-cited references and publications are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated antibody which specifically binds to a protein having the amino acid sequence of SEQ ID NO:2.

2. An isolated antibody which specifically binds to a protein having the amino acid sequence of SEQ ID NO:12.

3. The isolated antibody of claim 1 or 2, which specifically binds to an FKBP/rapamycin-binding (FRB) domain.

4. The isolated antibody of claim 1, which does not substantially cross-react with a protein which is less than 90% homologous to SEQ ID NO:2.

5. The isolated antibody of claim 4, which does not substantially cross-react with a protein which is less than 95% homologous to SEQ ID NO:2.

6. The isolated antibody of claim 2, which does not substantially cross-react with a protein which is less than 90% homologous to SEQ ID NO:12.

7. The isolated antibody of claim 6, which does not substantially cross-react with a protein which is less than 95% homologous to SEQ ID NO:12.

8. A purified preparation of an antibody, or an antigen binding fragment thereof, which is specifically immunoreactive with a protein having an amino acid sequence of SEQ ID NO:2.

9. A purified preparation of an antibody, or an antigen binding fragment thereof, which is specifically immunoreactive with a protein having an amino acid sequence of SEQ ID NO:12.

10. A polyclonal antibody preparation comprising antibodies specifically immunoreactive with a protein having an amino acid sequence of SEQ ID NO:2.

11. A polyclonal antibody preparation comprising antibodies specifically immunoreactive with a protein having an amino acid sequence of SEQ ID NO:12.

12. A monoclonal antibody composition comprising a monoclonal antibody, or an antigen binding fragment thereof, which is specifically immunoreactive with a protein having an amino acid sequence at least 90 percent homologous to SEQ ID NO:2.

13. A monoclonal antibody composition comprising a monoclonal antibody, or an antigen binding fragment thereof, which is specifically immunoreactive with a protein having an amino acid sequence at least 90 percent homologous to SEQ ID NO:12.

14. The preparation of claim 8, which is specifically immunoreactive with a protein having an amino acid sequence at least 90 percent homologous to SEQ ID NO:2.

15. The preparation of claim 14, which is specifically immunoreactive with a protein having an amino acid sequence at least 95 percent homologous to SEQ ID NO:2.

16. The preparation of claim 9, which is specifically immunoreactive with a protein having an amino acid sequence at least 90 percent homologous to SEQ ID NO:12.

17. The preparation of claim 16, which is specifically immunoreactive with a protein having an amino acid sequence at least 95 percent homologous to SEQ ID NO:12.

* * * * *